US011058751B1

(12) United States Patent
Gifford et al.

(10) Patent No.: US 11,058,751 B1
(45) Date of Patent: Jul. 13, 2021

(54) COMPOSITIONS FOR OPTIMIZED RAS PEPTIDE VACCINES

(71) Applicant: Think Therapeutics, Inc., Newton, MA (US)

(72) Inventors: David Gifford, Newton, MA (US); Brandon Carter, Cambridge, MA (US)

(73) Assignee: Think Therapeutics, Inc., Newton, MA (US)

( * ) Notice: Subject to any disclaimer, the term of this patent is extended or adjusted under 35 U.S.C. 154(b) by 0 days.

(21) Appl. No.: 17/100,630

(22) Filed: Nov. 20, 2020

(51) Int. Cl.
*A61K 39/00* (2006.01)
*A61P 35/00* (2006.01)

(52) U.S. Cl.
CPC .......... *A61K 39/0005* (2013.01); *A61P 35/00* (2018.01); *C12Y 306/05002* (2013.01); *A61K 2039/585* (2013.01)

(58) Field of Classification Search
None
See application file for complete search history.

(56) References Cited

U.S. PATENT DOCUMENTS

| | | |
|---|---|---|
| 8,741,576 B2 | 6/2014 | Tangri et al. |
| 9,340,577 B2 | 5/2016 | Grey et al. |
| 10,738,355 B2 | 8/2020 | Sahin et al. |
| 2011/0257890 A1 | 10/2011 | Weinschenk et al. |
| 2016/0125129 A1 | 5/2016 | Sahin et al. |
| 2018/0066017 A1 | 3/2018 | Hunt et al. |
| 2019/0322714 A1 | 10/2019 | Petit et al. |
| 2020/0061166 A1 | 2/2020 | Sahin et al. |
| 2020/0069782 A1 | 3/2020 | Biskup et al. |

FOREIGN PATENT DOCUMENTS

| | | |
|---|---|---|
| WO | WO-97/33602 A1 | 9/1997 |
| WO | WO-2005/042698 A2 | 5/2005 |
| WO | WO-2018/102585 | 6/2018 |

OTHER PUBLICATIONS

Alhadj Ali et al., "Metabolic and immune effects of immunotherapy with proinsulin peptide in human new-onset type 1 diabetes," Science Translation Medicine, Aug. 9, 2017, vol. 9;9(402):eaaf7779. 9 pages.
Candia et al., "On Peptides and Altered Peptide Ligands: From Origin, Mode of Action and Design to Clinical Application (Immunotherapy)," International Archives of Allergy and Immunology, published online Sep. 20, 2016; vol. 170(4), pp. 211-233.
Gibson et al., "Proinsulin multi-peptide immunotherapy induces antigen-specific regulatory T cells and limits autoimmunity in a humanized model," Clinical Experimental Immunology, Dec. 2015, vol. 182(3), pp. 251-260.
Guevara-Patino, et al., "Optimization of a self antigen for presentation of multiple epitopes in cancer immunity," The Journal of Clinical Investigation, May 2006, vol. 116, No. 5, pp. 1382-1390.
Hong et al., "Epitope-optimized alpha-fetoprotein genetic vaccines prevent carcinogen-induced murine autochthonous hepatocellular carcinoma," Hepatology, Apr. 2014, vol. 59(4), pp. 1448-1458.

(Continued)

*Primary Examiner* — Elly-Gerald Stoica
(74) *Attorney, Agent, or Firm* — Wilmer Cutler Pickering Hale and Dorr LLP

(57) ABSTRACT

The present disclosure provides for methods, systems, and compositions of nucleic acid and peptide sequences. The present disclosure provides for a nucleic acid sequence encoding two or more amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41. The present disclosure also provides for an immunogenic peptide composition comprising two or more peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41. The present disclosure further provides for a nucleic acid sequence encoding one or more amino acid sequences selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65. The present disclosure additionally provides for an immunogenic peptide composition comprising one or more peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

30 Claims, 10 Drawing Sheets
Specification includes a Sequence Listing.

(56) References Cited

OTHER PUBLICATIONS

Houghton et al., "Immunological validation of the EpitOptimizer program for streamlined design of heteroclitic epitopes," Vaccine, available online Jun. 4, 2007, vol. 25(29), pp. 5330-5342.

Reynisson et al., "NetMHCpan-4.1 and NetMHCIIpan-4.0: improved predictions of MHC antigen presentation by concurrent motif deconvolution and integration of MS MHC eluted ligand data," Nucleic Acids Research, published online May 14, 2020; vol. 48(W1), pp. W449-W454.

Chicz, et al., "Predominant naturally processed peptides bound to HLA-DR1 are derived from MHC-related molecules and are heterogeneous in size," Nature, Aug. 27, 1992, vol. 358, pp. 764-768.

Cleveland et al., "Routine large-scale production of monoclonal antibodies in a protein-free culture medium," Journal of Immunological Methods, Jan. 28, 1983, vol. 56, Issue 2, pp. 221-234.

Croft et al., "Most viral peptides displayed by class I MHC on infected cells are immunogenic," Proceedings of the National Academy of Sciences, Feb. 19, 2019, vol. 116, No. 8, pp. 3112-3117.

Dai et al., "Machine learning optimization of peptides for presentation by class II MHCs," bioRxiv, posted Aug. 18, 2020. 35 pages. (https://doi.org/10.1101/2020.08.18.256081).

Jaravine et al., "Assessment of cancer and virus antigens for cross-reactivity in human tissues," Bioinformatics, Jan. 1, 2017, vol. 33, No. 1, pp. 104-111.

Jaravine et al., "Expitope 2.0: a tool to assess immunotherapeutic antigens for their potential cross-reactivity against naturally expressed proteins in human tissues," BMC Cancer, Dec. 28, 2017, vol. 17:892. 9 pages.

Klinger et al., "Multiplex identification of antigen-specific T cell receptors using a combination of immune assays and immune receptor sequencing," PLOS One, Oct. 28, 2015, vol. 10(10), e0141561. 21 pages.

Kranz et al., "Systemic RNA delivery to dendritic cells exploits antiviral defence for cancer immunotherapy," Nature, Jun. 16, 2016, vol. 534(7607), pp. 396-401, and Methods. 16 pages.

Kreiter, et al., "Increased antigen presentation efficiency by coupling antigens to MHC class I trafficking signals," The Journal of Immunology, Jan. 2008, vol. 180(1), pp. 309-318, and Corrections. 12 pages.

Liu et al,. "Predicted Cellular Immunity Population Coverage Gaps for SARS-CoV-2 Subunit Vaccines and their Augmentation by Compact Peptide Sets,"bioRxiv, posted Oct. 21, 2020, 29 pages. (https://www.biorxiv.org/content/10.1101/2020.08.04.200691v2).

Liu et al., "Computationally Optimized SARS-CoV-2 MHC Class I and II Vaccine Formulations Predicted to Target Human Haplotype Distributions," Cell Systems, Aug. 26, 2020, vol. 11(2), pp. 131-144, and Methods. 23 pages.

Maa et al., "Biopharmaceutical Powders: Particle Formation and Formulation Considerations," Current Pharmaceutical Biotechnology, Nov. 2000, vol. 1, No. 3, pp. 283-302.

Mösch et al., "Machine Learning for Cancer Immunotherapies Based on Epitope Recognition by T Cell Receptors," Frontiers in Genetics, Nov. 19, 2019, vol. 10, Article 1141. 17 pages.

Nair et al., "A simple practice guide for dose conversion between animals and human," Journal of Basic and Clinical Pharmacy, Article Review, Mar.-May 2016, vol. 7, Issue 2, pp. 27-31.

Ng et al., "In silico-guided sequence modifications of K-ras epitopes improve immunological outcome against G12V and G13D mutant KRAS antigens," PeerJ., published Jul. 20, 2018, 6:e5056. doi: 10.7717/peerj.5056. 21 pages.

Nielsen et al., "The role of the proteasome in generating cytotoxic T-cell epitopes: insights obtained from improved predictions of proteasomal cleavage," Immunogenetics, published online Mar. 3, 2005, vol. 57, pp. 33-41.

Ogishi et al., "Quantitative Prediction of the Landscape of T Cell Epitope Immunogenicity in Sequence Space," Frontiers in Immunology, Apr. 16, 2019, vol. 10, Article 827. 20 pages.

Park et al., "Accurate structure prediction of peptide-MHC complexes for identifying highly immunogenic antigens," Mol. Immunol., Nov. 2013, vol. 56(0):81-90. NIH Author Manuscript. 25 pages.

Rist et al., "HLA peptide length preferences control CD8+ T cell responses," The Journal of Immunology, published online Jun. 7, 2013, vol. 191(2), pp. 561-571. 12 pages.

Sahin et al., "Personalized RNA mutanome vaccines mobilize poly-specific therapeutic immunity against cancer," Nature, Jul. 13, 2017, vol. 547(7662), pp. 222-226, and Methods. 19 pages.

Slota et al., "ELISpot for measuring human immune responses to vaccines," Expert Review of Vaccines, Mar. 2011, vol. 10(3), pp. 299-306. NIH Author Manuscript. 14 pages.

Soria-Guerra et al,. "An overview of bioinformatics tools for epitope prediction: Implications on vaccine development," Journal of Biomedical Informatics, Feb. 2015, vol. 53, pp. 405-414.

Tapia-Calle et al., "A PBMC-Based System to Assess Human T Cell Responses to Influenza Vaccine Candidates In Vitro," Vaccines, Nov. 13, 2019, vol. 7(4):181. 26 pages.

Trolle et al., "The length distribution of class I—restricted T cell epitopes is determined by both peptide supply and MHC allele—specific binding preference," The Journal of Immunology, Feb. 15, 2016, vol. 196(4), 1480-1487. HSS Author Manuscript. 21 pages.

Woodham et al., "Nanobody-Antigen Conjugates Elicit HPV-Specific Antitumor Immune Responses," Cancer Immunology Research, Jul. 2018, vol. 6(7); pp. 870-880.

Zirlik et al., "Cytotoxic T cells generated against heteroclitic peptides kill primary tumor cells independent of the binding affinity of the native tumor antigen peptide," Blood, Dec. 1, 2006, Vo. 108, No. 12, pp. 3865-3870.

Dastagir et al., "Efficient Presentation of Multiple Endogenous Epitopes to Both CD4+ and CD8+ Diabetogenic T Cells for Tolerance," Molecular Therapy: Methods & Clinical Development, Mar. 2017, vol. 4, pp. 27-38.

Alvarez, B. et al., "NNAlign_MA; MHC Peptidome Deconvolution for Accurate MHC Binding Motif Characterization and Improved T-cell Epitope Predictions", Molecular & Cellular Proteomics, Dec. 2019, vol. 18(12), pp. cover, 2459-2477 (20 pages).

Asahara et al., "Phase 1/11 clinical trial using HLA-A24-restricted peptide vaccine derived from KIF20A for patients with advanced pancreatic cancer Journal of Translational Medicine," vol. 11, article 291, 13 total pages (Year: 2013).

Bae et al., "Myeloma-Specific Multiple Peptides Able to Generate Cytotoxic T Lymphocytes: A Potential Therapeutic Application in Multiple Myeloma and Other Plasma Cell Disorders," Clinical Cancer Research, vol. 18, pp. 4850-4860 (Year: 2012).

Bhasin, M. and Raghava, G.P.S., "Prediction of Promiscuous and High-Affinity Mutated MHC Binders", Hybridoma and Hybridomics, Nov. 4, 2003, vol. 22, 229-234, (8 pages).

Dey et al., "A Bioinformatics approach to designing a Zika virus vaccine," Computational Biology and Chemistry, vol. 68, pp. 143-152 (Year: 2017).

Hollingsworth et al., "Turning the corner on therapeutic cancer vaccines," npj Vaccines, published online Feb. 8, 2019, vol. 4(7), pp. 1-10.

Hoppes et al., "Altered Peptide Ligands Revisited: Vaccine Design through Chemically Modified HLA-A2-Restricted T Cell Epitopes," Journal of Immunology, vol. 193, pp. 4803-4813 (Year: 2014).

Jain et al., "Synthetic Tumor-Specific Breakpoint Peptide Vaccine in Patients with Chronic Myeloid Leukemia and Minimal Residual Disease," Cancer, vol. 115, pp. 3924-3934 (Year: 2009).

Jurtz, V. et al., "NetMHCpan-4.0: Improved Peptide-MHC Class I Interaction Predictions Integrating Eluted Ligand and Peptide Binding Affinity Data", The Journal of Immunology, prepublished online Oct. 4, 2017, vol. 199, pp. 3360-3368 (9 pp.).

Krienke, C. et al., "A noninflammatory mRNA vaccine for treatment of experimental autoimmune encephalomyelitis", Science, Jan. 8, 2021, vol. 371, pp. 145-153 (10 pages).

Longmate, et al., "Population coverage by HLA class-I restricted cytotoxic T-lymphocyte epitopes," Immunogenetics vol. 52, pp. 165 -173 (Year: 2001).

Mahanty, et al., "Immunogenicity of infectious pathogens and vaccine antigens," BMC Immunology, published online May 29, 2015, vol. 16(1), pp. 1-6.

(56) References Cited

OTHER PUBLICATIONS

Mashiba, et al., "Identification of CTL epitopes in hepatitis C virus by a genome-wide computational scanning and a rational design of peptide vaccine," Immunogenetics, vol. 59, pp. 197-209 (Year: 2007).

Nielsen, M. and Andreatta, M., "NNAlign: a platform to construct and evaluate artificial neural network models of receptor-ligand interactions", Nucleic Acids Research, published online Apr. 12, 2017, vol. 45, pp. W344-W349 (6 pages).

Nielsen, M. and Lund, O., "NN-align. An artificial neural network-based alignment algorithm for MHC class II peptide binding prediction", BMC Bioinformatics, Sep. 18, 2009, vol. 10:296, pp. 1-10 (10 pages).

Nielsen, M. et al., "Quantitative Predictions of Peptide Binding to Any HLA-DR Molecule of Known Sequence: NetMHCIIpan", PLoS Computational Biology, Jul. 4, 2008, vol. 4(7):e1000107, pp. 1-10 (10 pages).

O'Donnell, T.J. et al., "MHCflurry 2.0: Improved Pan-Allele Prediction of MHC Class I-Presented Peptides by Incorporating Antigen Processing", Cell Systems, Jul. 22, 2020, vol. 11, pp. cover, 42-48 (15 pages).

O'Donnell, T.J. et al., "MHCflurry: Open-Source Class I MHC Binding Affinity Prediction", Cell Systems, Jul. 25, 2018, vol. 7, pp. cover, 129-132 (9 pages).

Schipper, et al., "Minimal Phenotype Panels a Method for Achieving Maximum Population Coverage with a Minimum of HLA Antigens," Human Immunology, vol. 51, pp. 95-98 (Year: 1996).

Sette et al., "Peptides and Methods for Creating Synthetic Peptides With Modulated Binding Affinity for HLA Molecules," Application for utility U.S. Appl. No. 09/226,775, filed Jan. 6, 1999-not published, abandoned (133 total pages).

Shimokawa, C. et al., "CD8+ regulatory T cells are critical in prevention of autoimmune-mediated diabetes", Nature Communications, Apr. 22, 2020, vol. 11:1922, pp. 1-9 (9 pages).

Toussaint, N. C. et al., "A Mathematical Framework for the Selection of an Optimal Set of Peptides for Epitope-Based Vaccines", PLoS Computational Biology, Dec. 26, 2008, vol. 4(12):e1000246, pp. 1-10 (10 pages).

Factoring of disease presentation type probabilities and for each presentation, probability of targets presented

| Disease | Target 1 KRAS G12D | Target 2 KRAS G12V | ... | Target m KRAS G12R |
|---|---|---|---|---|
| Presentation 1 0.032 (Pancreas) | 0.328 | 0.226 | | 0.151 |
| Presentation 2 0.082 (Colon and rectum) | 0.279 | 0.214 | | 0.093 |
| ... | | | | |
| Presentation 3 0.127 (Bronchus and lung) | 0.019 | 0.038 | | 0.000 |

FIG. 5

```
1   def merge_multi(lists):
2       values = []
3
4       # While any list in lists has elements remaining
5       while max(map(lambda l: len(l), lists)) > 0:
6           # Find list with largest value at its head.
7           cur_max = None
8           cur_max_idx = None
9           for idx, l in enumerate(lists):
10              if not l:  # List is empty.
11                  continue
12              if cur_max is None or l[0] > cur_max:
13                  cur_max = l[0]
14                  cur_max_idx = idx
15          # Pop that value from list l.
16          values.append((lists[cur_max_idx].pop(0), cur_max_idx))
17
18      return values
```

COMPOSITIONS FOR OPTIMIZED RAS PEPTIDE VACCINES

This patent disclosure contains material that is subject to copyright protection. The copyright owner has no objection to the facsimile reproduction of the patent document or the patent disclosure as it appears in the U.S. Patent and Trademark Office patent file or records, but otherwise reserves any and all copyright rights.

INCORPORATION BY REFERENCE

All documents cited herein are incorporated herein by reference in their entirety.

SEQUENCE LISTING

The instant application contains a Sequence Listing which has been submitted electronically in ASCII format and is hereby incorporated by reference in its entirety. The ASCII copy, created on Nov. 20, 2020, is named 2215269_00123US1_SL.txt and is 419,529 bytes in size.

TECHNICAL FIELD

The present invention relates generally to compositions, systems, and methods of peptide vaccines. More particularly, the present invention relates to compositions, systems, and methods of designing peptide vaccines to treat or prevent disease optimized based on predicted population immunogenicity.

BACKGROUND

The goal of a peptide vaccine is to train the immune system to recognize and expand its capacity to engage cells that display foreign peptides to improve the immune response to cancerous cells or pathogens. A peptide vaccine can also be administered to someone who is already diseased to increase their immune response to a causal cancer, other diseases, or pathogen. There exists a need for compositions, systems, and methods of peptide vaccines based on prediction of the foreign peptides that will be displayed at a later time to protect a host from cancer, other disease, or pathogen infection.

SUMMARY OF THE INVENTION

In one aspect, the invention provides for a nucleic acid sequence encoding two or more amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some embodiments, the nucleic acid sequence is an immunogenic composition. In some embodiments, the nucleic acid sequence is administered in a construct for expression in vivo. In some embodiments, the in vivo administration of the nucleic acid sequence is configured to produce one or more peptides that are displayed by an HLA class I molecule. In some embodiments, the one or more peptides is a modified or unmodified fragment of a mutated KRAS protein. In some embodiments, the mutated KRAS protein is selected from the group consisting of KRAS G12D, KRAS G12V, and KRAS G12R. In some embodiments, the nucleic acid sequence is administered in an effective amount to a subject to prevent cancer. In some embodiments, the nucleic acid sequence is administered in an effective amount to a subject to treat cancer.

In another aspect, the invention provides for an immunogenic peptide composition comprising two or more peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some embodiments, a peptide in the immunogenic peptide composition is displayed by an HLA class I molecule. In some embodiments, a peptide in the immunogenic peptide composition is a modified or unmodified fragment of a mutated KRAS protein. In some embodiments, the mutated KRAS protein is selected from the group consisting of KRAS G12D, KRAS G12V, and KRAS G12R. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic peptide composition comprises at least three peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In another aspect, the invention provides for a nucleic acid sequence encoding one or more amino acid sequences selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments, the nucleic acid sequence is an immunogenic composition. In some embodiments, the nucleic acid sequence is administered in a construct for expression in vivo. In some embodiments, the in vivo administration of the nucleic acid sequence is configured to produce one or more peptides that are displayed by an HLA class II molecule. In some embodiments, the one or more peptides is a modified fragment of a mutated KRAS protein.

In some embodiments, the mutated KRAS protein is selected from the group consisting of KRAS G12D, KRAS G12V, KRAS G12R, KRAS G12C, and KRAS G13D. In some embodiments, the nucleic acid sequence is administered in an effective amount to a subject to prevent cancer. In some embodiments, the nucleic acid sequence is administered in an effective amount to a subject to treat cancer.

In another aspect, the invention provides for an immunogenic peptide composition comprising one or more peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments, a peptide in the immunogenic peptide composition is displayed by an HLA class II molecule. In some embodiments, a peptide in the immunogenic peptide composition is a modified or unmodified fragment of a mutated KRAS protein. In some embodiments, the mutated KRAS protein is selected from the group consisting of KRAS G12D, KRAS G12V, KRAS G12R, KRAS G12C, and KRAS G13D. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic peptide composition comprises at least two peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

BRIEF DESCRIPTION OF THE DRAWINGS

The following figures depict illustrative embodiments of the invention.

FIG. 5 shows probabilities of disease presentations for pancreas, colon/rectum, and bronchus/lung and respective probabilities of target presentations for KRAS G12D, KRAS G12V, and KRAS G12R targets.

FIG. 9 shows an example Python implementation of the MergeMulti function for combined vaccine design procedures.

DETAILED DESCRIPTION

Figure 1:
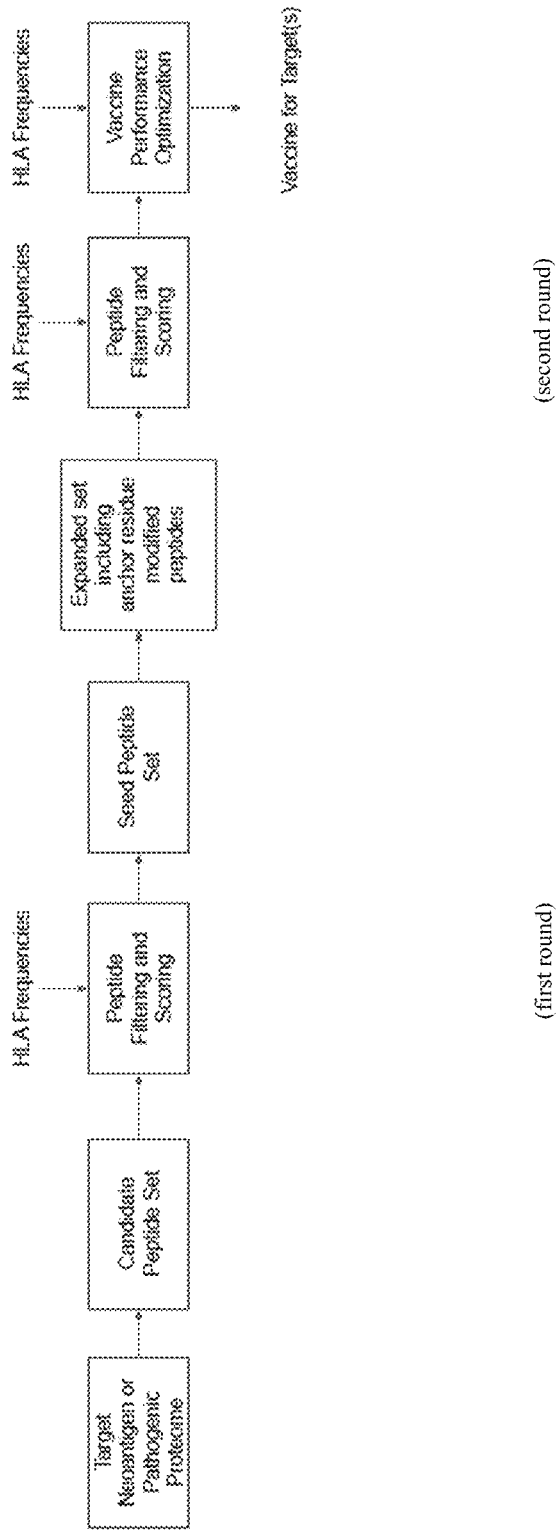
FIG. 1 is a flow chart of a vaccine optimization method.

In some embodiments, the disclosure provides for peptide vaccines that incorporate peptide sequences that will be displayed by Major Histocompatibility Complex (MHC) molecules on cells and train the immune system to recognize cancer or pathogen diseased cells. In some embodiments, a peptide vaccine is a composition that consists of one or more peptides. In some embodiments, a peptide vaccine is an mRNA or DNA construct administered for expression in vivo that encodes for one or more peptides.

Peptide display by an MHC molecule is necessary, but not sufficient, for a peptide to be immunogenic and cause the recognition of the resulting peptide-MHC complex by an individual's T cells to trigger T cell activation, expansion, and immune memory. In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) can be combined with machine learning based predictions of peptide display by an MHC molecule. In some embodiments, the MHCflurry or NetMHCpan computational methods (known in the art) are used to predict MHC class I display of a peptide by an HLA allele (see Table 1). In some embodiments, the NetMHCIIpan computational method (known in the art) is used to predict MHC class II display of a peptide by an HLA allele (see Table 2).

A peptide is displayed by an MHC molecule when it binds within the groove of the MHC molecule and is transported to the cell surface where it can be recognized by a T cell receptor. In some embodiments, a peptide that is part of the normal proteome in a healthy individual is a self-peptide, and a peptide that is not part of the normal proteome is a foreign peptide. Foreign peptides can be generated by mutations in normal self-proteins in tumor cells that create epitopes called neoantigens, or by pathogenic infections. In some embodiments, a neoantigen is any subsequence of a human protein, where the subsequence contains one or more altered amino acids or protein modifications that do not appear in a healthy individual.

For example, KRAS gene mutations are the most frequently mutated oncogenes in cancer, but they have been very difficult to treat with small molecule therapeutics. The KRAS protein is part of a signaling pathway that controls cellular growth, and point mutations in the protein can cause constitutive pathway activation and uncontrolled cell growth. Single amino acid KRAS mutations result in minor changes in protein structure, making it difficult to engineer small molecule drugs that recognize a mutant specific binding pocket and inactivate KRAS signaling. KRAS oncogenic mutations include the mutation of position 12 from glycine to aspartic acid (G12D), glycine to valine (G12V), glycine to arginine (G12R), or glycine to cystine (G12C); or the mutation of position 13 from glycine to aspartic acid (G13D). The corresponding foreign peptides contain these mutations.

A challenge for the design of peptide vaccines is the diversity of human MHC alleles that each have specific preferences for the peptide sequences they will display. The Human Leukocyte Antigen (HLA) loci, located within the MHC, encode the HLA class I and class II molecules. There are three classical class I loci (HLA-A, HLA-B, and HLA-C) and three loci that encode class II molecules (HLA-DR, HLA-DQ, and HLA-DP). An individual's HLA type describes the alleles they carry at each of these loci. Peptides of length of between about 8 and about 11 residues can bind to HLA class I (or MHC class I) molecules whereas those of length of between about 13 and about 25 bind to HLA class II (or MHC class II) molecules (Rist et al., 2013; Chicz et al., 1992). Human populations that originate from different geographies have differing frequencies of HLA alleles, and these populations exhibit linkage disequilibrium between HLA loci that result in population specific haplotype frequencies. In some embodiments, methods are disclosed for creating effective vaccines that includes consideration of the HLA allelic frequency in the target population, as well as linkage disequilibrium between HLA genes to achieve a set of peptides that is likely to be robustly displayed.

The present disclosure provides for compositions, systems, and methods of vaccine designs that produce immunity to multiple targets. In some embodiments, a target is a neoantigen protein sequence, a pathogen proteome, or any other undesired protein sequence that is non-self and is expected to be bound and displayed by an MHC molecule. When a target is present in an individual it may result in multiple peptide sequences that are displayed by a variety of HLA alleles. Therefore, in this disclosure, "foreign peptide" refers to an amino acid sequence encoding a fragment of a target protein/peptide (or a full protein/peptide), the target protein/peptide consisting of: a neoantigen protein, a pathogen proteome, or any other undesired protein that is non-self and is expected to be bound and displayed by an MHC molecule.

In some embodiments, peptide-MHC immunogenicity data or computational predictions of peptide-MHC immunogenicity can be included and combined with scores for peptide display in the methods disclosed herein. One way of combining the scores is using immunogenicity data for peptides assayed for immunogenicity in diseased or vaccinated individuals, and assigning peptides to the HLA allele that displayed them in the individual by choosing the HLA allele that computational methods predict has the highest likelihood of display. For peptides that are not experimentally assayed, computational predictions of display can be used.

Since immunogenicity may vary from individual to individual, one method to increase the probability of vaccine efficacy is to use a diverse set of foreign peptides (e.g., at least two peptides) to increase the chances that some subset of them will be immunogenic in a given individual. Prior research using mouse models has shown that most MHC displayed peptides are immunogenic, but immunogenicity varies from individual to individual as described in Croft et al. (2019). In some embodiments, experimental peptide-HLA immunogenicity data are used to determine which foreign peptides and their modifications will be effective immunogens in a vaccine.

Considerations for the design of peptide vaccines are outlined in Liu et al., Cell Systems 11, Issue 2, p. 131-146 (Liu et al., 2020) and (Liu et al., 2020b) which are incorporated by reference herein.

Certain foreign peptides may not bind with high affinity to a wide range of HLA molecules. To increase the binding of foreign peptides to HLA molecules, their amino acid composition can be altered to change one or more anchor residues or other residues. Anchor residues are amino acids that interact with an HLA molecule and have the largest influence on the affinity of a peptide for an HLA molecule. Peptides with altered anchor residues are called heteroclitic peptides. In some embodiments, heteroclitic peptides include foreign peptides with residue modifications at non-anchor positions. In some embodiments, heteroclitic peptides include foreign peptides with residue modifications that include unnatural amino acids and amino acid derivatives. Modifications to create heteroclitic peptides can improve the binding of peptides to both MHC class I and MHC class II molecules, and the modifications required can be both peptide and MHC class specific. Since peptide anchor residues face the MHC molecule groove, they are less visible than other peptide residues to T cell receptors. Thus, heteroclitic peptides have been observed to induce a T cell response where the stimulated T cells also respond to unmodified peptides. It has been observed that the use of heteroclitic peptides in a vaccine can improve a vaccine's effectiveness (Zirlik et al., 2006). In some embodiments, the immunogenicity of heteroclitic peptides are experimentally determined and their ability to activate T cells that also recognize the corresponding base (also called seed) peptide of the heteroclitic peptide is performed as is known in the art. In some embodiments, these assays of the immunogenicity and cross-reactivity of heteroclitic peptides are performed when the heteroclitic peptides are displayed by specific HLA alleles.

Peptide Vaccines to Induce Immunity to One or More Targets

In some embodiments, a method is provided for formulating peptide vaccines using a single vaccine design for a one or more targets. In some embodiments, a single target is a foreign protein with a specific mutation (e.g., KRAS G12D). In some embodiments, multiple targets can be used (e.g. both KRAS G12D and KRAS G13D).

Figure 2:
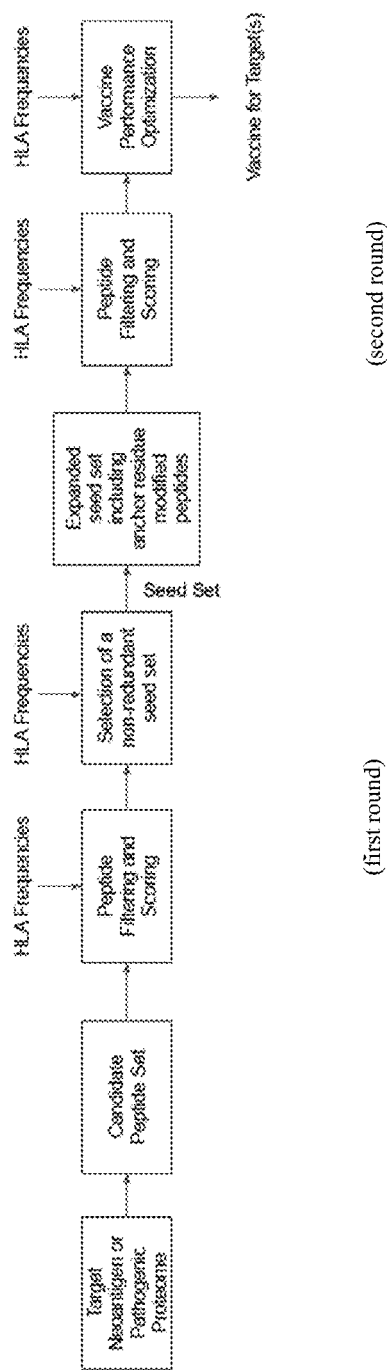
FIG. 2 is a flow chart of vaccine optimization method with seed set compression.

In some embodiments, the method includes extracting peptides to construct a candidate set from all target proteome sequences (e.g., entire KRAS G12D protein) as described in Liu et al. (2020). FIGS. 1 and 2 depict flow charts for example vaccine design methods that can be used for MHC class I or MHC class II vaccine design. In some embodiments, extracted foreign peptides are of amino acid length of between about 8 and about 10 (e.g., for MHC class I binding (Rist et al., 2013)). In some embodiments, the extracted foreign peptides presented by MHC class I molecules are longer than 10 amino acid residues, such as 11 residues (Trolle et al., 2016). In some embodiments, extracted foreign peptides are of length between about 13 and about 25 (e.g., for class II binding (Chicz et al., 1992)). In some embodiments, sliding windows of various size ranges described herein are used over the entire proteome. In some embodiments, other foreign peptide lengths for MHC class I and class II sliding windows can be utilized. In some embodiments, computational predictions of proteasomal cleavage are used to filter or select peptides in the candidate set. One computational method for predicting proteasomal cleavage is described by Nielsen et al. (2005). In some embodiments, peptide mutation rates, glycosylation, cleavage sites, or other criteria can be used to filter peptides as described in Liu et al. (2020).

As shown in FIGS. 1-2, in some embodiments, the next step of the method includes scoring the foreign peptides in the candidate set for binding to all considered HLA alleles as described in Liu et al. (2020) and Liu et al. (2020b). Scoring can be accomplished for human HLA molecules, mouse H-2 molecules, swine SLA molecules, or MHC molecules of any species for which prediction algorithms are available or can be developed. Thus, vaccines targeted at non-human species can be designed with the method. Scoring metrics can include the affinity for a foreign peptide to an HLA allele in nanomolar, eluted ligand, presentation, and other scores that can be expressed as percentile rank or any other metric. The candidate set may be further filtered to exclude peptides whose predicted binding cores do not contain a particular pathogenic or neoantigen target residue of interest or whose predicted binding cores contain the target residue in an anchor position. The candidate set may also be filtered for foreign peptides of specific lengths, such as length 9 for MHC class I, for example. In some embodiments, scoring of foreign peptides is accomplished with experimental data or a combination of experimental data and computational prediction methods.

The criteria used for scoring peptide-HLA binding during the scoring procedure can accommodate different goals during the candidate identification and vaccine design phases. For example, a foreign peptide with peptide-HLA binding affinities of 500 nM may be displayed by an individual that is diseased, but at a lower frequency than a foreign peptide with a 50 nM peptide-HLA binding affinity. Thus, during the scoring of a candidate set to qualify potential immune system targets, 500 nM or other less constrained affinity criteria than 50 nM may be utilized. During the combinatorial design phase of a vaccine, a more constrained affinity criteria may be used, such a 50 nM, to increase the probability that a vaccine peptide will be found and displayed by HLA molecules. In some embodiments, peptides are selected that have peptide-HLA binding affinities of between about 50 nM and about 500 nM. Alternatively, combined models that incorporate peptide immunogenicity can be used to qualify foreign peptides for improvement and score their modified versions for vaccine inclusion. In some embodiments, experimental observations of the immunogenicity of peptides in the context of their display by HLA alleles can be used to score peptides for vaccine inclusion. In some embodiments, computational predictions of the immunogenicity of a peptide in the context of display by HLA alleles can used for scoring such as the methods of Ogishi et al. (2019).

In some embodiments, the method further includes running the OptiVax-Robust algorithm as described in Liu et al. (2020) using the HLA haplotype frequencies of a population on the scored candidate set to construct a seed set (also referred to as base set herein) of foreign peptides (FIG. 2). In some embodiments, HLA diplotype frequencies can be provided to OptiVax. OptiVax-Robust includes algorithms to eliminate peptide redundancy that arises from the sliding window approach with varying window sizes, but other redundancy elimination measures can be used to enforce minimum edit distance constraints between foreign peptides in the candidate set. The size of the seed set is determined by a point of diminishing returns of population coverage as a function of the number of foreign peptides in the seed set. Other criteria can also be used, including a minimum number of vaccine foreign peptides, maximum number of vaccine foreign peptides, and desired predicted population coverage. One alternative criterion is a minimum number of expected peptide-HLA hits in each individual, where a peptide-HLA hit is the potential immunogenic display of a peptide by a single HLA allele as described as in Liu et al. (2020b). In alternate embodiments, the method further includes running the OptiVax-Unlinked algorithm as described in Liu et al. (2020) instead of OptiVax-Robust.

The OptiVax-Robust method uses binary predictions of foreign peptide binding to HLA alleles, and these binary predictions can be generated as described in Liu et al. (2020). The OptiVax-Unlinked method uses the probability of foreign peptide binding to HLA alleles and can be generated as described in Liu et al. (2020). Either method can be used for the purposes described herein, and thus we will the term "OptiVax" refers to either the Robust or Unlinked method. In some embodiments, the observed probability of peptide-HLA immunogenicity in experimental assays can be used as the probability of peptide-HLA binding in EvalVax-Unlinked and OptiVax-Unlinked. In some embodiments, the HLA haplotype or HLA allele frequencies of a population provided to OptiVax for vaccine design describe the world's population. In alternative embodiments, the HLA haplotype or HLA allele frequencies of a population provided to OptiVax for vaccine design are specific to a geographic region. In alternative embodiments, the HLA haplotype or HLA allele frequencies of a population provided to OptiVax for vaccine design are specific to an ancestry. In alternative embodiments, the HLA haplotype or HLA allele frequencies of a population provided to OptiVax for vaccine design are specific to a race. In alternative embodiments, the HLA haplotype or HLA allele frequencies of a population provided to OptiVax for vaccine design are specific to individuals with risk factors such as genetic indicators of risk, age, exposure to chemicals, alcohol use, chronic inflammation, diet, hormones, immunosuppression, infectious agents, obesity, radiation, sunlight, or tobacco use. In alternative embodiments, the HLA haplotype or HLA allele frequencies of a population provided to OptiVax for vaccine design are specific to individuals that carry certain HLA alleles. In alternative embodiments, the HLA diplotypes provided to OptiVax for vaccine design describe a single individual, and are used to design an individualized vaccine.

In some embodiments, the seed set of foreign peptides that results from OptiVax application to the candidate set of target peptides describes a set of unmodified foreign peptides that represent a possible compact vaccine design (Seed Set in FIG. 2). In some embodiments, the seed set is based upon filtering candidate peptides by predicted or observed affinity or immunogenicity with respect to HLA molecules (Seed Set in FIG. 1). However, to improve the display of the foreign peptides in a wide range of HLA haplotypes as possible, some embodiments include modifications of the seed (or base) set. In some embodiments, experimental assays can be used to ensure that a modified seed (or base) peptide activates T cells that also recognize the seed peptide.

For a given foreign peptide, the optimal anchor residue selection may depend upon the HLA allele that is binding to and displaying the foreign peptide and the class of the HLA allele (MHC class I or class II). A seed peptide set can become an expanded set by including anchor residue modified peptides of either MHC class I or II peptides (FIGS. 1-2). Thus, one aspect of vaccine design is considering how to select a limited set of heteroclitic peptides that derive from the same foreign peptide for vaccine inclusion given that different heteroclitic peptides will have different and potentially overlapping population coverages.

In some embodiments, all possible anchor modifications for each base set foreign peptide are considered. There are two anchor residues in peptides bound by MHC class I molecules, typically at positions 2 and 9 for 9-mer peptides. At each anchor position, 20 possible amino acids are attempted in order to select the best heteroclitic peptides. Thus, for MHC class I binding, 400 (i.e., 20 amino acids by 2 positions=$20^2$) minus 1 heteroclitic peptides are generated for each base foreign peptide. There are four anchor residues in peptides bound by MHC class II molecules, typically at positions 1, 4, 6, and 9 of the 9-mer binding core. Thus, for MHC class II binding there are 160,000 (i.e., 20 amino acids by 4 positions=$20^4$) minus 1 heteroclitic peptides generated for each base foreign peptide. Other methods, including Bayesian optimization, can be used to select optimal anchor residues to create heteroclitic peptides from each seed (or base) set peptide. Other methods are presented in "Machine learning optimization of peptides for presentation by class II MHCs" by Dai et al. (2020), incorporated in its entirety herein. In some embodiments, the anchor positions are determined by the HLA allele that presents a peptide, and thus the set of heteroclitic peptides includes for each set of HLA specific anchor positions, all possible anchor modifications.

In some embodiments, for all of the foreign peptides in the seed set, new peptide sequences with all possible anchor residue modifications (e.g., MHC class I or class II) are created resulting in a new heteroclitic base set (Expanded set in FIGS. 1-2) that includes all of the modifications. In some embodiments, the heteroclitic base set (Expanded set in FIGS. 1-2) also includes the original seed (or base) set (Seed Peptide Set in FIGS. 1-2). In some embodiments, the heteroclitic base set includes amino acid substitutions or non-natural amino acid analogs at non-anchor residues. The heteroclitic base set is scored for HLA affinity or other metrics as described herein (another round of Peptide Filtering and Scoring as shown in FIGS. 1-2). The scoring predictions may be further updated for pairs of heteroclitic peptide and HLA allele, eliminating pairs where a heteroclitic peptide is predicted to be displayed by an allele but the seed (or base) peptide from which it was derived is not predicted to be displayed by the allele. The scoring predictions may also be filtered to ensure that predicted binding cores of the heteroclitic peptide displayed by a particular HLA allele align exactly in position with the binding cores of the respective seed (or base) set foreign peptide for that HLA allele. In some embodiments the scoring predictions are filtered for an HLA allele to ensure that the heteroclitic peptides considered for that HLA allele are only modified at anchor positions determined by that HLA allele. In some embodiments, heteroclitic peptides are included in experimental assays such as MIRA (Klinger et al., 2015) to determine their immunogenicity with respect to specific HLA alleles. In some embodiments, the methods of Liu et al. (2020b), can be used to incorporate MIRA data for heteroclitic peptides into a model of peptide-HLA immunogenicity. In some embodiments, the immunogenicity of heteroclitic peptides are experimentally determined and their ability to activate T cells that also recognize the corresponding seed (or base) peptide of the heteroclitic peptide is performed as is known in the art. In some embodiments, these assays of the immunogenicity and cross-reactivity of heteroclitic peptides are performed when the heteroclitic peptides are displayed by specific HLA alleles. In some embodiments, computational predictions of the immunogenicity of a heteroclitic peptide in the context of display by HLA alleles can used for scoring such as the methods of Ogishi et al. (2019).

In some embodiments, the next step involves inputting heteroclitic base set (also referred to as Expanded set as shown in FIGS. 1-2) to OptiVax to select a compact set of vaccine peptides that maximizes vaccine performance (Vaccine Performance Optimization; FIGS. 1-2). Vaccine performance is the population coverage of a vaccine, or the expected number peptide-HLA hits produced by a vaccine, or a function of population coverage and expected number of peptide-HLA hits desired. In some embodiments, the vaccine immunogenicity metric is a metric that describes the overall immunogenic properties of a vaccine with two or more peptides In some embodiments, the methods described herein are included for running OptiVax. In some embodiments, population coverage means the proportion of a subject population that presents one or more immunogenic peptides that activate T cells responsive to a seed foreign peptide. The metric of population coverage is computed using the HLA haplotype frequency in a given population such as a representative human population. In some embodiments, the metric of population coverage is computed using marginal HLA frequencies in a population. Maximizing population coverage means selecting a foreign peptide set that collectively results in the greatest fraction of the population that has at least a minimum number (e.g., 1, 2, 3, 4, 5, 6, 7, or 8) of immunogenic peptide-HLA bindings based on proportions of HLA haplotypes in a given population (e.g., representative healthy or diseased human population). In some embodiments, this process includes the OptiVax selection of heteroclitic peptides (as described in this disclosure) that activate T cells that respond to their corresponding seed (or base) peptide and the heteroclitic base peptides to improve population coverage. In some embodiments, the seed (or base) foreign peptides are always included in the final vaccine design to guard against the possibility that heteroclitic peptides will not produce immunity that reacts with the native seed (or base) foreign peptides. In some embodiments, peptides are only considered as candidates for a vaccine design if they have been observed to be immunogenic in clinical data or animal models.

In some embodiments, a candidate vaccine peptide is eliminated from vaccine inclusion if it activates T cells that recognize self-peptides (e.g., this can be achieved at the first and/or second round of Peptide Filtering and Sorting as shown in FIGS. 1-2). Testing a vaccine peptide for its ability to activate T cells that recognize self-peptides can be experimentally accomplished by the vaccination of animal models followed by ELISPOT or other immunogenicity assay or with human tissue protocols. In both cases, models with HLA alleles that present the vaccine peptide are used. In some embodiments, human primary blood mononuclear cells (PBMCs) are stimulated with a vaccine peptide, the T cells are allowed to grow, and then T cell activation with a self-peptide is assayed as described in Tapia-Calle et al. (2019) or other methods as known in the art. In some embodiments, computational predictions of the ability of a peptide to activate T cells that also recognize self-peptides can be utilized. These predictions can be based upon the modeling of the outward facing residues from the peptide-HLA complex and their interactions with other peptide residues. In some embodiments, a candidate vaccine peptide is eliminated from vaccine inclusion or experimentally tested for cross-reactivity if it is predicted to activate T cells that also recognize self-peptides based upon the structural similarity of the peptide-MHC complex of the candidate peptide and the peptide-MHC complex of a self-peptide. One method for the prediction of peptide-MHC structure is described by Park et al. (2013).

In some embodiments, a candidate heteroclitic vaccine peptide is eliminated from vaccine inclusion if it does not activate T cells that recognize its corresponding seed foreign peptide (second round of Peptide Filtering and Scoring, FIGS. 1-2). Testing a candidate heteroclitic peptide for its ability to activate T cells that recognize its corresponding seed (or base) foreign peptide can be experimentally accomplished by the vaccination of animal models followed by ELISPOT or other immunogenicity assay or with human tissue protocols. In both cases, models with HLA alleles that present the heteroclitic peptide are used. In some embodiments, human PBMCs are stimulated with the heteroclitic peptide, the T cells are allowed to grow, and then T cell activation with the seed (or base) foreign peptide is assayed as described in Tapia-Calle et al. (2019) or using other methods known in the art. In some embodiments, computational predictions of the ability of a heteroclitic peptide to activate T cells that also recognize the corresponding seed (or base) foreign peptide can be utilized. These predictions can be based upon the modeling of the outward facing residues from the peptide-HLA complex and their interactions with other peptide residues. In some embodiments, the structural similarity of the peptide-MHC complex of a heteroclitic peptide and the peptide-MHC complex of the corresponding seed (or base) foreign is used to qualify heteroclitic peptides for vaccine inclusion or to require experimental immunogenicity testing before vaccine inclusion.

Figure 3:
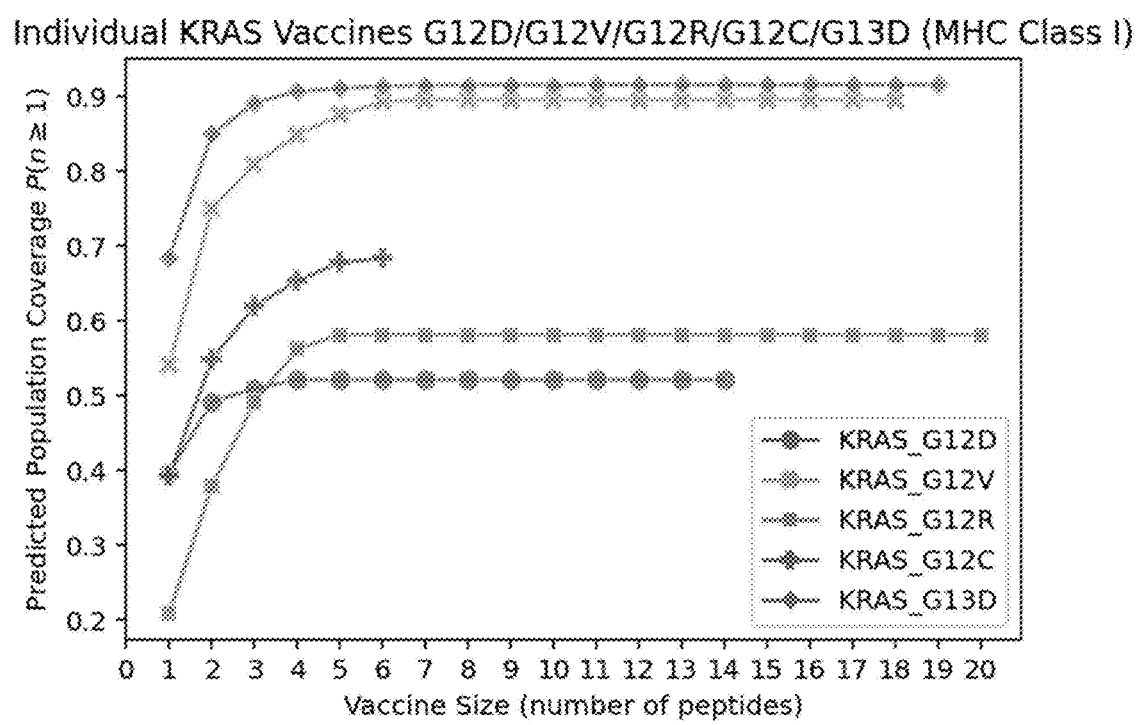
FIG. 3 shows predicted population coverage for single target MHC class I vaccines by vaccine size for KRAS G12D, KRAS G12V, KRAS G12R, KRAS G12C, and KRAS G13D targets.
Figure 4:
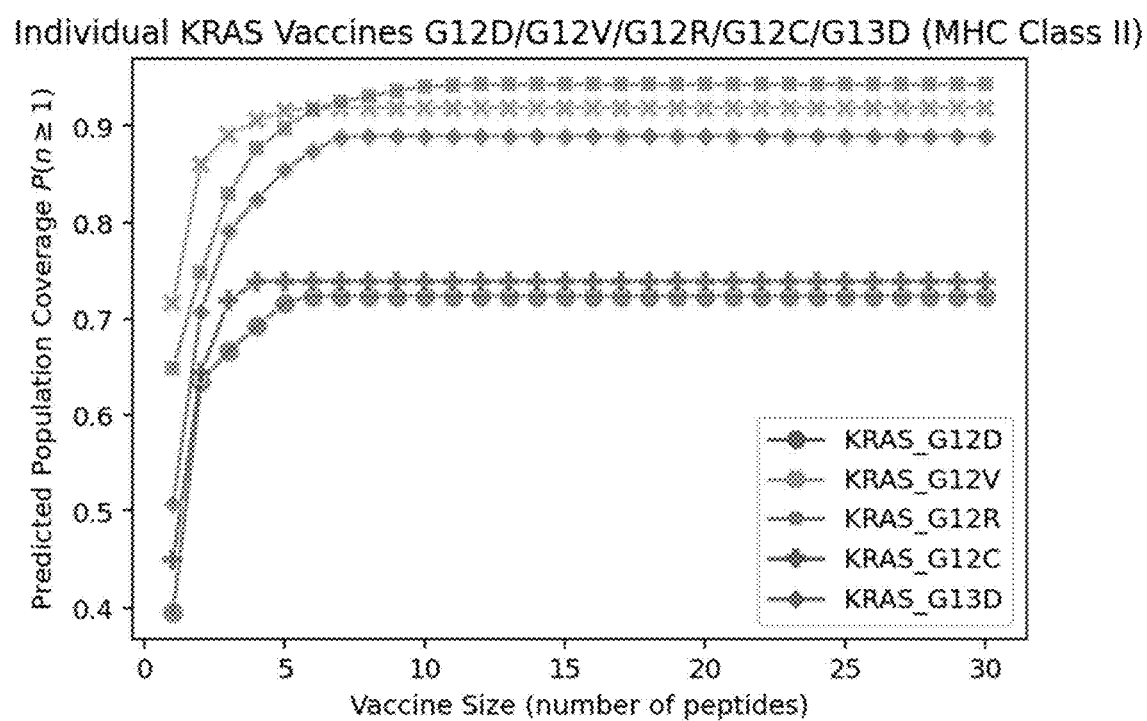
FIG. 4 shows predicted population coverage for single target MHC class II vaccines by vaccine size for KRAS G12D, KRAS G12V, KRAS G12R, KRAS G12C, and KRAS G13D targets.

FIG. 3 (MHC class I) and FIG. 4 (MHC class II) show the predicted population coverage of OptiVax-Robust selected single target-specific vaccines with differing number of peptides designed for the KRAS mutations G12D, G12V, G12R, G12C, and G13D. FIGS. 4-5 show that as the number of peptides increases for a vaccine, its predicted population coverage increases. The population coverage shown in FIGS. 4-5 are of those individuals that have the specific mutation that the vaccine is designed to cover. An increase in peptide count will also typically cause the average number of peptide-HLA hits in each individual to increase in the population.

OptiVax can be used to design a vaccine to maximize the fraction/proportion of the population whose HLA molecules are predicted to bind to and display at least p peptides from the vaccine. In some embodiments, this prediction includes experimental immunogenicity data to directly predict at least p peptides will be immunogenic. The number p is input to OptiVax, and OptiVax can be run multiple times with varying values for p to obtain a predicted optimal foreign peptide set for different peptide counts p. Larger values of p will increase the redundancy of a vaccine at the cost of more peptides to achieve a desired population coverage. In some embodiments, it may not be possible to achieve a given population coverage given a specific heteroclitic base set. In some embodiments, the number p is a function of the desired size of a vaccine.

The methods described herein can be used to design separate vaccine formulations for MHC class I and class II based immunity.

In some embodiments, this procedure is used to create a vaccine for an individual. In some embodiments, the foreign peptides present in the individual are determined by sequencing the individual's tumor RNA or DNA, and identifying mutations that produce foreign peptides. One embodiment of this is described in U.S. Ser. No. 10/738,355B2. In some embodiments, peptide sequencing methods are used to identify foreign peptides in the individual. One embodiment of this is described in US20110257890A1. In some embodiments, the foreign peptides used for the individual's vaccine are selected when a foreign peptide or foreign peptide encoding RNA observed in a specimen from the individual is present at a predetermined level. The foreign peptides in the individual are used to construct a vaccine as described in the disclosure herein. For vaccine design OptiVax is provided a diplotype comprising the HLA type of the individual. In an alternative embodiment, the HLA type of an individual is separated into multiple diplotypes with frequencies that sum to one, where each diplotype comprises one or more HLA alleles from the individual and a notation that the other allele positions should not be evaluated. The use of multiple diplotypes will cause OptiVax's objective function to increase the chance that immunogenic peptides will be displayed by all of the constructed diplotypes.

Figure 10:
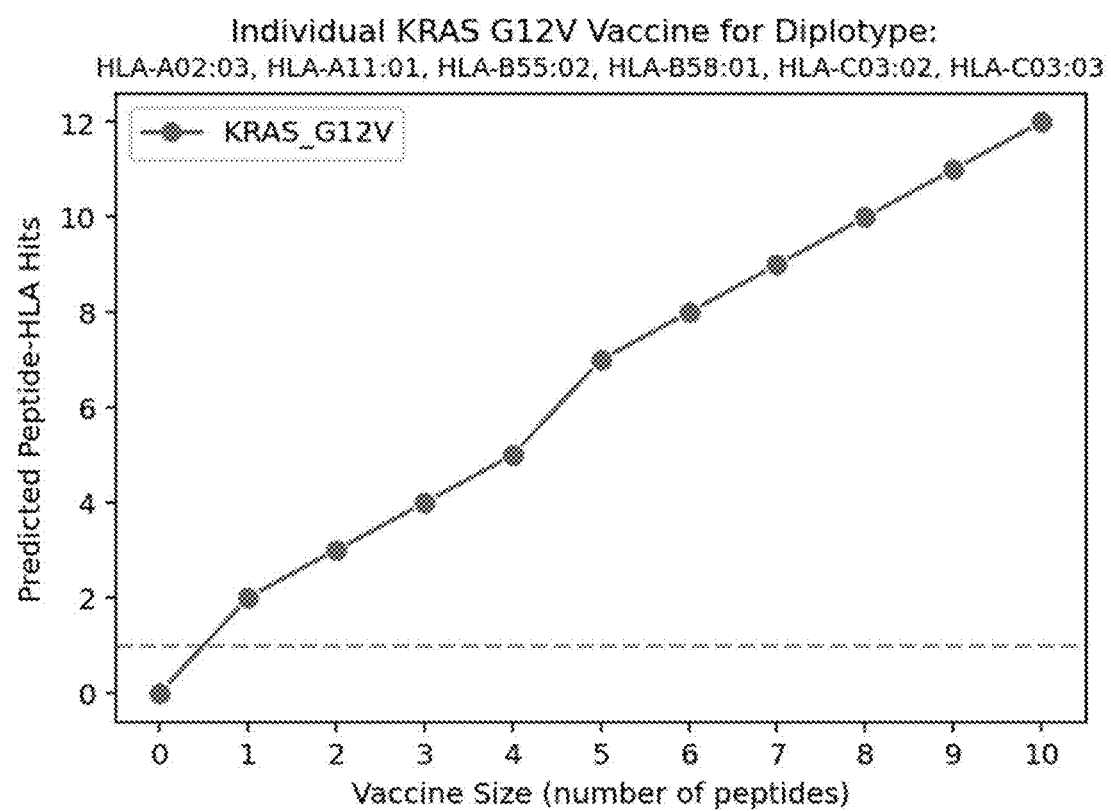
FIG. 10 shows predicated peptide-HLA hits by vaccine size for a KRAS G12V vaccine for the HLA diplotype HLA-A02:03, HLA-A11:01, HLA-B55:02, HLA-B58:01, HLA C03:02, HLA-C03:03.

FIG. 10 shows the vaccine performance (predicted number of peptide-HLA hits) of ten example G12V MHC class I vaccines for a single individual with the MHC class I HLA diplotype HLA-A02:03, HLA-A11:01, HLA-B55:02, HLA-B58:01, HLA-C03:02, HLA-C03:03. OptiVax was used to design ten G12V MHC class I vaccines for this HLA diplotype with peptide counts ranging from 1 to 10. For the results in FIG. 10, OptiVax was run with six synthetic diplotypes, each equally weighted, each with one HLA allele from the individual's HLA diplotype, and the other allele positions marked to not be evaluated. The 10 peptide vaccine in FIG. 10 comprises SEQ ID NO: 3 (GAVGVGKSL), SEQ ID NO: 4 (LMVVGAVGV), SEQ ID NO: 7 (VVGAVGVGK), SEQ ID NO: 14 (GPVGVGKSV), SEQ ID NO: 69 (LMVVGAVGI), SEQ ID NO: 72 (LMVVGAVGL), SEQ ID NO: 131 (GAVGVGKSM), SEQ ID NO: 138 (GPVGVGKSA), SEQ ID NO: 142 (VTGAVGVGK), and SEQ ID NO: 198 (VAGAVGVGM). Two peptides, SEQ ID NO: 3 (GAVGVGKSL) and SEQ ID NO: 131 (GAVGVGKSM), are predicted to bind two of the HLA alleles with an affinity of 50 nM or less.

MHC Class I Vaccine Design Procedure

In some embodiments, MHC class I vaccine design procedures consist of the following computations steps.

In some embodiments, the inputs for the computation are:

$P_{1...n}$: Peptide sequence (length n) containing the neoantigen or pathogenic target(s) of interest (e.g., KRAS G12D, KRAS G12V, KRAS G12R, KRAS G12C, KRAS G13D). $P_i$ denotes the amino acid at position i.

t: Position of target mutation in P, $t \in [1, \ldots, n]$ (e.g., t=12 for KRAS G12D).

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\mathcal{H}$: Set of HLA alleles (for HLA-A, HLA-B, HLA-C loci)

F: $\mathcal{H}^3 \rightarrow \mathbb{R}$: Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes $P(n \geq 1)$ population coverage).

In some embodiments, Peptide-HLA Scoring Functions used are:

ScorePotential: $P \times \mathcal{H} \to \mathbb{R}$: Scoring function mapping a (peptide, HLA allele) pair to a prediction of peptide-HLA display. If predicted affinity $\leq \tau_1$, then returns 1, else returns 0. Options include MHCflurry, NetMHCpan, PUFFIN, ensembles, or alternative metrics or software may be used, including models calibrated against immunogenicity data.

ScoreDisplay: $P \times \mathcal{H} \to \mathbb{R}$: Scoring function mapping a (peptide, HLA allele) pair to a prediction of peptide-HLA display. If predicted affinity $\leq \tau_2$, then returns 1, else returns 0. Options include MHCflurry, NetMHCpan, PUFFIN, ensembles, or alternative metrics or software may be used, including models calibrated against immunogenicity data.

Next, from the seed protein sequence (P), a set $\mathcal{P}$ of windowed native peptides spanning the protein sequence(s) is constructed. In some embodiments, 9-mers are produced, but this process can be performed with any desired window lengths and the resulting peptide sets combined.

$$\mathcal{P} = \{P_{j\ldots j+8} | j \in [t-8, \ldots, t], j \neq \{t-7, t\}\}$$

The second condition $j \neq \{t-\text{md } 7, t\}$ excludes peptides where the mutation at t is in positions P2 or P9 of the windowed 9-mer peptide (i.e., the anchor positions).

Next, each peptide sequence in $\mathcal{P}$ is scored against all HLA alleles in $\mathcal{H}$ for potential presentation using ScorePotential (with threshold $\tau_1 = 500$ nM) and store results in a $|\mathcal{P}| \times |\mathcal{H}|$ matrix S:

$$S[p,h] = \text{ScorePotential}(p,h) \forall p \in \mathcal{P}, h \in \mathcal{H}$$

Note that S is a binary matrix where 1 indicates the HLA is predicted to potentially present the peptide, and 0 indicates no potential presentation.

Define base set of peptides $B \subseteq \mathcal{P}$:

$$B = \{p \in \mathcal{P} | \exists h \text{ s.t.} S[p,h]=1\}$$

Thus, B contains the native peptides that are predicted to be potentially presented by at least 1 HLA.

Create a Set of all Heteroclitic Peptides B' Stemming from Peptides in B:

$$B' = \bigcup_{b \in B} \text{ANCHOR-MODIFIED}(b)$$

where Anchor-Modified(b) returns a set of all 399 anchor-modified peptides stemming from b (with all possible modifications to the amino acids at P2 and P9).

Next, all heteroclitic candidate peptides in B' are scored against all HLA alleles in $\mathcal{H}$ for predicted display using ScoreDisplay (with threshold T2=50 nM), and store results in binary $|B'| \times |\mathcal{H}|$ matrix $S_1'$:

$$S_1'[b',h] = \text{ScoreDisplay}(b',h) \forall b' \in B', h \in \mathcal{H}$$

Next, an updated scoring matrix $S_2'$ is computed for heteroclitic peptides conditioned on the potential presentation of the corresponding base peptides by each HLA:

$$S_2'[b', h] = \begin{cases} S_1'[b', h], & \text{if } S[b, h] = 1 \\ 0, & \text{otherwise} \end{cases} \forall b' \in B', h \in \mathcal{H}$$

where each heteroclitic peptide $b' \in B'$ is a mutation of base peptide $b \in B$. This condition enforces that if h was not predicted to potentially present b, then all heteroclitic peptides b' derived from b will not be displayed by h (even if h would otherwise be predicted to display b').

In some embodiments, OptiVax-Robust is used to design a final peptide set from the union of base peptides and heteroclitic peptides $B \cup B'$ (with corresponding scoring matrices S and $S_2'$ for B and B', respectively). Let $\mathcal{V}_k$ denote the compact set of vaccine peptides output by OptiVax containing k peptides. Note that $\mathcal{V}_{k+1}$ is not necessarily a superset of $\mathcal{V}_k$. (In alternate embodiments, OptiVax can be used to augment the base set B with peptides from B' using scoring matrix $S_2'$ to return set $\mathcal{A}_k$, and the final vaccine set $\mathcal{V}_{k+|B|}$ consists of peptides $B \cup \mathcal{A}_k$.)

In some embodiments, this procedure is repeated independently for each target of interest, and the resulting independent vaccine sets can be merged into a combined vaccine as described below.

MHC Class II Vaccine Design Procedure

In some embodiments, MHC class II vaccine design procedures consist of the following computations steps.

In some embodiments, the inputs for the computation are:

$P_{1 \ldots n}$: Peptide sequence(s) (length n) containing the neoantigen(s) of interest (e.g., KRAS G12D, KRAS G12V, KRAS G12R, KRAS G12C, KRAS G13D). $P_i$ denotes the amino acid at position i.

t: Position of target mutation in P, $t \in [1, \ldots, n]$ (e.g., t=12 for KRAS G12D).

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\mathcal{H}$: Set of HLA alleles (for HLA-DR, HLA-DQ, HLA-DP loci)

F: $\mathcal{H}^3 \to \mathbb{R}$: Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes $P(n \geq 1)$ population coverage).

In some embodiments, Peptide-HLA Scoring Functions used are:

ScorePotential: $P \times \mathcal{H} \to \mathbb{R}$: Scoring function mapping a (peptide, HLA allele) pair to a prediction of peptide-HLA display. If predicted affinity $\leq \tau_1$, then returns 1, else returns 0.

Options include NetMHCIIpan, PUFFIN, ensembles, or alternative metrics or software may be used, including models calibrated against immunogenicity data.

ScoreDisplay: $P \times \mathcal{H} \to \mathbb{R}$: Scoring function mapping a (peptide, HLA allele) pair to a prediction of peptide-HLA display. If predicted affinity $\leq \tau_2$, then returns 1, else returns 0. Options include NetMHCIIpan, PUFFIN, ensembles, or alternative metrics or software may be used, including models calibrated against immunogenicity data.

FindCore: $P \times \mathcal{H} \to [1, \ldots, n]$: Function mapping a (peptide, HLA allele) pair to a prediction of the 9-mer binding core. The core may be specified as the offset position (index) into the peptide where the core begins.

Next, from the seed protein sequence (P), a set $\mathcal{P}$ of peptides spanning the protein sequence are constructed. Here, we extract all windowed peptides of length 13-25 spanning the target mutation, but this process can be performed using any desired window lengths (e.g., only 15-mers).

$$\mathcal{P} = \bigcup_{k \in [13, \ldots, 25]} \mathcal{P}_k$$

$$\mathcal{P}_k = \{\mathcal{P}_{j \ldots j+(k-1)} \mid j \in [t-(k-1), \ldots, t]\}$$

where $\mathcal{P}_k$ contains all sliding windows of length k, which are combined to form $\mathcal{P}$. Note that here (unlike MHC class I), no peptides are excluded based on binding core or anchor residue positions (for MHC class II, filtering is performed in Paragraph 0063).

Next, each peptide sequence in P is scored against all HLA alleles in $\mathcal{H}$ for potential presentation using SCOREPOTENTIAL (with threshold $\tau_1=500$ nM) and store results in a $|\mathcal{P}| \times |\mathcal{H}|$ matrix $S_1$:

$$S_1[p,h] = \text{ScorePotential}(p,h) \forall p \in \mathcal{P}, h \in \mathcal{H}$$

Note that $S_1$ is a binary matrix where 1 indicates the HLA is predicted to potentially present the peptide, and 0 indicates no potential presentation.

For each (peptide, HLA allele) pair (p, h), identify/predict the 9-mer binding core using FINDCORE. The predicted binding core is recorded in a matrix C:

$$C[p,h] = \text{FindCore}(p,h) \forall p \in \mathcal{P}, h \in \mathcal{H}$$

Next, an updated scoring matrix $S_2$ is computed for native peptides in $\mathcal{P}$:

$$S_2[p, h] = \begin{cases} S_1[p, h], & \text{if } C[p, h] \text{ specifies } P_t \text{ at a non-anchor position inside core} \\ 0, & \text{otherwise} \end{cases}$$
$$\forall p \in \mathcal{P}, h \in \mathcal{H}$$

where $P_t$ is the target residue of interest (e.g., the mutation site of KRAS G12D). This condition enforces the target residue to fall within the binding core at a non-anchor position for all (peptide, HLA allele) pairs with non-zero scores in $S_2$, and allows the binding core to vary by allele per peptide (as the binding cores of a particular peptide may differ based on the HLA allele presenting the peptide). Thus, for each pair (p, h), if the predicted binding core C[p, h] specifies the target residue $P_t$ at an anchor position (P1, P4, P6, or P9 of the 9-mer core), or if $P_t$ is not contained within the binding core, then $S_2[p, h]=0$. In an alternate embodiment, $P_t$ can be located outside of the core or inside the core in a non-anchor position.

Next, OptiVax-Robust is run with peptides $\mathcal{P}$ and scoring matrix $S_2$ to identify a non-redundant base set of peptides $B \subseteq \mathcal{P}$. (In alternate embodiments, B can be chosen as the entire set $\mathcal{P}$ rather than identifying a non-redundant base set.)

Next, a set of all heteroclitic peptides B' is created stemming from peptides in B:

$$B' = \bigcup_{b \in \cup B} \{\text{ANCHOR-MODIFIED}(b, c) \forall c \mid \exists h \text{ s.t. } S_2[b, h] = 1\}$$

where ANCHOR-MODIFIED(b,c) returns a set of all $20^4 - 1$ anchor-modified peptides stemming from b with all possible modifications to the amino acids at P1, P4, P6, and P9 of the 9-mer binding core c. Thus, for each base peptide b, the heteroclitic set B' contains all anchor-modified peptides b' with modifications to all unique cores of b identified for any HLA alleles that potentially present b with a valid core position as indicated by scoring matrix $S_2$.

Next, all heteroclitic candidate peptides in B' are scored against all HLA alleles in $\mathcal{H}$ for predicted display using SCOREDISPLAY (with threshold $\tau_2=50$ nM), and store results in binary $|B'| \times |\mathcal{H}|$ matrix $S_1'$:

$$S_1'[b',h] = \text{ScoreDisplay}(b',h) \forall b' \in B', h \in \mathcal{H}$$

For each (heteroclitic peptide, HLA allele) pair (b',h), identify/predict the 9-mer binding core using FINDCORE. The predicted binding core is recorded in a matrix C':

$$C'[b',h] = \text{FindCore}(b',h) \forall b' \in B', h \in \mathcal{H}$$

An updated scoring matrix $S_2'$ is computed for heteroclitic peptides conditioned on the identified binding cores of a heteroclitic and base peptides occurring at the same offset by a particular HLA:

$$S_2'[b', h] = \begin{cases} S_1'[b', h], & \text{if } C'[b', h] = C[b, h] \\ 0, & \text{otherwise} \end{cases} \forall b' \in B', h \in \mathcal{H}$$

where each heteroclitic peptide $b' \in B'$ is a mutation of base peptide $b \in B$. This condition enforces the binding core of the heteroclitic peptide b' to be at the same relative position as the base peptide b, and, implicitly, enforces that the target residue $P_t$ still falls in a non-anchor position within the 9-mer binding core (Step 3).

An updated scoring matrix $S_3'$ is computed for heteroclitic peptides conditioned on the potential presentation of the corresponding base peptides by each HLA:

$$S_3'[b', h] = \begin{cases} S_2'[b', h], & \text{if } S[b, h] = 1 \\ 0, & \text{otherwise} \end{cases} \forall b' \in B', h \in \mathcal{H}$$

where each heteroclitic peptide $b' \in B'$ is a mutation of base peptide $b \in B$. This condition enforces that if h was not predicted to display b, then all heteroclitic peptides b' derived from b will not be displayed by h (even if h would otherwise be predicted to display b').

OptiVax-Robust is used to design a final peptide set from the union of base peptides and heteroclitic peptides $B \cup B'$ (with corresponding scoring matrices $S_2$ and $S_3'$ for B and B', respectively). Let $\mathcal{V}_k$ denote the compact set of vaccine peptides output by OptiVax containing k peptides. Note that $\mathcal{V}_{k+1}$ is not necessarily a superset of $\mathcal{V}_k$. (In alternate embodiments, OptiVax can be used to augment the base set B with peptides from B' using scoring matrix $S_2'$ to return set $\mathcal{A}_k$, and the final vaccine set $\mathcal{V}_{k+|B|}$ consists of peptides $B \cup \mathcal{A}_k$.)

In some embodiments, this procedure is repeated independently for each single target of interest, and the resulting independent vaccine sets can be merged into a combined vaccine as described below.

Methods for Combining Multiple Vaccines

The above described methods will produce an optimized foreign peptide set for one or more targets. In some embodiments, a method is provided for designing separate vaccines for MHC class I and class II based immunity for multiple targets (e.g., two or more targets such as KARS G12D and KRAS G12V).

In some embodiments, a method is disclosed for producing a combined peptide vaccine for multiple targets by using a table of presentations for a disease that is based upon empirical data from sources such as the Cancer Genome Atlas (TCGA). FIG. 5 shows one embodiment for factoring disease presentation type probabilities (pancreatic cancer, colon/rectum cancer, and bronchus/lung cancer) by probability, for each disease presentation, of target presented for various KRAS mutation targets (KRAS G12D, KRAS G12V, and KRAS G12R). A presentation is a unique set of targets that are presented by one form of a disease (e.g., distinct type of cancer as shown in FIG. 5). For each presentation, FIG. 5 shows an example of the probability of that presentation, and the probability that a given target is observed. For a given presentation, there can be one or more targets, each having a probability. In some embodiments, the method for multi-target vaccine design will allocate peptide resources for inducing disease immunity based on the presentation and respective target probabilities as shown in FIG. 5, for example. In some embodiments, presentations correspond to the prevalence of targets in different human populations or different risk groups. The probability of a target in a population is computed by summing for each possible presentation the probability of that presentation times the probability of the target in that presentation.

Figure 6:
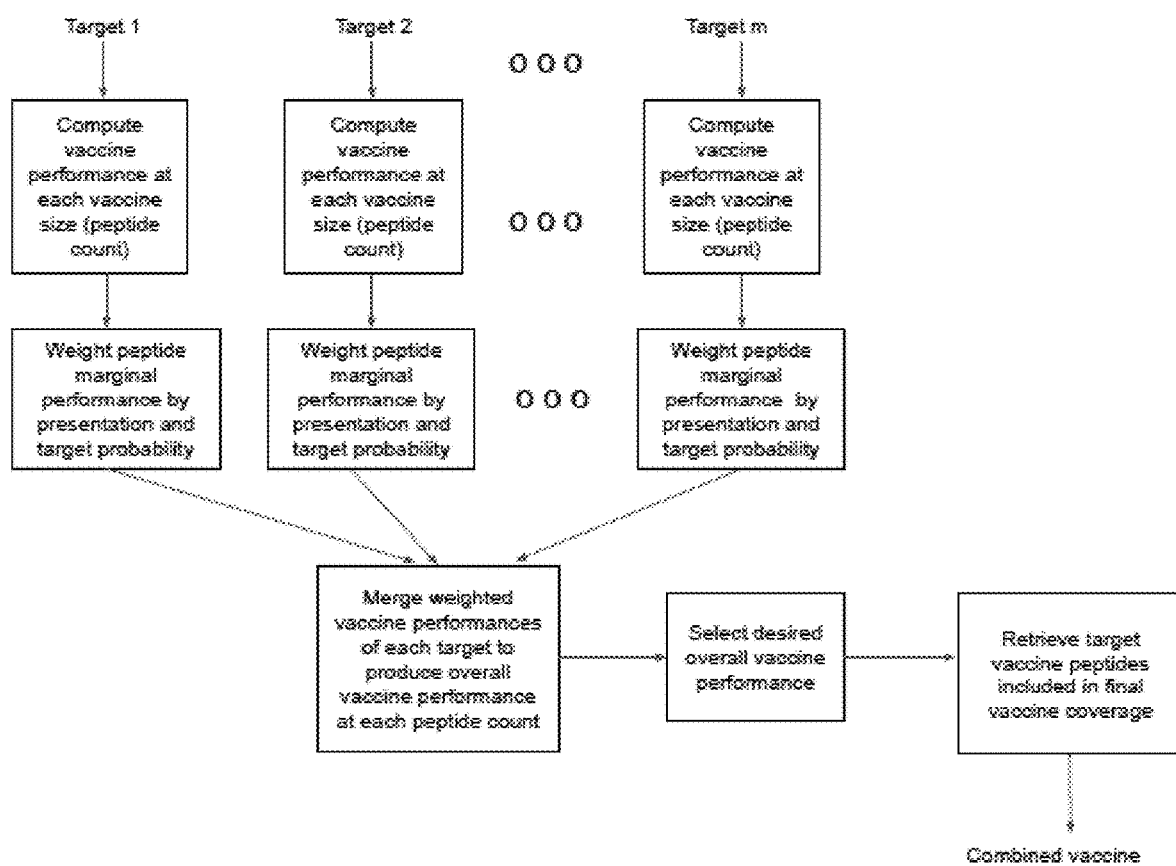
FIG. 6 is a flow chart for multiple target (combined) vaccine optimization methods.

Referring to FIG. 6, in some embodiments, the method first includes designing an individual peptide vaccine for each target to create a combined vaccine design for multiple targets. This initially results in sets of target-specific vaccine designs. In some embodiments, the marginal vaccine performance of each target-specific vaccine at size k is defined by vaccine performance at size k minus the vaccine performance of the vaccine at size k minus one (see FIGS. 3-4). The composition of a vaccine may change as the number of peptides used in the vaccine increases, and thus for computing contributions to a combined vaccine the marginal vaccine performance of each target-specific vaccine is used instead of a specific set of peptides.

In some embodiments, the weighted marginal vaccine performance of a target-specific vaccine design for each target specific vaccine size is computed as shown in FIG. 6. For a given target specific vaccine size, its weighted vaccine performance is computed by multiplying its vaccine performance times the probability of the target in the population (e.g., by using values as shown in FIG. 5). The marginal weighted vaccine performance for a target specific vaccine is its weighted coverage at size k minus its coverage a size k minus one (e.g., see FIGS. 3-4). The marginal weighted vaccine performance of a target specific vaccine of size one is its weighted vaccine performance. The marginal weighted vaccine performances for all vaccines are combined into a single list, and the combined list is sorted from largest to least by the weighted marginal vaccine performances of the target specific vaccines as shown in FIG. 6. The combined vaccine of size n is then determined by the first n elements of this list. The peptides for the combined vaccine are determined by the individual peptide target vaccines whose sizes add to n and whose weighted vaccine performances sums to the same sum as the first n elements of the sorted list. This maximizes the vaccine performance of the combined vaccine of size n.

In some embodiments, the combined multiple target vaccine can be designed on its overall predicted coverage for the disease described depending on the presentation table used (e.g., see FIG. 5), by its predicted coverage for a specific indication, and/or by its predicted coverage for a specific target by adjusting the weighting used for vaccine performance accordingly. Once a desired level of coverage is selected, the peptides of the combined vaccine are determined by the contributions of target-specific designs. For example, if the combined vaccine includes a target-specific vaccine of size k, then the vaccine peptides for this target at size k are used in the combined vaccine.

Figure 7:
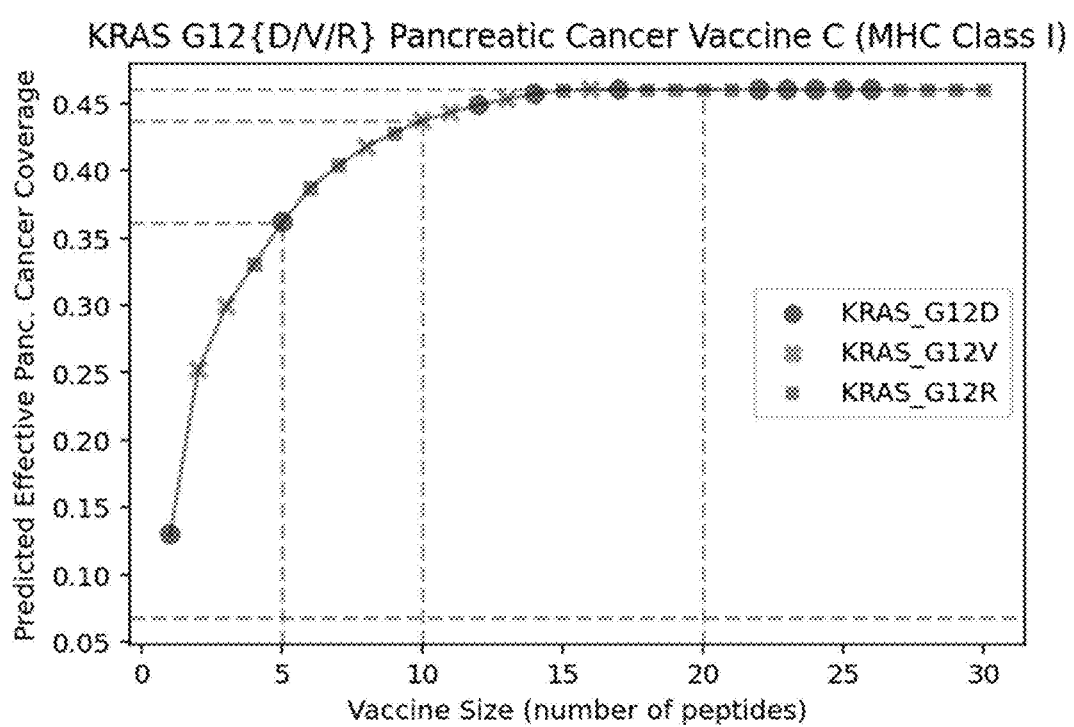
FIG. 7 shows predicted population coverage for pancreatic cancer multiple target (combined) MHC class I vaccines by vaccine size for KRAS G12D, KRAS G12V, and KRAS G12R targets.
Figure 8:
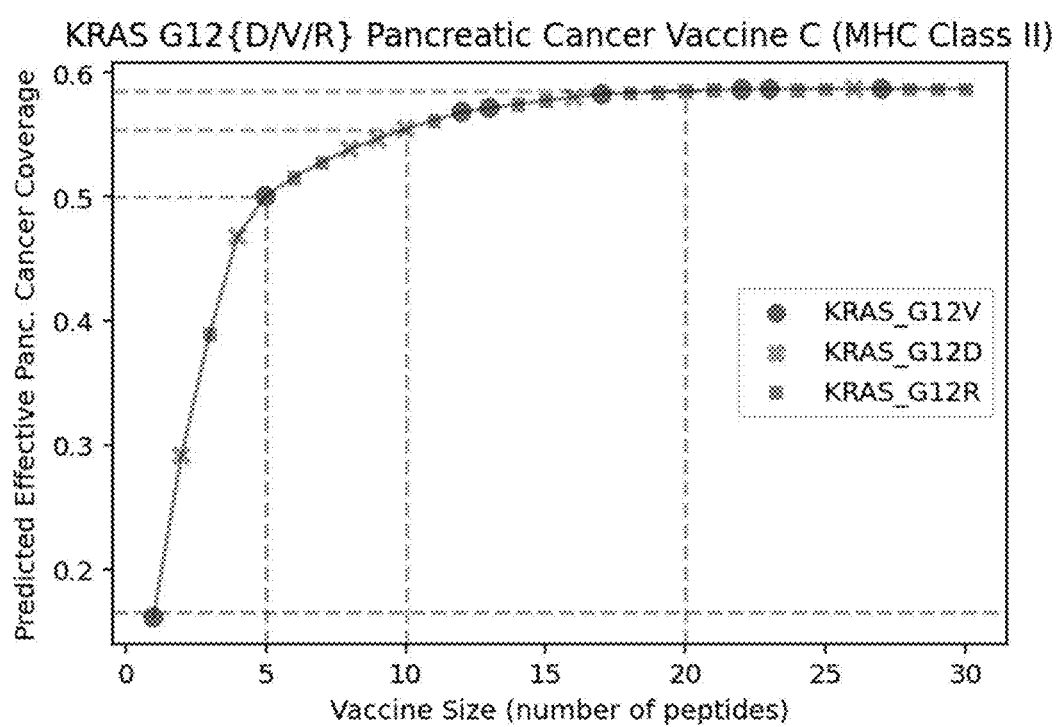
FIG. 8 shows predicted population coverage for pancreatic cancer multiple target (combined) MHC class II vaccines by vaccine size for KRAS G12D, KRAS G12V, and KRAS G12R targets.

As an example of one embodiment, FIG. 5 shows three mutations (KRAS G12D, G12V, and G12R) and their respective probabilities of occurring in an individual with pancreatic cancer. FIG. 3 (MHC class I) and FIG. 4 (MHC class II) show the population coverage of target-specific vaccines for the KRAS G12D, G12V, G12R, G12C, and G13D targets using the methods for vaccines described herein. The marginal population coverage of each target-specific vaccine at a given vaccine size is the improvement in coverage at that size and the size less one. The coverage with no peptides is zero. The marginal coverage of each target-specific vaccine is multiplied by the probability of the target in the population as determined by the proportions as shown in FIG. 5 for the pancreas (pancreatic cancer). These weighted marginal coverages of all target-specific vaccines are sorted to determine the best target-specific compositions, and the resulting list describes the composition of a combined vaccine at each size k by taking the first k elements of the list. As an example of one embodiment, FIG. 7 (MHC Class I) and FIG. 8 (MHC Class II) show the target specific contributions at each vaccine size for a combined KRAS vaccine for the three mutations KRAS G12D, G12V, and G12R. The methods for combined vaccine protocol described herein was used to compute the examples in FIGS. 7 and 8. At each combined vaccine size, different components of the target-specific vaccines are utilized. Table 1 (below) contains the peptides present in independent (single target) and combined (multiple target) MHC class I vaccine designs for the KRAS G12D, G12V, G12R, G12C, and G13D targets. Table 2 (below) contains the contains the peptides present in independent (single target) MHC class II vaccine designs for the KRAS G12D, G12V, G12R, G12C, and G13D targets, and any subset of the individual/single target vaccines can be combined to create an MHC class II vaccine for two or more multiple targets. For alternate embodiments, Sequence Listing provides heteroclitic peptides useful in MHC class I vaccines for the KRAS G12D, G12V, G12R, G12C, and G13D targets.

Combined Vaccine Design Procedure

In some embodiments, the procedure described herein is used to combine individual compact vaccines optimized for different targets into a single optimized combined vaccine.

In some embodiments, the computational inputs for the procedure are:

$\mathcal{T}$ : Set of neoantigen or pathogenic targets of interest (e.g., KRAS G12D, KRAS G12V, KRAS G12R)

$\mathcal{V}$ : Vaccine sets optimized individually for each target. Let $\mathcal{V}_{t,k}$ denote the optimal vaccine set of exactly k peptides for target t∈ $\mathcal{T}$ (e.g., as computed by the procedures describe above). Note that $\mathcal{V}_{t,k+1}$ may not necessarily be a superset of $\mathcal{V}_{t,k}$.

W: $\mathcal{T}$ →[0,1]: Target weighting function mapping each target t∈ $\mathcal{T}$ to a probability or weight of t in a particular presentation of interest (e.g., pancreatic cancer; see Exhibit A, Table 1 for example).

POPULATIONCOVERAGE: $\mathcal{V}$ →[0,1]: Function mapping a peptide set into population coverage (e.g., EvalVax). This function may also take as input additional parameters, including HLA haplotype frequencies and a minimum per-individual number of peptide-HLA hits N (here, we compute coverage as P(n≥1) using EvalVax-Robust).

For each target t (individually) and vaccine size (peptide count) k, the unweighted population coverage $c_{t,k}$ is computed:

$$c_{t,k} = \text{PopulationCoverage}(\mathcal{V}_{t,k}) \forall t \in \mathcal{T}, k$$

Note that for each target t, $c_{t,k}$ is generally monotonically increasing and concave down for increasing values of k (each additional peptide increases coverage but with decreasing returns).

For each target t (individually), the marginal coverage $m_{t,k}$ is computed of the k-th peptide added to the vaccine set:

$$m_{t,k} = \begin{cases} c_{t,k} & \text{if } k = 1 \\ c_{t,k} - c_{t,k-1}, & \text{otherwise} \end{cases} \forall t \in \mathcal{T}, k$$

Note that for each target t, $m_{t,k}$ should be a monotonically decreasing function in k (by Step 1 above).

The weighted marginal population coverage $\tilde{m}_{t,k}$ is computed using weights of each target in W:

$$\tilde{m}_{t,k} = W(t) \cdot m_{t,k} \forall t \in \mathcal{T}, k$$

The weighted marginal population coverage gives the effective marginal coverage of the k-th peptide in the vaccine weighted by the prevalence of the target in the presentation (by multiplication with the probability/weight of the target in the presentation).

The individual vaccines are combined into a combined vaccine via the MERGEMULTI procedure called on the weighted marginal population coverage lists $\tilde{m}_t = [\tilde{m}_{t,k}, k \in 1, 2, \ldots]$. FIG. 9 shows an example Python implementation of the MERGEMULTI function. This procedure takes as input multiple sorted (descending) lists and merges them into a single sorted (descending) list. Let M indicate the output of MERGEMULTI where each element $M_k$ contains both the marginal weighted coverage and source (target) of the k-th peptide in the combined vaccine. The combined vaccine contains peptides from different targets. In particular, the combined vaccine with k peptides contains $C_{t,k} = \Sigma_{j \leq k} \mathbb{1}\{M_k \text{ from } t\}$ peptides from target t. Note that $C_{t,k} \in [0, \ldots, k]$ and $\Sigma_t C_{t,k} = k$ ($C_{t,k}$ gives the distribution of the k peptides in the combined vaccine across the targets).

The optimal combined vaccine set $\hat{\mathcal{V}}_k$ is defined as:

$$\hat{\mathcal{V}}_k = \bigcup_{t \in \mathcal{T}} v_{t,C_{t,k}}$$

Thus, the combined vaccine with k peptides is the combination of the optimal individual $(C_{t,k})$-peptide vaccines. The marginal weighted coverage values of the combine vaccine $M_k$ can be cumulatively summed over k to give the overall effective (target-weighted) population coverage of the combined vaccine containing k peptides as $\Sigma_{j \leq k} M_k$ (taking into account both the probabilities/weights of the targets in the presentation and the expected population coverage of peptides based on HLA display). The final vaccine size k can vary based upon the specific population coverage goals of the vaccine.

MHC Class I Peptide Sequences

In some embodiments, a peptide vaccine (single target or combined multiple target vaccine) comprises about five, ten, or twenty MHC class I peptides with each peptide consisting of 8 or more amino acids. In some embodiments, an MHC class I peptide vaccine is intended for one or more of the KRAS G12D, G12V, and G12R targets. In some embodiments, the amino acid sequence of a first peptide in a five-peptide combined vaccine comprises SEQ ID NO: 1.

```
                              (SEQ ID NO: 1)
GADGVGKSM.
```

In some embodiments, the amino acid sequence of a second peptide in a five-peptide combined vaccine comprises SEQ ID NO: 2.

```
                              (SEQ ID NO: 2)
LMVVGADGV.
```

In some embodiments, the amino acid sequence of a third peptide in a five-peptide combined vaccine comprises SEQ ID NO: 3.

```
                              (SEQ ID NO: 3)
GAVGVGKSL.
```

In some embodiments, the amino acid sequence of a fourth peptide in a five-peptide combined vaccine comprises SEQ ID NO: 4.

```
                              (SEQ ID NO: 4)
LMVVGAVGV.
```

In some embodiments, the amino acid sequence of a fifth peptide in a five-peptide combined vaccine comprises SEQ ID NO: 5.

```
                              (SEQ ID NO: 5)
VTGARGVGK.
```

An example combined vaccine for the KRAS G12D, G12V, and G12R targets with five peptides (SEQ ID NO: 1 to SEQ ID NO: 5) is predicted to have a weighted population coverage of 0.3620.

In some embodiments, any one of the peptides (peptides 1-5) in the five-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, or SEQ ID NO: 5.

In some embodiments, the amino acid sequence of peptides 1 to 5 in a ten-peptide combined vaccine comprise SEQ ID NO: 1, SEQ ID NO: 2, SEQ ID NO: 3, SEQ ID NO: 4, and SEQ ID NO: 5. In some embodiments, the amino acid sequence of a sixth peptide in a ten-peptide combined vaccine comprises SEQ ID NO: 6.

```
                              (SEQ ID NO: 6)
VMGAVGVGK.
```

In some embodiments, the amino acid sequence of a seventh peptide in a ten-peptide combined vaccine comprises SEQ ID NO: 7.

```
                              (SEQ ID NO: 7)
VVGAVGVGK.
```

In some embodiments, the amino acid sequence of an eight peptide in a ten-peptide combined vaccine comprises SEQ ID NO: 8.

```
                              (SEQ ID NO: 8)
GARGVGKSY.
```

In some embodiments, the amino acid sequence of a ninth peptide in a ten-peptide combined vaccine comprises SEQ ID NO: 9.

```
                               (SEQ ID NO: 9)
GPRGVGKSA.
```

In some embodiments, the amino acid sequence of a tenth peptide in a ten-peptide combined vaccine comprises SEQ ID NO: 10.

```
                               (SEQ ID NO: 10)
LMVVGARGV.
```

An example combined vaccine for the KRAS G12D, G12V, and G12R targets with ten peptides (SEQ ID NO: 1 to SEQ ID NO: 10) is predicted to have a weighted population coverage of 0.4374.

In some embodiments, any one of the peptides (peptides 1-10) in the ten-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In some embodiments, the amino acid sequence of peptides 1 to 10 in a twenty-peptide combined vaccine comprise SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. In some embodiments, the amino acid sequence of an 11$^{th}$ peptide in a twenty-peptide combined vaccine comprises SEQ ID NO: 11.

```
                               (SEQ ID NO: 11)
GADGVGKSL.
```

In some embodiments, the amino acid sequence of a 12$^{th}$ peptide in a twenty-peptide combined vaccine comprises SEQ ID NO: 12.

```
                               (SEQ ID NO: 12)
GADGVGKSY.
```

In some embodiments, the amino acid sequence of a 13$^{th}$ peptide in a twenty-peptide combined vaccine comprises SEQ ID NO: 13.

```
                               (SEQ ID NO: 13)
GYDGVGKSM.
```

In some embodiments, the amino acid sequence of a 14$^{th}$ peptide in a twenty-peptide combined vaccine comprises SEQ ID NO: 14.

```
                               (SEQ ID NO: 14)
GPVGVGKSV.
```

In some embodiments, the amino acid sequence of a 15$^{th}$ peptide in a twenty-peptide combined vaccine comprises SEQ ID NO: 15.

```
                               (SEQ ID NO: 15)
LTVVGAVGV.
```

In some embodiments, the amino acid sequence of a 16$^{th}$ peptide in a twenty-peptide combined vaccine comprises SEQ ID NO: 16.

```
                               (SEQ ID NO: 16)
VVGAVGVGR.
```

In some embodiments, the amino acid sequence of a 17$^{th}$ peptide in a twenty-peptide combined vaccine comprises SEQ ID NO: 17.

```
                               (SEQ ID NO: 17)
GARGVGKSM.
```

In some embodiments, the amino acid sequence of an 18$^{th}$ peptide in a twenty-peptide combined vaccine comprises SEQ ID NO: 18.

```
                               (SEQ ID NO: 18)
GPRGVGKSV.
```

In some embodiments, the amino acid sequence of a 19$^{th}$ peptide in a twenty-peptide combined vaccine comprises SEQ ID NO: 19.

```
                               (SEQ ID NO: 19)
LLVVGARGV.
```

In some embodiments, the amino acid sequence of a 20$^{th}$ peptide in a twenty-peptide combined vaccine comprises SEQ ID NO: 20.

```
                               (SEQ ID NO: 20)
VAGARGVGM.
```

An example combined vaccine for the KRAS G12D, G12V, and G12R targets with twenty peptides (SEQ ID NO: 1 to SEQ ID NO: 20) is predicted to have a weighted population coverage of 0.4604.

In some embodiments, any one of the peptides (peptides 1-20) in the twenty-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20

Table 1 shows MHC class I peptide sequences described herein including the respective SEQ ID NO, amino acid sequence corresponding to the SEQ ID NO, KRAS protein target (with specific mutation), the seed amino acid sequence (i.e., the amino acid sequence of the wild type KRAS fragment), the amino acid substitution (if any) for heteroclitic peptides at positions 2 and 9, and notes detailing embodiments in which the peptide may be included in a 5, 10, or 20 combined peptide vaccine as described herein. Table 1 also includes additional peptide sequences comprising SEQ ID NOs: 21-41. In some embodiments, any combination of peptides listed in Table 1 (SEQ ID NOs: 1-41) may be used to create a combined peptide vaccine having between about 2 and about 40 peptides. In some embodiments, any one of the peptides (peptides 1-41; SEQ ID NOs: 1-41) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1-41.

TABLE 1

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 1 | GADGVGKSM | KRAS G12D | GADGVGKSA | — | A9M | Individual KRAS G12D (MHCfluny); Combined (5 peptide) (MHCfluny); Combined (10 peptide) (MHCfluny); Combined (20 peptide) (MHCfluny) |
| SEQ ID NO: 2 | LMVVGADGV | KRAS G12D | LVVVGADGV | V2M | — | Individual KRAS G12D (MHCfluny); Individual KRAS G12D (NetMHCpan); Combined (5 peptide) (MHCfluny); Combined (10 peptide) (MHCfluny); Combined (20 peptide) (MHCfluny) |
| SEQ ID NO: 3 | GAVGVGKSL | KRAS G12V | GAVGVGKSA | — | A9L | Individual KRAS G12V (MHCfluny); Combined (5 peptide) (MHCfluny); Combined (10 peptide) (MHCfluny); Combined (20 peptide) (MHCfluny) |
| SEQ ID NO: 4 | LMVVGAVGV | KRAS G12V | LVVVGAVGV | V2M | — | Individual KRAS G12V (MHCfluny); Individual KRAS G12V (NetMHCpan); Combined (5 peptide) (MHCfluny); Combined (10 peptide) (MHCfluny); Combined (20 peptide) (MHCfluny) |
| SEQ ID NO: 5 | VTGARGVGK | KRAS G12R | VVGARGVGK | V2T | — | Individual KRAS G12R (MHCfluny); Combined (5 peptide) (MHCfluny); Combined (10 peptide) (MHCfluny); Combined (20 peptide) (MHCfluny) |
| SEQ ID NO: 6 | VMGAVGVGK | KRAS G12V | VVGAVGVGK | V2M | — | Individual KRAS G12V (MHCfluny); Combined (10 peptide) (MHCfluny); Combined (20 peptide) (MHCfluny) |
| SEQ ID NO: 7 | VVGAVGVGK | KRAS G12V | VVGAVGVGK | — | — | Individual KRAS G12V (NetMHCpan); Combined (10 peptide) (MHCfluny); Combined (20 peptide) (MHCfluny) |
| SEQ ID NO: 8 | GARGVGKSY | KRAS G12R | GARGVGKSA | — | A9Y | Individual KRAS G12R (MHCfluny); Combined (10 peptide) (MHCfluny); Combined (20 peptide) (MHCfluny) |
| SEQ ID NO: 9 | GPRGVGKSA | KRAS G12R | GARGVGKSA | A2P | — | Individual KRAS G12R (MHCfluny); Combined (10 peptide) (MHCfluny); Combined (20 peptide) (MHCfluny) |
| SEQ ID NO: 10 | LMVVGARGV | KRAS G12R | LVVVGARGV | V2M | — | Individual KRAS G12R (MHCfluny); Individual KRAS G12R (NetMHCpan); |

TABLE 1-continued

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 11 | GADGVGKSL | KRAS G12D | GADGVGKSA | — | A9L | Combined (10 peptide) (MHCfluny); Combined (20 peptide) (MHCfluny) Individual KRAS G12D (MHCfluny); Combined (20 peptide) (MHCfluny) |
| SEQ ID NO: 12 | GADGVGKSY | KRAS G12D | GADGVGKSA | — | A9Y | Individual KRAS G12D (MHCfluny); Combined (20 peptide) (MHCfluny) |
| SEQ ID NO: 13 | GYDGVGKSM | KRAS G12D | GADGVGKSA | A2Y | A9M | Individual KRAS G12D (MHCfluny); Combined (20 peptide) (MHCfluny) |
| SEQ ID NO: 14 | GPVGVGKSV | KRAS G12V | GAVGVGKSA | A2P | A9V | Combined (20 peptide) (MHCfluny) |
| SEQ ID NO: 15 | LTVVGAVGV | KRAS G12V | LVVVGAVGV | V2T | — | Individual KRAS G12V (NetMHCpan); Combined (20 peptide) (MHCfluny) |
| SEQ ID NO: 16 | VVGAVGVGR | KRAS G12V | VVGAVGVGK | — | K9R | Individual KRAS G12V (MHCfluny); Individual KRAS G12V (NetMHCpan); Combined (20 peptide) (MHCfluny) |
| SEQ ID NO: 17 | GARGVGKSM | KRAS G12R | GARGVGKSA | — | A9M | Combined (20 peptide) (MHCfluny) |
| SEQ ID NO: 18 | GPRGVGKSV | KRAS G12R | GARGVGKSA | A2P | A9V | Combined (20 peptide) (MHCfluny) |
| SEQ ID NO: 19 | LLVVGARGV | KRAS G12R | LVVVGARGV | V2L | — | Individual KRAS G12R (NetMHCpan); Combined (20 peptide) (MHCfluny) |
| SEQ ID NO: 20 | VAGARGVGM | KRAS G12R | VVGARGVGK | V2A | K9M | Individual KRAS G12R (MHCfluny); Combined (20 peptide) (MHCfluny) |
| SEQ ID NO: 21 | LTVVGADGV | KRAS G12D | LVVVGADGV | V2T | — | Individual KRAS G12D (NetMHCpan) |
| SEQ ID NO: 22 | LLVVGADGV | KRAS G12D | LVVVGADGV | V2L | — | Individual KRAS G12D (NetMHCpan) |
| SEQ ID NO: 23 | LMVVGADGL | KRAS G12D | LVVVGADGV | V2M | V9L | Individual KRAS G12D (NetMHCpan) |
| SEQ ID NO: 24 | VMGAVGVGR | KRAS G12V | VVGAVGVGK | V2M | K9R | Individual KRAS G12V (NetMHCpan) |
| SEQ ID NO: 25 | VMGARGVGK | KRAS G12R | VVGARGVGK | V2M | — | Individual KRAS G12R (NetMHCpan) |
| SEQ ID NO: 26 | GACGVGKSL | KRAS G12C | GACGVGKSA | — | A9L | Individual KRAS G12C (MHCfluny) |
| SEQ ID NO: 27 | LMVVGACGV | KRAS G12C | LVVVGACGV | V2M | — | Individual KRAS G12C (MHCfluny); Individual KRAS G12C (NetMHCpan) |
| SEQ ID NO: 28 | LTVVGACGV | KRAS G12C | LVVVGACGV | V2T | — | Individual KRAS G12C (MHCfluny); Individual KRAS G12C (NetMHCpan) |
| SEQ ID NO: 29 | VTGACGVGK | KRAS G12C | VVGACGVGK | V2T | — | Individual KRAS G12C (MHCfluny) |
| SEQ ID NO: 30 | VVGACGVGR | KRAS G12C | VVGACGVGK | — | K9R | Individual KRAS G12C (MHCfluny) |
| SEQ ID NO: 31 | AADVGKSAM | KRAS G13D | AGDVGKSAL | G2A | L9M | Individual KRAS G13D (MHCfluny); Individual KRAS G13D (NetMHCpan) |
| SEQ ID NO: 32 | AEDVGKSAM | KRAS G13D | AGDVGKSAL | G2E | L9M | Individual KRAS G13D (MHCfluriy) |
| SEQ ID NO: 33 | AYDVGKSAM | KRAS G13D | AGDVGKSAL | G2Y | L9M | Individual KRAS G13D (MHCfluriy) |
| SEQ ID NO: 34 | DAGKSALTV | KRAS G13D | DVGKSALTI | V2A | I9V | Individual KRAS G13D (MHCfluny) |

TABLE 1-continued

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 35 | GAGDVGKSM | KRAS G13D | GAGDVGKSA | — | A9M | Individual KRAS G13D (MHCfluriy) |
| SEQ ID NO: 36 | LQVVGACGV | KRAS G12C | LVVVGACGV | V2Q | — | Individual KRAS G12C (NetMHCpan) |
| SEQ ID NO: 37 | VMGACGVGK | KRAS G12C | VVGACGVGK | V2M | — | Individual KRAS G12C (NetMHCpan) |
| SEQ ID NO: 38 | VMGACGVGR | KRAS G12C | VVGACGVGK | V2M | K9R | Individual KRAS G12C (NetMHCpan) |
| SEQ ID NO: 39 | AADVGKSAL | KRAS G13D | AGDVGKSAL | G2A | — | Individual KRAS G13D (NetMHCpan) |
| SEQ ID NO: 40 | ASDVGKSAL | KRAS G13D | AGDVGKSAL | G2S | — | Individual KRAS G13D (NetMHCpan) |
| SEQ ID NO: 41 | ASDVGKSAM | KRAS G13D | AGDVGKSAL | G2S | L9M | Individual KRAS G13D (NetMHCpan) |

Additional amino acid sequences of MHC class I heteroclitic peptides are provided in Sequence Listings (SEQ ID NOs: 67-1522). In some embodiments, any combination of MHC class I peptides disclosed herein (SEQ ID NOs: 1-41 and 67-1522) may be used to create a combined peptide vaccine having between about 2 and about 40 peptides. In some embodiments, any one of the peptides (SEQ ID NOs: 1-41 and 67-1522) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 1-41 or 67-1522.

MHC Class II Peptide Sequences

In some embodiments, a peptide vaccine (single target or combined multiple target vaccine) comprises about 2 to 40 MHC class II peptides with each peptide consisting of about 20 amino acids. In some embodiments, an MHC class II peptide vaccine is intended for one or more of the KRAS G12D, G12V, G12R, G12C, and G13D targets.

Table 2 summarizes MHC class II peptide sequences described herein including the respective SEQ ID NO, amino acid sequence corresponding to the SEQ ID NO, the amino acid sequence corresponding to the peptide's binding core, the KRAS protein target (with specific mutation), the seed amino acid sequence (i.e., the amino acid sequence of the wild type KRAS fragment), the seed amino acid sequence of the binding core, and the amino acid substitution (if any) for heteroclitic peptides at positions 1, 4, 6, and 9. Table 2 includes peptide sequences comprising SEQ ID NOs: 42-66. SEQ ID NOs: 42-65 (Table 2) encode for recombinant peptides. In some embodiments, any combination of peptides listed in Table 2 (SEQ ID NOs: 42-66) may be used to create a single target (individual) or combined peptide vaccine having between about 2 and about 40 peptides. In some embodiments, any one of the peptides (peptides 42-66; SEQ ID NOs: 42-66) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 42-66.

TABLE 2

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 42 | EYKFVVFGSDGAGKS | FVVFGSDGA | KRAS G12D | EYKLVVVGADGVGKS | LVVVGADGV | L1F | V4F | A6S | V9A | Individual KRAS G12D (NetMHCIIpan) |
| SEQ ID NO: 43 | EYKFVVIGNDGAGKSALTIQLIQN | FVVIGNDGA | KRAS G12D | EYKLVVVGADGVGKSALTIQLIQN | LVVVGADGV | L1F | V4I | A6N | V9A | Individual KRAS G12D (NetMHCIIpan) |
| SEQ ID NO: 44 | EYKFVVLGADGAGKS | FVVLGADGA | KRAS G12D | EYKLVVVGADGVGKS | LVVVGADGV | L1F | V4L | — | V9A | Individual KRAS G12D (NetMHCIIpan) |
| SEQ ID NO: 45 | MTEYKFVVSGADGIGKSALT | FVVSGADGI | KRAS G12D | MTEYKLVVVGADGVGKSALT | LVVVGADGV | L1F | V4S | — | V9I | Individual KRAS G12D (NetMHCIIpan) |
| SEQ ID NO: 46 | MTEYKFVVYGSDGIGKSALT | FVVYGSDGI | KRAS G12D | MTEYKLVVVGADGVGKSALT | LVVVGADGV | L1F | V4Y | A6S | V9I | Individual KRAS G12D (NetMHCIIpan) |
| SEQ ID NO: 47 | EYKFVVIGRVGHGKS | FVVIGRVGH | KRAS G12V | EYKLVVVGAVGVGKS | LVVVGAVGV | L1F | V4I | A6R | V9H | Individual KRAS G12V (NetMHCIIpan) |

TABLE 2-continued

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 48 | EYKFVVLGTVGHGKS | FVVLGTVGH | KRAS G12V | EYKLVVVGAVGVGKS | LVVVGAVGV | L1F | V4L | A6T | V9H | Individual KRAS G12V (NetMHCIIpan) |
| SEQ ID NO: 49 | EYKFVVYGNVGMGKS | FVVYGNVGM | KRAS G12V | EYKLVVVGAVGVGKS | LVVVGAVGV | L1F | V4Y | A6N | V9M | Individual KRAS G12V (NetMHCIIpan) |
| SEQ ID NO: 50 | EYKIVVAGNVGIGKS | IVVAGNVGI | KRAS G12V | EYKLVVVGAVGVGKS | LVVVGAVGV | L1I | V4A | A6N | V9I | Individual KRAS G12V (NetMHCIIpan) |
| SEQ ID NO: 51 | TEYKIVVMGNVGYGK | IVVMGNVGY | KRAS G12V | TEYKLVVVGAVGVGK | LVVVGAVGV | L1I | V4M | A6N | V9Y | Individual KRAS G12V (NetMHCIIpan) |
| SEQ ID NO: 52 | MTEYKFVVFGSRGVGKSALT | FVVFGSRGV | KRAS G12R | MTEYKLVVVGARGVGKSALT | LVVVGARGV | L1F | V4F | A6S | — | Individual KRAS G12R (NetMHCIIpan) |
| SEQ ID NO: 53 | MTEYKFVVIGNRGVGKSALT | FVVIGNRGV | KRAS G12R | MTEYKLVVVGARGVGKSALT | LVVVGARGV | L1F | V4I | A6N | — | Individual KRAS G12R (NetMHCIIpan) |
| SEQ ID NO: 54 | MTEYKFVVIGVRGDGKSALT | FVVIGVRGD | KRAS G12R | MTEYKLVVVGARGVGKSALT | LVVVGARGV | L1F | V4I | A6V | V9D | Individual KRAS G12R (NetMHCIIpan) |
| SEQ ID NO: 55 | MTEYKFVVMGSRGAGKSALT | FVVMGSRGA | KRAS G12R | MTEYKLVVVGARGVGKSALT | LVVVGARGV | L1F | V4M | A6S | V9A | Individual KRAS G12R (NetMHCIIpan) |
| SEQ ID NO: 56 | VVVIARGVPKSLLTI | IARGVPKSL | KRAS G12R | VVVGARGVGKSALTI | GARGVGKSA | G1I | — | G6P | A9L | Individual KRAS G12R (NetMHCIIpan) |
| SEQ ID NO: 57 | EYKFVVFGNCGAGKS | FVVFGNCGA | KRAS G12C | EYKLVVVGACGVGKS | LVVVGACGV | L1F | V4F | A6N | V9A | Individual KRAS G12C (NetMHCIIpan) |
| SEQ ID NO: 58 | EYKFVVSGACGVGKS | FVVSGACGV | KRAS G12C | EYKLVVVGACGVGKS | LVVVGACGV | L1F | V4S | — | — | Individual KRAS G12C (NetMHCIIpan) |
| SEQ ID NO: 59 | EYKFVVSGNCGLGKS | FVVSGNCGL | KRAS G12C | EYKLVVVGACGVGKS | LVVVGACGV | L1F | V4S | A6N | V9L | Individual KRAS G12C (NetMHCIIpan) |
| SEQ ID NO: 60 | EYKLVVMGPCGAGKS | LVVMGPCGA | KRAS G12C | EYKLVVVGACGVGKS | LVVVGACGV | — | V4M | A6P | V9A | Individual KRAS G12C (NetMHCIIpan) |
| SEQ ID NO: 61 | KLVIVGICKVGHSAL | IVGICKVGH | KRAS G12C | KLVVVGACGVGKSAL | VVGACGVGK | V1I | A4I | G6K | K9H | Individual KRAS G12C (NetMHCIIpan) |
| SEQ ID NO: 62 | EYKFVVFGNGDLGKS | FVVFGNGDL | KRAS G13D | EYKLVVVGAGDVGKS | LVVVGAGDV | L1F | V4F | A6N | V9L | Individual KRAS G13D (NetMHCIIpan) |
| SEQ ID NO: 63 | EYKFVVMGNGDSGKS | FVVMGNGDS | KRAS G13D | EYKLVVVGAGDVGKS | LVVVGAGDV | L1F | V4M | A6N | V9S | Individual KRAS G13D (NetMHCIIpan) |
| SEQ ID NO: 64 | EYKFVVSGSGDVGKS | FVVSGSGDV | KRAS G13D | EYKLVVVGAGDVGKS | LVVVGAGDV | L1F | V4S | A6S | — | Individual KRAS G13D (NetMHCIIpan) |
| SEQ ID NO: 65 | EYKIVVMGRGDMGKS | IVVMGRGDM | KRAS G13D | EYKLVVVGAGDVGKS | LVVVGAGDV | L1I | V4M | A6R | V9M | Individual KRAS G13D (NetMHCIIpan) |

TABLE 2-continued

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 66 | YKLVVVGAGDVGKSA KRAS | — | KRAS G13D | — | — | — | — | — | — | Individual KRAS G13D (NetMHCIIpan) |

In some embodiments, any combination of MHC class I and/or MHC class II peptides disclosed herein (SEQ ID NOs: 1-1522) may be used to create a single target (individual) or combined peptide vaccine having between about 2 and about 40 peptides. In some embodiments, any one of the peptides (peptides 1-1522; SEQ ID NOs: 1-1522) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1-1522.

mRNA and DNA Vaccines

In some embodiments, vaccine peptides are encoded as mRNA or DNA molecules and are administered for expression in vivo as is known in the art. One example of the delivery of vaccines by mRNA is found in Kranz et al. (2016), incorporated herein by reference. In one embodiment, a construct comprises 10 peptides, including a five-peptide MHC class I combined pancreatic cancer vaccine (targets: KRAS G12D, G12V, G12R) and a five-peptide MHC class II combined pancreatic cancer vaccine (targets: KRAS G12D, G12V, G12R), as optimized by the procedure described herein. Peptides are prepended with a secretion signal sequence at the N-terminus and followed by an MHC class I trafficking signal (MITD) (Kreiter et al., 2008; Sahin et al., 2017). The MITD has been shown to route antigens to pathways for HLA class I and class II presentation (Kreiter et al., 2008). Here we combine all peptides of each MHC class into a single construct using non-immunogenic glycine/serine linkers from Sahin et al. (2017), though it is also plausible to construct individual constructs containing single peptides with the same secretion and MITD signals as demonstrated by Kreiter et al. (2008).

In some embodiments, the amino acid sequence encoded by the mRNA vaccine comprises SEQ ID NO: 1523. Underlined amino acids correspond to the signal peptide (or leader) sequence. Bolded amino acids correspond to MHC class I (9 amino acids in length; 5 peptides) and MHC class II (13-25 amino acids in length; 5 peptides) peptide sequences. Italicized amino acids correspond to the trafficking signal.

(SEQ ID NO: 1523)
MRVTAPRTLILLLSGALALTETWAGSGGSGGGGSGGG**ADGVGKSMGGSGGG
GSGGLMVVGADGVGGSGGGGSGGGAVGVGKSLGGSGGGGSGGLMVVGAVGV
GGSGGGGSGGVTGARGVGKGGSGGGGSGGEYKFVVLGTVGHGK**SGGSGGGG
SGGEYKIVVAGNVGIGKSGGSGGGGSGGEYKFVVFGSDGAGKSGGSGGGGS
GGMTEYKFVVSGADGIGKSALTGGSGGGGSGGMTEYKFVVIGNRGVGKSAL
TGGSLGGGGSG*IVGIVAGLAVLAVVVIGAVVATVMCRRKSSGGKGGSYSQA
ASSDSAQGSDVSLTA*.

In some embodiments, the vaccine is an mRNA vaccine comprising a nucleic acids sequence encoding the amino acid sequence consisting of SEQ ID NO: 1523. In some embodiments, the nucleic acid sequence of the mRNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 1523.

In some embodiments, the vaccine is a DNA vaccine comprising a nucleic acids sequence encoding the amino acid sequence consisting of SEQ ID NO: 1523. In some embodiments, the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 1523.

In some embodiments, one or more MHC class I and/or MHC class II peptides disclosed herein (SEQ ID NO: 1-1522) can be encoded in one or more mRNA or DNA molecules and administered for expression in vivo. In some embodiments between about 2 and about 40 peptide sequences are encoded in one or more mRNA constructs. In some embodiments, between about 2 and about 40 peptide sequences are encoded in one or more DNA constructs (i.e., nucleic acids encoding the amino acids sequences comprising on or more of SEQ ID NOs: 1-1522). In some embodiments, the amino acid sequence of the mRNA vaccine or the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to any of SEQ ID NOs: 1-1522.

Non-Limiting Embodiments of the Subject Matter

In one aspect, the invention provides for a nucleic acid sequence encoding two or more amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some embodiments, the nucleic acid sequence is an immunogenic composition. In some embodiments, the nucleic acid sequence is administered in a construct for expression in vivo. In some embodiments, the in vivo administration of the nucleic acid sequence is configured to produce one or more peptides that are displayed by an HLA class I molecule. In some embodiments, the one or more peptides is a modified or unmodified fragment of a mutated KRAS protein. In some embodiments, the mutated KRAS protein is selected from the group consisting of KRAS G12D, KRAS G12V, and KRAS G12R. In some embodiments, the nucleic acid sequence is administered in an effective amount to a subject to prevent cancer. In some embodiments, the nucleic acid sequence is administered in an effective amount to a subject to treat cancer.

In another aspect, the invention provides for an immunogenic peptide composition comprising two or more peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some embodiments, a peptide in the immunogenic peptide composition is displayed by an HLA class I molecule. In some embodiments, a peptide in the immunogenic peptide composition is a modified or unmodified fragment of a mutated KRAS protein. In some embodiments, the mutated KRAS protein is selected from the group consisting of KRAS G12D, KRAS G12V, and KRAS G12R. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic peptide composition comprises at least three peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In another aspect, the invention provides for a nucleic acid sequence encoding one or more amino acid sequences selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments, the nucleic acid sequence is an immunogenic composition. In some embodiments, the nucleic acid sequence is administered in a construct for expression in vivo. In some embodiments, the in vivo administration of the nucleic acid sequence is configured to produce one or more peptides that are displayed by an HLA class II molecule. In some embodiments, the one or more peptides is a modified fragment of a mutated KRAS protein. In some embodiments, the mutated KRAS protein is selected from the group consisting of KRAS G12D, KRAS G12V, KRAS G12R, KRAS G12C, and KRAS G13D. In some embodiments, the nucleic acid sequence is administered in an effective amount to a subject to prevent cancer. In some embodiments, the nucleic acid sequence is administered in an effective amount to a subject to treat cancer.

In another aspect, the invention provides for an immunogenic peptide composition comprising one or more peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments, a peptide in the immunogenic peptide composition is displayed by an HLA class II molecule. In some embodiments, a peptide in the immunogenic peptide composition is a modified or unmodified fragment of a mutated KRAS protein. In some embodiments, the mutated KRAS protein is selected from the group consisting of KRAS G12D, KRAS G12V, KRAS G12R, KRAS G12C, and KRAS G13D. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic peptide composition comprises at least two peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

Compositions

In some embodiments, the foreign peptides (e.g., peptide vaccine) are administered in a pharmaceutical composition comprising the peptides and a pharmaceutically acceptable carrier. In some embodiments, the pharmaceutical composition is in the form of a spray, aerosol, gel, solution, emulsion, or suspension.

The composition is preferably administered to a subject with a pharmaceutically acceptable carrier. Typically, in some embodiments, an appropriate amount of a pharmaceutically acceptable salt is used in the formulation, which in some embodiments can render the formulation isotonic.

In certain embodiments, the foreign peptides are provided as an immunogenic composition comprising any one of the foreign peptides described herein and a pharmaceutically acceptable carrier. In certain embodiments, the immunogenic composition further comprises an adjuvant. In certain embodiments, the foreign peptides are conjugated with other molecules to increase their effectiveness as is known by those practiced in the art. For example, peptides can be coupled to antibodies that recognize cell surface proteins on antigen presenting cells to enhance vaccine effectiveness. One such method for increasing the effectiveness of peptide delivery is described in Woodham, et al. (2018).

In some embodiments, the pharmaceutically acceptable carrier is selected from the group consisting of saline, Ringer's solution, dextrose solution, and a combination thereof. Other suitable pharmaceutically acceptable carriers known in the art are contemplated. Suitable carriers and their formulations are described in Remington's Pharmaceutical Sciences, 2005, Mack Publishing Co. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of peptides being administered.

The phrase pharmaceutically acceptable carrier as used herein means a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier is acceptable in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term carrier denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency. The composition may also include additional agents such as an isotonicity agent, a preservative, a surfactant, and, a divalent cation, preferably, zinc.

The composition can also include an excipient, or an agent for stabilization of a foreign peptide composition, such as a buffer, a reducing agent, a bulk protein, amino acids (such as e.g., glycine or praline) or a carbohydrate. Bulk proteins useful in formulating foreign peptide compositions include albumin. Typical carbohydrates useful in formulating foreign peptides include but are not limited to sucrose, mannitol, lactose, trehalose, or glucose.

Surfactants may also be used to prevent soluble and insoluble aggregation and/or precipitation of foreign peptides or proteins included in the composition. Suitable surfactants include but are not limited to sorbitan trioleate, soya lecithin, and oleic acid. In certain cases, solution aerosols are preferred using solvents such as ethanol. Thus, formulations including foreign peptides can also include a surfactant that can reduce or prevent surface-induced aggregation of foreign peptides by atomization of the solution in forming an aerosol. Various conventional surfactants can be employed, such as polyoxyethylene fatty acid esters and alcohols, and polyoxyethylene sorbitol fatty acid esters. Amounts will generally range between 0.001% and 4% by weight of the formulation. In some embodiments, surfactants used with the present disclosure are polyoxyethylene sorbitan mono-oleate, polysorbate 80, polysorbate 20. Additional agents known in the art can also be included in the composition.

In some embodiments, the pharmaceutical compositions and dosage forms further comprise one or more compounds that reduce the rate by which an active ingredient will decay, or the composition will change in character. So called stabilizers or preservatives may include, but are not limited to, amino acids, antioxidants, pH buffers, or salt buffers. Nonlimiting examples of antioxidants include butylated hydroxy anisole (BHA), ascorbic acid and derivatives thereof, tocopherol and derivatives thereof, butylated hydroxy anisole and cysteine. Nonlimiting examples of preservatives include parabens, such as methyl or propyl p-hydroxybenzoate and benzalkonium chloride. Additional nonlimiting examples of amino acids include glycine or proline.

The present invention also teaches the stabilization (preventing or minimizing thermally or mechanically induced soluble or insoluble aggregation and/or precipitation of an inhibitor protein) of liquid solutions containing foreign peptides at neutral pH or less than neutral pH by the use of amino acids including proline or glycine, with or without divalent cations resulting in clear or nearly clear solutions that are stable at room temperature or preferred for pharmaceutical administration.

In one embodiment, the composition is a pharmaceutical composition of single unit or multiple unit dosage forms. Pharmaceutical compositions of single unit or multiple unit dosage forms of the invention comprise a prophylactically or therapeutically effective amount of one or more compositions (e.g., a compound of the invention, or other prophylactic or therapeutic agent), typically, one or more vehicles, carriers, or excipients, stabilizing agents, and/or preservatives. Preferably, the vehicles, carriers, excipients, stabilizing agents and preservatives are pharmaceutically acceptable.

In some embodiments, the pharmaceutical compositions and dosage forms comprise anhydrous pharmaceutical compositions and dosage forms. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Suitable vehicles are well known to those skilled in the art of pharmacy, and non-limiting examples of suitable vehicles include glucose, sucrose, starch, lactose, gelatin, rice, silica gel, glycerol, talc, sodium chloride, dried skim milk, propylene glycol, water, sodium stearate, ethanol, and similar substances well known in the art. Saline solutions and aqueous dextrose and glycerol solutions can also be employed as liquid vehicles. Whether a particular vehicle is suitable for incorporation into a pharmaceutical composition or dosage form depends on a variety of factors well known in the art including, but not limited to, the way in which the dosage form will be administered to a patient and the specific active ingredients in the dosage form. Pharmaceutical vehicles can be sterile liquids, such as water and oils, including those of petroleum, animal, vegetable or synthetic origin, such as peanut oil, soybean oil, mineral oil, sesame oil and the like.

The invention also provides that a pharmaceutical composition can be packaged in a hermetically sealed container such as an ampoule or sachette indicating the quantity. In one embodiment, the pharmaceutical composition can be supplied as a dry sterilized lyophilized powder in a delivery device suitable for administration to the lower airways of a patient. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for administration may be in the form of powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention (e.g., peptides) as an active ingredient.

A liquid composition herein can be used as such with a delivery device, or they can be used for the preparation of pharmaceutically acceptable formulations comprising foreign peptides that are prepared for example by the method of spray drying. The methods of spray freeze-drying foreign peptides/proteins for pharmaceutical administration disclosed in Maa et al., Curr. Pharm. Biotechnol., 2001, 1, 283-302, are incorporated herein. In another embodiment, the liquid solutions herein are freeze spray dried and the spray-dried product is collected as a dispersible foreign peptide-containing powder that is therapeutically effective when administered to an individual.

The compounds and pharmaceutical compositions of the present invention can be employed in combination therapies, that is, the compounds and pharmaceutical compositions can be administered concurrently with, prior to, or subsequent to, one or more other desired therapeutics or medical procedures (e.g., foreign peptide vaccine can be used in combination therapy with another treatment such as chemotherapy, radiation, pharmaceutical agents, and/or another treatment). The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another therapeutic or prophylactic).

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The current invention provides for dosage forms comprising foreign peptides suitable for treating cancer or other diseases. The dosage forms can be formulated, e.g., as sprays, aerosols, nanoparticles, liposomes, or other forms known to one of skill in the art. See, e.g., Remington's Pharmaceutical Sciences; Remington: The Science and Practice of Pharmacy supra; Pharmaceutical Dosage Forms and Drug Delivery Systems by Howard C., Ansel et al., Lippincott Williams & Wilkins; 7th edition (Oct. 1, 1999).

Generally, a dosage form used in the acute treatment of a disease may contain larger amounts of one or more of the active ingredients it comprises than a dosage form used in the chronic treatment of the same disease. In addition, the prophylactically and therapeutically effective dosage form may vary among different conditions. For example, a therapeutically effective dosage form may contain peptides that has an appropriate immunogenic action when intending to treat cancer or other disease. On the other hand, a different effective dosage may contain foreign peptides that has an appropriate immunogenic action when intending to use the peptides of the invention as a prophylactic (e.g., vaccine) against cancer or another disease/condition. These and other ways in which specific dosage forms encompassed by this invention will vary from one another and will be readily apparent to those skilled in the art. See, e.g., Remington's Pharmaceutical Sciences, 2005, Mack Publishing Co.; Remington: The Science and Practice of Pharmacy by Gennaro, Lippincott Williams & Wilkins; 20th edition (2003); Pharmaceutical Dosage Forms and Drug Delivery Systems by Howard C. Ansel et al., Lippincott Williams & Wilkins; 7th edition (Oct. 1, 1999); and Encyclopedia of Pharmaceutical Technology, edited by Swarbrick, J. & J. C. Boylan, Marcel Dekker, Inc., New York, 1988, which are incorporated herein by reference in their entirety.

The pH of a pharmaceutical composition or dosage form may also be adjusted to improve delivery and/or stability of one or more active ingredients. Similarly, the polarity of a solvent carrier, its ionic strength, or tonicity can be adjusted to improve delivery. Compounds such as stearates can also be added to pharmaceutical compositions or dosage forms to alter advantageously the hydrophilicity or lipophilicity of one or more active ingredients to improve delivery. In this regard, stearates can also serve as a lipid vehicle for the formulation, as an emulsifying agent or surfactant, and as a delivery enhancing or penetration-enhancing agent. Different salts, hydrates, or solvates of the active ingredients can be used to adjust further the properties of the resulting composition.

Compositions can be formulated with appropriate carriers and adjuvants using techniques to yield compositions suitable for immunization. The compositions can include an adjuvant, such as, for example but not limited to, alum, poly IC, MF-59, squalene-based adjuvants, or liposomal based adjuvants suitable for immunization.

In some embodiments, the compositions and methods comprise any suitable agent or immune modulation which could modulate mechanisms of host immune tolerance and release of the induced antibodies. In certain embodiments, an immunomodulatory agent is administered in at time and in an amount sufficient for transient modulation of the subject's immune response so as to induce an immune response which comprises antibodies against for example tumor neoantigens (i.e., tumor-specific antigens (TSA)).

Expression Systems

In certain aspects, the invention provides culturing a cell line that expresses any one of the foreign peptides of the invention in a culture medium comprising any of the foreign peptides described herein.

Various expression systems for producing recombinant proteins/peptides are known in the art, and include, prokaryotic (e.g., bacteria), plant, insect, yeast, and mammalian expression systems. Suitable cell lines, can be transformed, transduced, or transfected with nucleic acids containing coding sequences for the foreign peptides of the invention in order to produce the molecule of interest. Expression vectors containing such a nucleic acid sequence, which can be linked to at least one regulatory sequence in a manner that allows expression of the nucleotide sequence in a host cell, can be introduced via methods known in the art. Practitioners in the art understand that designing an expression vector can depend on factors, such as the choice of host cell to be transfected and/or the type and/or amount of desired protein to be expressed. Enhancer regions, which are those sequences found upstream or downstream of the promoter region in non-coding DNA regions, are also known in the art to be important in optimizing expression. If needed, origins of replication from viral sources can be employed, such as if a prokaryotic host is utilized for introduction of plasmid DNA. However, in eukaryotic organisms, chromosome integration is a common mechanism for DNA replication. For stable transfection of mammalian cells, a small fraction of cells can integrate introduced DNA into their genomes. The expression vector and transfection method utilized can be factors that contribute to a successful integration event. For stable amplification and expression of a desired protein, a vector containing DNA encoding a protein of interest is stably integrated into the genome of eukaryotic cells (for example mammalian cells), resulting in the stable expression of transfected genes. A gene that encodes a selectable marker (for example, resistance to antibiotics or drugs) can be introduced into host cells along with the gene of interest in order to identify and select clones that stably express a gene encoding a protein of interest. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein molecule.

A host cell strain, which modulates the expression of the inserted sequences, or modifies and processes the nucleic acid in a specific fashion desired also may be chosen. Such modifications (for example, glycosylation and other post-translational modifications) and processing (for example, cleavage) of peptide/protein products may be important for the function of the peptide/protein. Different host cell strains have characteristic and specific mechanisms for the post-translational processing and modification of proteins and gene products. As such, appropriate host systems or cell lines can be chosen to ensure the correct modification and processing of the foreign protein expressed. Thus, eukaryotic host cells possessing the cellular machinery for proper processing of the primary transcript, glycosylation, and phosphorylation of the gene product may be used.

Various culturing parameters can be used with respect to the host cell being cultured. Appropriate culture conditions for mammalian cells are well known in the art (Cleveland W L, et al., J Immunol Methods, 1983, 56(2): 221-234) or can be determined by the skilled artisan (see, for example, Animal Cell Culture: A Practical Approach 2nd Ed., Rickwood, D. and Hames, B. D., eds. (Oxford University Press: New York, 1992)). Cell culturing conditions can vary according to the type of host cell selected. Commercially available medium can be utilized.

Foreign peptides of the invention can be purified from any human or non-human cell which expresses the polypeptide, including those which have been transfected with expression constructs that express foreign peptides of the invention. For protein recovery, isolation and/or purification, the cell culture medium or cell lysate is centrifuged to remove particulate cells and cell debris. The desired polypeptide molecule is isolated or purified away from contaminating soluble proteins and polypeptides by suitable purification techniques. Non-limiting purification methods for proteins include: size exclusion chromatography; affinity chromatography; ion exchange chromatography; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anionexchange resins, in which the more acidic fraction(s) is/are collected.

Methods of Treatment

In one embodiment, the subject matter disclosed herein relates to a preventive medical treatment started after following diagnosis of cancer in order to prevent the disease from worsening or curing the disease. In one embodiment, the subject matter disclosed herein relates to prophylaxis of subjects who are believed to be at risk for cancer or have previously been diagnosed with cancer (or another disease). In one embodiment, said subjects can be administered the peptide vaccine described herein or pharmaceutical compositions thereof. The invention contemplates using any of the foreign peptides produced by the systems and methods described herein. In one embodiment, the foreign peptide vaccines described herein can be administered subcutaneously via syringe or any other suitable method know in the art.

The compound(s) or combination of compounds disclosed herein, or pharmaceutical compositions may be administered to a cell, mammal, or human by any suitable means. Non-limiting examples of methods of administration include, among others, (a) administration though oral pathways, which includes administration in capsule, tablet, granule, spray, syrup, or other such forms; (b) administration through non-oral pathways such as intraocular, intranasal, intraauricular, rectal, vaginal, intraurethral, transmucosal, buccal, or transdermal, which includes administration as an aqueous suspension, an oily preparation or the like or as a drip, spray, suppository, salve, ointment or the like; (c) administration via injection, including subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; (e) administration topically; as deemed appropriate by those of skill in the art for bringing the compound or combination of compounds disclosed herein into contact with living tissue; (f)

administration via inhalation, including through aerosolized, nebulized, and powdered formulations; and (g) administration through implantation.

As will be readily apparent to one skilled in the art, the effective in vivo dose to be administered and the particular mode of administration will vary depending upon the age, weight and species treated, and the specific use for which the compound or combination of compounds disclosed herein are employed. The determination of effective dose levels, that is the dose levels necessary to achieve the desired result, can be accomplished by one skilled in the art using routine pharmacological methods. Typically, human clinical applications of products are commenced at lower dose levels, with dose level being increased until the desired effect is achieved. Alternatively, acceptable in vitro studies can be used to establish useful doses and routes of administration of the compositions identified by the present methods using established pharmacological methods. Effective animal doses from in vivo studies can be converted to appropriate human doses using conversion methods known in the art (e.g., see Nair A B, Jacob S. A simple practice guide for dose conversion between animals and human. Journal of basic and clinical pharmacy. 2016 March; 7(2):27.)

Methods of Prevention

In some embodiments, the foreign peptides prepared using methods of the invention can be used as a vaccine to promote an immune response against cancer (e.g., against tumor neoantigens). In some embodiments, the invention provides compositions and methods for induction of immune response, for example induction of antibodies to tumor neoantigens. In some embodiments, the antibodies are broadly neutralizing antibodies. In some embodiments, the foreign peptides prepared using methods of the invention can be used as a vaccine to promote an immune response against a pathogen.

The compositions, systems, and methods disclosed herein are not to be limited in scope to the specific embodiments described herein. Indeed, various modifications of the compositions, systems, and methods in addition to those described will become apparent to those of skill in the art from the foregoing description.

What is claimed is:

1. A composition comprising nucleic acid sequences encoding two or more amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

2. The composition of claim 1, wherein the composition is immunogenic.

3. The composition of claim 1, wherein the nucleic acid sequence is administered in a construct for expression in vivo.

4. The composition of claim 3, wherein the in vivo administration of the nucleic acid sequence is configured to produce one or more peptides that are displayed by an HLA class I molecule.

5. The composition of claim 4, wherein the one or more peptides is a modified or unmodified fragment of a mutated KRAS protein.

6. The composition of claim 5, wherein the mutated KRAS protein is selected from the group consisting of KRAS G12D, KRAS G12V, and KRAS G12R.

7. The composition of claim 3, wherein the nucleic acid sequence is administered in an effective amount to a subject to prevent cancer.

8. The composition of claim 3, wherein the nucleic acid sequence is administered in an effective amount to a subject to treat cancer.

9. An immunogenic peptide composition comprising two or more peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

10. The immunogenic peptide composition of claim 9, wherein a peptide in the immunogenic peptide composition is displayed by an HLA class I molecule.

11. The immunogenic peptide composition of claim 9, wherein a peptide in the immunogenic peptide composition is a modified or unmodified fragment of a mutated KRAS protein.

12. The immunogenic peptide composition of claim 11, wherein the mutated KRAS protein is selected from the group consisting of KRAS G12D, KRAS G12V, and KRAS G12R.

13. The immunogenic peptide composition of claim 9, wherein the immunogenic peptide composition is administered in an effective amount to a subject to prevent cancer.

14. The immunogenic peptide composition of claim 9, wherein the immunogenic peptide composition is administered in an effective amount to a subject to treat cancer.

15. The immunogenic peptide composition of claim 9, wherein the immunogenic peptide composition comprises at least three peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

16. A nucleic acid sequence encoding one or more amino acid sequences selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

17. The nucleic acid sequence of claim 16, wherein the nucleic acid sequence is an immunogenic composition.

18. The nucleic acid sequence of claim 16, wherein the nucleic acid sequence is administered in a construct for expression in vivo.

19. The nucleic acid sequence of claim 18, wherein the in vivo administration of the nucleic acid sequence is configured to produce one or more peptides that are displayed by an HLA class II molecule.

20. The nucleic acid sequence of claim 16, wherein the one or more peptides is a modified fragment of a mutated KRAS protein.

21. The nucleic acid sequence of claim 19, wherein the mutated KRAS protein is selected from the group consisting of KRAS G12D, KRAS G12V, KRAS G12R, KRAS G12C, and KRAS G13D.

22. The nucleic acid sequence of claim 16, wherein the nucleic acid sequence is administered in an effective amount to a subject to prevent cancer.

23. The nucleic acid sequence of claim 16, wherein the nucleic acid sequence is administered in an effective amount to a subject to treat cancer.

24. An immunogenic peptide composition comprising one or more peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

25. The immunogenic peptide composition of claim 24, wherein a peptide in the immunogenic peptide composition is displayed by an HLA class II molecule.

26. The immunogenic peptide composition of claim 24, wherein a peptide in the immunogenic peptide composition is a modified or unmodified fragment of a mutated KRAS protein.

27. The immunogenic peptide composition of claim 26, wherein the mutated KRAS protein is selected from the group consisting of KRAS G12D, KRAS G12V, KRAS G12R, KRAS G12C, and KRAS G13D.

28. The immunogenic peptide composition of claim 24, wherein the immunogenic peptide composition is administered in an effective amount to a subject to prevent cancer.

29. The immunogenic peptide composition of claim 24, wherein the immunogenic peptide composition is administered in an effective amount to a subject to treat cancer.

30. The immunogenic peptide composition of claim 24, wherein the immunogenic peptide composition comprises at least two peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

* * * * *

SEQUENCE LISTING

```
<160> NUMBER OF SEQ ID NOS: 1523

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1

Gly Ala Asp Gly Val Gly Lys Ser Met
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 2

Leu Met Val Val Gly Ala Asp Gly Val
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 3

Gly Ala Val Gly Val Gly Lys Ser Leu
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 4

Leu Met Val Val Gly Ala Val Gly Val
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 5

Val Thr Gly Ala Arg Gly Val Gly Lys
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 6

Val Met Gly Ala Val Gly Val Gly Lys
1               5

<210> SEQ ID NO 7
<211> LENGTH: 9
<212> TYPE: PRT
<213> ORGANISM: Homo sapiens
<220> FEATURE:
<223> OTHER INFORMATION: Native (KRAS G12V)

<400> SEQUENCE: 7

Val Val Gly Ala Val Gly Val Gly Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 8

Gly Ala Arg Gly Val Gly Lys Ser Tyr
1               5

<210> SEQ ID NO 9
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 9

Gly Pro Arg Gly Val Gly Lys Ser Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 10

Leu Met Val Val Gly Ala Arg Gly Val
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 11

Gly Ala Asp Gly Val Gly Lys Ser Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 12

Gly Ala Asp Gly Val Gly Lys Ser Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 13

Gly Tyr Asp Gly Val Gly Lys Ser Met
1               5

<210> SEQ ID NO 14
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 14

Gly Pro Val Gly Val Gly Lys Ser Val
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 15

Leu Thr Val Val Gly Ala Val Gly Val
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 16

Val Val Gly Ala Val Gly Val Gly Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 17

Gly Ala Arg Gly Val Gly Lys Ser Met
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 18

Gly Pro Arg Gly Val Gly Lys Ser Val
1               5
```

```
<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 19

Leu Leu Val Val Gly Ala Arg Gly Val
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 20

Val Ala Gly Ala Arg Gly Val Gly Met
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 21

Leu Thr Val Val Gly Ala Asp Gly Val
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 22

Leu Leu Val Val Gly Ala Asp Gly Val
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 23

Leu Met Val Val Gly Ala Asp Gly Leu
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 24

Val Met Gly Ala Val Gly Val Gly Arg
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 25

Val Met Gly Ala Arg Gly Val Gly Lys
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 26

Gly Ala Cys Gly Val Gly Lys Ser Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 27

Leu Met Val Val Gly Ala Cys Gly Val
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 28

Leu Thr Val Val Gly Ala Cys Gly Val
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 29

Val Thr Gly Ala Cys Gly Val Gly Lys
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 30

Val Val Gly Ala Cys Gly Val Gly Arg
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 31

Ala Ala Asp Val Gly Lys Ser Ala Met
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 32

Ala Glu Asp Val Gly Lys Ser Ala Met
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 33

Ala Tyr Asp Val Gly Lys Ser Ala Met
```

-continued

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 34

Asp Ala Gly Lys Ser Ala Leu Thr Val
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 35

Gly Ala Gly Asp Val Gly Lys Ser Met
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 36

Leu Gln Val Val Gly Ala Cys Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 37

Val Met Gly Ala Cys Gly Val Gly Lys
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 38

```
Val Met Gly Ala Cys Gly Val Gly Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 39

Ala Ala Asp Val Gly Lys Ser Ala Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 40

Ala Ser Asp Val Gly Lys Ser Ala Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 41

Ala Ser Asp Val Gly Lys Ser Ala Met
1               5

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGADGVGKS (KRAS G12D)

<400> SEQUENCE: 42

Glu Tyr Lys Phe Val Val Phe Gly Ser Asp Gly Ala Gly Lys Ser
1               5                   10                  15

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGADGVGKSALTIQLIQN (KRAS G12D)

<400> SEQUENCE: 43
```

```
Glu Tyr Lys Phe Val Val Ile Gly Asn Asp Gly Ala Gly Lys Ser Ala
1               5                   10                  15

Leu Thr Ile Gln Leu Ile Gln Asn
            20

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGADGVGKS (KRAS G12D)

<400> SEQUENCE: 44

Glu Tyr Lys Phe Val Val Leu Gly Ala Asp Gly Ala Gly Lys Ser
1               5                   10                  15

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: MTEYKLVVVGADGVGKSALT (KRAS G12D)

<400> SEQUENCE: 45

Met Thr Glu Tyr Lys Phe Val Val Ser Gly Ala Asp Gly Ile Gly Lys
1               5                   10                  15

Ser Ala Leu Thr
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: MTEYKLVVVGADGVGKSALT (KRAS G12D)

<400> SEQUENCE: 46

Met Thr Glu Tyr Lys Phe Val Val Tyr Gly Ser Asp Gly Ile Gly Lys
1               5                   10                  15

Ser Ala Leu Thr
            20

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGAVGVGKS (KRAS G12V)

<400> SEQUENCE: 47

Glu Tyr Lys Phe Val Val Ile Gly Arg Val Gly His Gly Lys Ser
1               5                   10                  15

<210> SEQ ID NO 48
```

-continued

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGAVGVGKS (KRAS G12V)

<400> SEQUENCE: 48

Glu Tyr Lys Phe Val Val Leu Gly Thr Val Gly His Gly Lys Ser
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGAVGVGKS (KRAS G12V)

<400> SEQUENCE: 49

Glu Tyr Lys Phe Val Val Tyr Gly Asn Val Gly Met Gly Lys Ser
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGAVGVGKS (KRAS G12V)

<400> SEQUENCE: 50

Glu Tyr Lys Ile Val Val Ala Gly Asn Val Gly Ile Gly Lys Ser
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: TEYKLVVVGAVGVGK (KRAS G12V)

<400> SEQUENCE: 51

Thr Glu Tyr Lys Ile Val Val Met Gly Asn Val Gly Tyr Gly Lys
1               5                   10                  15

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: MTEYKLVVVGARGVGKSALT (KRAS G12R)

<400> SEQUENCE: 52

Met Thr Glu Tyr Lys Phe Val Val Phe Gly Ser Arg Gly Val Gly Lys
1               5                   10                  15

Ser Ala Leu Thr
```

```
                    20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: MTEYKLVVVGARGVGKSALT (KRAS G12R)

<400> SEQUENCE: 53

Met Thr Glu Tyr Lys Phe Val Val Ile Gly Asn Arg Gly Val Gly Lys
1               5                   10                  15

Ser Ala Leu Thr
            20

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: MTEYKLVVVGARGVGKSALT (KRAS G12R)

<400> SEQUENCE: 54

Met Thr Glu Tyr Lys Phe Val Val Ile Gly Val Arg Gly Asp Gly Lys
1               5                   10                  15

Ser Ala Leu Thr
            20

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: MTEYKLVVVGARGVGKSALT (KRAS G12R)

<400> SEQUENCE: 55

Met Thr Glu Tyr Lys Phe Val Val Met Gly Ser Arg Gly Ala Gly Lys
1               5                   10                  15

Ser Ala Leu Thr
            20

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVVGARGVGKSALTI (KRAS G12R)

<400> SEQUENCE: 56

Val Val Val Ile Ala Arg Gly Val Pro Lys Ser Leu Leu Thr Ile
1               5                   10                  15

<210> SEQ ID NO 57
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGACGVGKS (KRAS G12C)

<400> SEQUENCE: 57

Glu Tyr Lys Phe Val Val Phe Gly Asn Cys Gly Ala Gly Lys Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGACGVGKS (KRAS G12C)

<400> SEQUENCE: 58

Glu Tyr Lys Phe Val Val Ser Gly Ala Cys Gly Val Gly Lys Ser
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGACGVGKS (KRAS G12C)

<400> SEQUENCE: 59

Glu Tyr Lys Phe Val Val Ser Gly Asn Cys Gly Leu Gly Lys Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGACGVGKS (KRAS G12C)

<400> SEQUENCE: 60

Glu Tyr Lys Leu Val Val Met Gly Pro Cys Gly Ala Gly Lys Ser
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: KLVVVGACGVGKSAL (KRAS G12C)

<400> SEQUENCE: 61

Lys Leu Val Ile Val Gly Ile Cys Lys Val Gly His Ser Ala Leu
1               5                   10                  15

<210> SEQ ID NO 62
<211> LENGTH: 15
```

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGAGDVGKS (KRAS G13D)

<400> SEQUENCE: 62

Glu Tyr Lys Phe Val Val Phe Gly Asn Gly Asp Leu Gly Lys Ser
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGAGDVGKS (KRAS G13D)

<400> SEQUENCE: 63

Glu Tyr Lys Phe Val Val Met Gly Asn Gly Asp Ser Gly Lys Ser
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGAGDVGKS (KRAS G13D)

<400> SEQUENCE: 64

Glu Tyr Lys Phe Val Val Ser Gly Ser Gly Asp Val Gly Lys Ser
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: EYKLVVVGAGDVGKS (KRAS G13D)

<400> SEQUENCE: 65

Glu Tyr Lys Ile Val Val Met Gly Arg Gly Asp Met Gly Lys Ser
1               5                   10                  15

<210> SEQ ID NO 66
<211> LENGTH: 15
<212> TYPE: PRT
<213> ORGANISM: Homo sapiens
<220> FEATURE:
<223> OTHER INFORMATION: Native (KRAS G13D)

<400> SEQUENCE: 66

Tyr Lys Leu Val Val Val Gly Ala Gly Asp Val Gly Lys Ser Ala
1               5                   10                  15

<210> SEQ ID NO 67
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 67

Leu Leu Val Val Gly Ala Cys Gly Val
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 68

Leu Leu Val Val Gly Ala Val Gly Val
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 69

Leu Met Val Val Gly Ala Val Gly Ile
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 70

Leu Met Val Val Gly Ala Cys Gly Ile
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 71

Leu Leu Val Val Gly Ala Cys Gly Ile
1               5

<210> SEQ ID NO 72
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 72

Leu Met Val Val Gly Ala Val Gly Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 73

Leu Met Val Val Gly Ala Cys Gly Leu
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 74

Leu Leu Val Val Gly Ala Cys Gly Leu
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 75

Leu Ile Val Val Gly Ala Cys Gly Val
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 76

Leu Leu Val Val Gly Ala Val Gly Ile
1               5

<210> SEQ ID NO 77
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 77

Ala Thr Asp Val Gly Lys Ser Ala Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 78

Leu Met Val Val Gly Ala Cys Gly Ala
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 79

Ala Ile Asp Val Gly Lys Ser Ala Leu
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 80

Ala Val Asp Val Gly Lys Ser Ala Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 81

Ala Phe Asp Val Gly Lys Ser Ala Leu
1               5

<210> SEQ ID NO 82
```

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 82

Ala Ala Asp Val Gly Lys Ser Ala Val
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 83

Leu Met Val Val Gly Ala Val Gly Ala
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 84

Ala Ala Asp Val Gly Lys Ser Ala Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 85

Ala Phe Asp Val Gly Lys Ser Ala Met
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 86

Gly Thr Asp Gly Val Gly Lys Ser Leu
1               5
```

```
<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 87

Ala Tyr Asp Val Gly Lys Ser Ala Leu
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 88

Gly Ser Asp Gly Val Gly Lys Ser Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 89

Ala Thr Asp Val Gly Lys Ser Ala Met
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 90

Leu Leu Val Val Gly Ala Val Gly Leu
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 91

Ala Ile Asp Val Gly Lys Ser Ala Met
1               5
```

```
<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 92

Ala Leu Asp Val Gly Lys Ser Ala Leu
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 93

Ala Trp Asp Val Gly Lys Ser Ala Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 94

Leu Ile Val Val Gly Ala Val Gly Val
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 95

Ala Thr Asp Val Gly Lys Ser Ala Ile
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 96

Ala Val Asp Val Gly Lys Ser Ala Met
1               5
```

```
<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 97

Gly Ile Asp Gly Val Gly Lys Ser Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 98

Gly Val Asp Gly Val Gly Lys Ser Leu
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 99

Ala Thr Asp Val Gly Lys Ser Ala Val
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 100

Ala Ser Asp Val Gly Lys Ser Ala Val
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 101

Gly Pro Arg Gly Val Gly Lys Ser Leu
```

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 102

Ala Ser Asp Val Gly Lys Ser Ala Ile
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 103

Ala Phe Asp Val Gly Lys Ser Ala Phe
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 104

Gly Thr Asp Gly Val Gly Lys Ser Met
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 105

Gly Ser Asp Gly Val Gly Lys Ser Met
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 106

-continued

Ala Ile Asp Val Gly Lys Ser Ala Val
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 107

Ala Val Asp Val Gly Lys Ser Ala Ile
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 108

Ala Ile Asp Val Gly Lys Ser Ala Ile
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 109

Leu Leu Val Val Gly Ala Cys Gly Ala
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 110

Ala Ala Asp Val Gly Lys Ser Ala Phe
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 111

```
Ala Val Asp Val Gly Lys Ser Ala Val
1               5
```

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 112

```
Gly Leu Asp Gly Val Gly Lys Ser Leu
1               5
```

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 113

```
Gly Pro Arg Gly Val Gly Lys Ser Met
1               5
```

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 114

```
Ala Trp Asp Val Gly Lys Ser Ala Met
1               5
```

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 115

```
Ala Leu Asp Val Gly Lys Ser Ala Met
1               5
```

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

```
<400> SEQUENCE: 116

Gly Ala Asp Gly Val Gly Lys Ser Val
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 117

Ala Met Asp Val Gly Lys Ser Ala Leu
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 118

Gly Ala Val Gly Val Gly Lys Ser Tyr
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 119

Ala Phe Asp Val Gly Lys Ser Ala Ile
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 120

Val Thr Gly Ala Val Gly Val Gly Arg
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)
```

<400> SEQUENCE: 121

Gly Ile Asp Gly Val Gly Lys Ser Met
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 122

Leu Gln Val Val Gly Ala Val Gly Val
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 123

Gly Ala Asp Gly Val Gly Lys Ser Ile
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 124

Gly Val Asp Gly Val Gly Lys Ser Met
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 125

Leu Met Val Val Gly Ala Asp Gly Ile
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: AGDVGKSAL (KRAS G13D)

<400> SEQUENCE: 126

Ala Ile Asp Val Gly Lys Ser Ala Phe
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 127

Gly Ala Asp Gly Val Gly Lys Ser Phe
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 128

Ala Tyr Asp Val Gly Lys Ser Ala Phe
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 129

Gly Leu Asp Gly Val Gly Lys Ser Met
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 130

Ala Phe Asp Val Gly Lys Ser Ala Val
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: Seed: GAVGVGKSA (KRAS G12V)

<400> SEQUENCE: 131

Gly Ala Val Gly Val Gly Lys Ser Met
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 132

Gly Pro Arg Gly Val Gly Lys Ser Ile
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 133

Ala Thr Asp Val Gly Lys Ser Ala Phe
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 134

Gly Met Asp Gly Val Gly Lys Ser Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 135

Gly Thr Asp Gly Val Gly Lys Ser Ile
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<223> OTHER INFORMATION: Seed: AGDVGKSAL (KRAS G13D)

<400> SEQUENCE: 136

Ala Val Asp Val Gly Lys Ser Ala Phe
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 137

Ala Gly Asp Val Gly Lys Ser Ala Met
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 138

Gly Pro Val Gly Val Gly Lys Ser Ala
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 139

Gly Thr Asp Gly Val Gly Lys Ser Val
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 140

Ala Ser Asp Val Gly Lys Ser Ala Phe
1               5

<210> SEQ ID NO 141
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 141

Gly Ser Asp Gly Val Gly Lys Ser Val
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 142

Val Thr Gly Ala Val Gly Val Gly Lys
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 143

Gly Ser Asp Gly Val Gly Lys Ser Ile
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 144

Ala Trp Asp Val Gly Lys Ser Ala Phe
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 145

Gly Ala Gly Asp Val Gly Lys Ser Tyr
1               5

<210> SEQ ID NO 146
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 146

Gly Ser Asp Gly Val Gly Lys Ser Phe
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 147

Gly Thr Asp Gly Val Gly Lys Ser Phe
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 148

Ala Met Asp Val Gly Lys Ser Ala Met
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 149

Gly Val Asp Gly Val Gly Lys Ser Ile
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 150

Ala Leu Asp Val Gly Lys Ser Ala Val
1               5

<210> SEQ ID NO 151
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 151

Ala Tyr Asp Val Gly Lys Ser Ala Ile
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 152

Gly Ala Val Gly Val Gly Lys Ser Phe
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 153

Ala Leu Asp Val Gly Lys Ser Ala Ile
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 154

Leu Leu Val Val Gly Ala Asp Gly Leu
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 155

Gly Ile Asp Gly Val Gly Lys Ser Phe
1               5

<210> SEQ ID NO 156
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 156

Gly Met Asp Gly Val Gly Lys Ser Met
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 157

Gly Ile Asp Gly Val Gly Lys Ser Ile
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 158

Gly Val Asp Gly Val Gly Lys Ser Phe
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 159

Gly Ile Asp Gly Val Gly Lys Ser Val
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 160

Gly Val Asp Gly Val Gly Lys Ser Val
1               5

<210> SEQ ID NO 161
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 161

Gly Ala Gly Asp Val Gly Lys Ser Leu
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 162

Leu Ile Val Val Gly Ala Asp Gly Val
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 163

Val Ala Gly Ala Val Gly Val Gly Tyr
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 164

Ala Tyr Asp Val Gly Lys Ser Ala Val
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 165

Gly Ala Arg Gly Val Gly Lys Ser Phe
1               5
```

```
<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 166

Ala Trp Asp Val Gly Lys Ser Ala Ile
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 167

Gly Gly Asp Gly Val Gly Lys Ser Leu
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 168

Gly Pro Arg Gly Val Gly Lys Ser Phe
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 169

Val Ala Gly Ala Val Gly Val Gly Leu
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 170

Gly Ser Val Gly Val Gly Lys Ser Tyr
1               5
```

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 171

Gly Ala Cys Gly Val Gly Lys Ser Tyr
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 172

Ala Gly Asp Val Gly Lys Ser Ala Val
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 173

Ala Leu Asp Val Gly Lys Ser Ala Phe
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 174

Ala Gly Asp Val Gly Lys Ser Ala Ile
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 175

Gly Ala Gly Asp Val Gly Lys Ser Phe
1               5

```
<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 176

Gly Pro Cys Gly Val Gly Lys Ser Ala
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 177

Asp Val Gly Lys Ser Ala Leu Thr Phe
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 178

Ala Trp Asp Val Gly Lys Ser Ala Val
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 179

Leu Leu Val Val Gly Ala Val Gly Ala
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 180

Gly Tyr Asp Gly Val Gly Lys Ser Leu
```

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: VVGARGVGK (KRAS G12R)

<400> SEQUENCE: 181

Val Ala Gly Ala Arg Gly Val Gly Leu
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: GARGVGKSA (KRAS G12R)

<400> SEQUENCE: 182

Gly Ser Arg Gly Val Gly Lys Ser Tyr
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: AGDVGKSAL (KRAS G13D)

<400> SEQUENCE: 183

Ala Met Asp Val Gly Lys Ser Ala Val
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: AGDVGKSAL (KRAS G13D)

<400> SEQUENCE: 184

Ala Met Asp Val Gly Lys Ser Ala Ile
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: DVGKSALTI (KRAS G13D)

<400> SEQUENCE: 185

Asp Val Gly Lys Ser Ala Leu Thr Trp
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 186

Ala Asn Asp Val Gly Lys Ser Ala Leu
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 187

Gly Ala Cys Gly Val Gly Lys Ser Met
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 188

Ala Gln Asp Val Gly Lys Ser Ala Leu
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 189

Gly Ser Val Gly Val Gly Lys Ser Leu
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 190

```
Gly Gly Asp Gly Val Gly Lys Ser Met
1               5
```

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 191

```
Ala Gly Asp Val Gly Lys Ser Ala Phe
1               5
```

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 192

```
Gly Thr Val Gly Val Gly Lys Ser Tyr
1               5
```

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 193

```
Gly Leu Asp Gly Val Gly Lys Ser Phe
1               5
```

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 194

```
Leu Gln Val Val Gly Ala Asp Gly Val
1               5
```

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

```
<400> SEQUENCE: 195

Gly Ala Arg Gly Val Gly Lys Ser Leu
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 196

Gly Ser Val Gly Val Gly Lys Ser Phe
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 197

Ala Cys Asp Val Gly Lys Ser Ala Leu
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 198

Val Ala Gly Ala Val Gly Val Gly Met
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 199

Ala Glu Asp Val Gly Lys Ser Ala Leu
1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)
```

```
<400> SEQUENCE: 200

Leu Leu Val Val Gly Ala Asp Gly Ile
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 201

Ala Glu Asp Val Gly Lys Ser Ala Phe
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 202

Gly Leu Asp Gly Val Gly Lys Ser Val
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 203

Val Ala Gly Ala Val Gly Val Gly Arg
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 204

Val Ala Gly Ala Val Gly Val Gly Phe
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Seed: GADGVGKSA (KRAS G12D)

<400> SEQUENCE: 205

Gly Leu Asp Gly Val Gly Lys Ser Ile
1               5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 206

Val Thr Gly Ala Cys Gly Val Gly Arg
1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 207

Ala Ala Asp Val Gly Lys Ser Ala Tyr
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 208

Gly Val Arg Gly Val Gly Lys Ser Tyr
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 209

Gly Phe Asp Gly Val Gly Lys Ser Leu
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: GAVGVGKSA (KRAS G12V)

<400> SEQUENCE: 210

Gly Val Val Gly Val Gly Lys Ser Tyr
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 211

Gly Ser Arg Gly Val Gly Lys Ser Phe
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 212

Leu Met Val Val Gly Ala Arg Gly Ile
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 213

Gly Ala Cys Gly Val Gly Lys Ser Phe
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 214

Gly Thr Val Gly Val Gly Lys Ser Phe
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: Seed: DVGKSALTI (KRAS G13D)

<400> SEQUENCE: 215

Asp Ala Gly Lys Ser Ala Leu Thr Ile
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 216

Ala Gln Asp Val Gly Lys Ser Ala Met
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 217

Ala Asn Asp Val Gly Lys Ser Ala Met
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 218

Ala Tyr Asp Val Gly Lys Ser Ala Tyr
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 219

Gly Thr Arg Gly Val Gly Lys Ser Tyr
1               5

<210> SEQ ID NO 220
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 220

Gly Pro Gly Asp Val Gly Lys Ser Ala
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 221

Gly Met Asp Gly Val Gly Lys Ser Val
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 222

Gly Val Arg Gly Val Gly Lys Ser Phe
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 223

Val Ser Gly Ala Val Gly Val Gly Arg
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 224

Gly Phe Asp Gly Val Gly Lys Ser Met
1               5

<210> SEQ ID NO 225
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 225

Ala Met Asp Val Gly Lys Ser Ala Phe
1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 226

Gly Cys Asp Gly Val Gly Lys Ser Leu
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 227

Gly Val Gly Asp Val Gly Lys Ser Tyr
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 228

Gly Thr Arg Gly Val Gly Lys Ser Phe
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 229

Gly Ile Arg Gly Val Gly Lys Ser Tyr
1               5

<210> SEQ ID NO 230
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 230

Gly Met Asp Gly Val Gly Lys Ser Ile
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 231

Ala Cys Asp Val Gly Lys Ser Ala Met
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 232

Gly Ser Gly Asp Val Gly Lys Ser Tyr
1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 233

Gly Ala Val Gly Val Gly Lys Ser Val
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 234

Gly Ser Val Gly Val Gly Lys Ser Met
1               5

<210> SEQ ID NO 235
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 235

Asp Val Gly Lys Ser Ala Leu Thr Tyr
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 236

Gly Val Val Gly Val Gly Lys Ser Phe
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 237

Gly Ile Val Gly Val Gly Lys Ser Tyr
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 238

Val Ala Gly Ala Cys Gly Val Gly Tyr
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 239

Gly Ser Cys Gly Val Gly Lys Ser Tyr
1               5

<210> SEQ ID NO 240
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 240

Gly Thr Val Gly Val Gly Lys Ser Leu
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 241

Gly Ala Val Gly Val Gly Lys Ser His
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 242

Gly Met Asp Gly Val Gly Lys Ser Phe
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 243

Gly Gln Asp Gly Val Gly Lys Ser Leu
1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 244

Gly Cys Asp Gly Val Gly Lys Ser Met
1               5
```

```
<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 245

Gly Ser Gly Asp Val Gly Lys Ser Phe
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 246

Gly Thr Gly Asp Val Gly Lys Ser Tyr
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 247

Gly Gly Asp Gly Val Gly Lys Ser Ile
1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 248

Ala Cys Asp Val Gly Lys Ser Ala Val
1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 249

Gly Ser Arg Gly Val Gly Lys Ser Met
1               5
```

```
<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 250

Val Ser Gly Ala Val Gly Val Gly Lys
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 251

Gly Tyr Asp Gly Val Gly Lys Ser Phe
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 252

Asp Thr Gly Lys Ser Ala Leu Thr Phe
1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 253

Gly Pro Arg Gly Val Gly Lys Ser Pro
1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 254

Gly Pro Val Gly Val Gly Lys Ser Leu
1               5
```

```
<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 255

Gly Gly Asp Gly Val Gly Lys Ser Phe
1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 256

Gly Pro Cys Gly Val Gly Lys Ser Val
1               5

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 257

Gly Val Gly Asp Val Gly Lys Ser Phe
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 258

Gly Ile Gly Asp Val Gly Lys Ser Tyr
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 259

Gly Gly Val Gly Val Gly Lys Ser Tyr
```

-continued

```
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 260

Gly Pro Arg Gly Val Gly Lys Ser Thr
1               5

<210> SEQ ID NO 261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 261

Gly Gly Asp Gly Val Gly Lys Ser Val
1               5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 262

Ala Cys Asp Val Gly Lys Ser Ala Phe
1               5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 263

Gly Ala Val Gly Val Gly Lys Ser Ile
1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 264
```

```
Gly Ile Arg Gly Val Gly Lys Ser Phe
1               5
```

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 265

```
Gly Thr Gly Asp Val Gly Lys Ser Phe
1               5
```

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 266

```
Gly Asn Asp Gly Val Gly Lys Ser Leu
1               5
```

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 267

```
Val Ala Gly Ala Arg Gly Val Gly Phe
1               5
```

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 268

```
Gly Val Cys Gly Val Gly Lys Ser Tyr
1               5
```

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 269

```
Gly Val Arg Gly Val Gly Lys Ser Met
1               5
```

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 270

```
Val Thr Gly Ala Arg Gly Val Gly Arg
1               5
```

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 271

```
Val Ala Gly Ala Val Gly Val Gly Lys
1               5
```

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 272

```
Val Ala Gly Ala Asp Gly Val Gly Tyr
1               5
```

<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 273

```
Gly Gln Asp Gly Val Gly Lys Ser Met
1               5
```

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

```
<400> SEQUENCE: 274

Gly Pro Val Gly Val Gly Lys Ser Thr
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 275

Ala Glu Asp Val Gly Lys Ser Ala Ile
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 276

Val Ile Gly Ala Val Gly Val Gly Lys
1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 277

Gly Val Val Gly Val Gly Lys Ser Leu
1               5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 278

Gly Val Val Gly Val Gly Lys Ser Met
1               5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)
```

<400> SEQUENCE: 279

Val Ala Gly Ala Arg Gly Val Gly Tyr
1               5

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 280

Gly Thr Val Gly Val Gly Lys Ser Met
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 281

Ala Cys Asp Val Gly Lys Ser Ala Ile
1               5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 282

Gly Pro Arg Gly Val Gly Lys Ser Cys
1               5

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 283

Leu Leu Val Val Gly Ala Arg Gly Ile
1               5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: GARGVGKSA (KRAS G12R)

<400> SEQUENCE: 284

Gly Val Arg Gly Val Gly Lys Ser Leu
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 285

Gly Thr Cys Gly Val Gly Lys Ser Tyr
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 286

Gly Pro Val Gly Val Gly Lys Ser Pro
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 287

Val Ser Gly Ala Val Gly Val Gly Tyr
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 288

Gly Phe Asp Gly Val Gly Lys Ser Val
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: DVGKSALTI (KRAS G13D)

<400> SEQUENCE: 289

Asp Ile Gly Lys Ser Ala Leu Thr Trp
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 290

Gly Tyr Asp Gly Val Gly Lys Ser Ile
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 291

Gly Ala Arg Gly Val Gly Lys Ser Val
1               5

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 292

Gly Pro Asp Gly Val Gly Lys Ser Ala
1               5

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 293

Gly Gly Arg Gly Val Gly Lys Ser Tyr
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                    peptide
<220> FEATURE:
<223> OTHER INFORMATION: Seed: GARGVGKSA (KRAS G12R)

<400> SEQUENCE: 294

Gly Thr Arg Gly Val Gly Lys Ser Met
1               5

<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 295

Gly Ile Val Gly Val Gly Lys Ser Phe
1               5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 296

Ala Glu Asp Val Gly Lys Ser Ala Val
1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 297

Gly Pro Val Gly Val Gly Lys Ser Ile
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 298

Ala Asp Asp Val Gly Lys Ser Ala Phe
1               5

<210> SEQ ID NO 299
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 299

Gly Ser Cys Gly Val Gly Lys Ser Phe
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 300

Ala Arg Asp Val Gly Lys Ser Ala Leu
1               5

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 301

Gly Ser Gly Asp Val Gly Lys Ser Met
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 302

Ala Gln Asp Val Gly Lys Ser Ala Ile
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 303

Gly Val Gly Asp Val Gly Lys Ser Met
1               5

<210> SEQ ID NO 304
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 304

Gly Phe Asp Gly Val Gly Lys Ser Phe
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 305

Gly Ser Arg Gly Val Gly Lys Ser Leu
1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 306

Ala Asn Asp Val Gly Lys Ser Ala Ile
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 307

Gly Pro Val Gly Val Gly Lys Ser Met
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 308

Gly Asn Asp Gly Val Gly Lys Ser Met
1               5

<210> SEQ ID NO 309
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 309

Val Leu Gly Ala Val Gly Val Gly Arg
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 310

Leu Met Val Val Gly Ala Arg Gly Leu
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 311

Ala Asn Asp Val Gly Lys Ser Ala Val
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 312

Gly Trp Asp Gly Val Gly Lys Ser Leu
1               5

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 313

Val Ala Gly Ala Cys Gly Val Gly Arg
1               5

<210> SEQ ID NO 314
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 314

Ala Asp Asp Val Gly Lys Ser Ala Leu
1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 315

Gly Ser Cys Gly Val Gly Lys Ser Leu
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 316

Asp Ala Gly Lys Ser Ala Leu Thr Leu
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 317

Ala Gln Asp Val Gly Lys Ser Ala Val
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 318

Val Thr Gly Ala Gly Asp Val Gly Arg
1               5

<210> SEQ ID NO 319
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 319

Val Thr Gly Ala Asp Gly Val Gly Arg
1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 320

Val Thr Gly Ala Val Gly Val Gly Tyr
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 321

Val Val Gly Ala Val Gly Val Gly Tyr
1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 322

Val Ile Gly Ala Val Gly Val Gly Arg
1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 323

Gly Ile Cys Gly Val Gly Lys Ser Tyr
1               5
```

```
<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 324

Val Val Gly Ala Arg Gly Val Gly Arg
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 325

Gly Ile Gly Asp Val Gly Lys Ser Phe
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 326

Val Met Gly Ala Arg Gly Val Gly Arg
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 327

Val Ala Gly Ala Cys Gly Val Gly Phe
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 328

Ala Gln Asp Val Gly Lys Ser Ala Phe
1               5
```

```
<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 329

Ala Val Asp Val Gly Lys Ser Ala Tyr
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 330

Val Ala Gly Ala Gly Asp Val Gly Tyr
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 331

Asp Pro Gly Lys Ser Ala Leu Thr Val
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 332

Gly Cys Asp Gly Val Gly Lys Ser Val
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 333

Gly Phe Asp Gly Val Gly Lys Ser Ile
1               5
```

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 334

Gly Ile Arg Gly Val Gly Lys Ser Met
1               5

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 335

Gly Cys Asp Gly Val Gly Lys Ser Phe
1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 336

Val Ala Gly Ala Cys Gly Val Gly Leu
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 337

Leu Val Val Val Gly Ala Cys Gly Ile
1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 338

Ala Ser Asp Val Gly Lys Ser Ala Tyr

```
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 339

Gly Tyr Asp Gly Val Gly Lys Ser Val
1               5

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 340

Ala Asp Asp Val Gly Lys Ser Ala Met
1               5

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 341

Asp Thr Gly Lys Ser Ala Leu Thr Trp
1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 342

Gly Pro Cys Gly Val Gly Lys Ser Leu
1               5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 343
```

-continued

Gly Arg Asp Gly Val Gly Lys Ser Leu
1               5

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 344

Gly Val Cys Gly Val Gly Lys Ser Phe
1               5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 345

Gly Leu Arg Gly Val Gly Lys Ser Tyr
1               5

<210> SEQ ID NO 346
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 346

Gly Ala Cys Gly Val Gly Lys Ser Val
1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 347

Gly Thr Cys Gly Val Gly Lys Ser Phe
1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 348

Gly Ser Asp Gly Val Gly Lys Ser Tyr
1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 349

Gly Ala Cys Gly Val Gly Lys Ser Ile
1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 350

Gly Thr Gly Asp Val Gly Lys Ser Met
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 351

Val Ser Gly Ala Arg Gly Val Gly Met
1               5

<210> SEQ ID NO 352
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 352

Val Thr Gly Ala Asp Gly Val Gly Lys
1               5

<210> SEQ ID NO 353
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

```
<400> SEQUENCE: 353

Val Leu Gly Ala Val Gly Val Gly Lys
1               5

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 354

Ala Arg Asp Val Gly Lys Ser Ala Tyr
1               5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 355

Gly Ser Gly Asp Val Gly Lys Ser Leu
1               5

<210> SEQ ID NO 356
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 356

Val Val Gly Ala Gly Asp Val Gly Arg
1               5

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 357

Gly Pro Gly Asp Val Gly Lys Ser Val
1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)
```

<400> SEQUENCE: 358

Asp Thr Gly Lys Ser Ala Leu Thr Tyr
1               5

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 359

Ala Arg Asp Val Gly Lys Ser Ala Phe
1               5

<210> SEQ ID NO 360
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 360

Gly Ser Cys Gly Val Gly Lys Ser Met
1               5

<210> SEQ ID NO 361
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 361

Ala Thr Asp Val Gly Lys Ser Ala Tyr
1               5

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 362

Gly Met Arg Gly Val Gly Lys Ser Tyr
1               5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: GAGDVGKSA (KRAS G13D)

<400> SEQUENCE: 363

Gly Ala Gly Asp Val Gly Lys Ser His
1               5

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 364

Gly Cys Asp Gly Val Gly Lys Ser Ile
1               5

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 365

Gly Ala Arg Gly Val Gly Lys Ser Ile
1               5

<210> SEQ ID NO 366
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 366

Val Val Gly Ala Asp Gly Val Gly Arg
1               5

<210> SEQ ID NO 367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 367

Ala Asn Asp Val Gly Lys Ser Ala Phe
1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: VVGACGVGK (KRAS G12C)

<400> SEQUENCE: 368

Val Ser Gly Ala Cys Gly Val Gly Lys
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 369

Val Ser Gly Ala Val Gly Val Gly Phe
1               5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 370

Gly Trp Asp Gly Val Gly Lys Ser Met
1               5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 371

Gly Thr Arg Gly Val Gly Lys Ser Leu
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 372

Gly Ile Val Gly Val Gly Lys Ser Met
1               5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
          peptide
<220> FEATURE:
<223> OTHER INFORMATION: Seed: VVGACGVGK (KRAS G12C)

<400> SEQUENCE: 373

Val Ile Gly Ala Cys Gly Val Gly Lys
1               5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 374

Gly Ala Gly Asp Val Gly Lys Ser Val
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 375

Gly Gly Gly Asp Val Gly Lys Ser Tyr
1               5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 376

Leu Gln Val Val Gly Ala Cys Gly Leu
1               5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 377

Gly Val Gly Asp Val Gly Lys Ser Leu
1               5

<210> SEQ ID NO 378
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 378

Val Ala Gly Ala Asp Gly Val Gly Phe
1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 379

Gly Ala Arg Gly Val Gly Lys Ser His
1               5

<210> SEQ ID NO 380
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 380

Gly Val Asp Gly Val Gly Lys Ser Tyr
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 381

Val Ala Gly Ala Cys Gly Val Gly Met
1               5

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 382

Gly Pro Cys Gly Val Gly Lys Ser Met
1               5

<210> SEQ ID NO 383
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 383

Val Thr Gly Ala Asp Gly Val Gly Tyr
1               5

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 384

Ala Ala Asp Val Gly Lys Ser Ala Ala
1               5

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 385

Gly Gly Cys Gly Val Gly Lys Ser Tyr
1               5

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 386

Gly Ser Val Gly Val Gly Lys Ser His
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 387

Ala Ala Asp Val Gly Lys Ser Ala Cys
1               5

<210> SEQ ID NO 388
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 388

Asp Ile Gly Lys Ser Ala Leu Thr Phe
1               5

<210> SEQ ID NO 389
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 389

Val Ala Gly Ala Val Gly Val Gly His
1               5

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 390

Gly Gln Arg Gly Val Gly Lys Ser Tyr
1               5

<210> SEQ ID NO 391
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 391

Ala Phe Asp Val Gly Lys Ser Ala Tyr
1               5

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 392

Val Ser Gly Ala Arg Gly Val Gly Leu
1               5

<210> SEQ ID NO 393
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 393

Gly Pro Cys Gly Val Gly Lys Ser Ile
1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 394

Gly Gln Val Gly Val Gly Lys Ser Tyr
1               5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 395

Val Thr Gly Ala Cys Gly Val Gly Tyr
1               5

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 396

Gly Pro Cys Gly Val Gly Lys Ser Pro
1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 397

Val Ser Gly Ala Cys Gly Val Gly Arg
1               5

<210> SEQ ID NO 398
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 398

Gly Ile Gly Asp Val Gly Lys Ser Met
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 399

Leu Met Val Val Gly Ala Val Gly Met
1               5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 400

Ala Arg Asp Val Gly Lys Ser Ala Met
1               5

<210> SEQ ID NO 401
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 401

Leu Gln Val Val Gly Ala Val Gly Leu
1               5

<210> SEQ ID NO 402
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 402

Gly Ala Cys Gly Val Gly Lys Ser His
1               5
```

```
<210> SEQ ID NO 403
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 403

Gly Val Cys Gly Val Gly Lys Ser Met
1               5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 404

Leu Leu Val Val Gly Ala Arg Gly Leu
1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 405

Gly Thr Cys Gly Val Gly Lys Ser Leu
1               5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 406

Ala Phe Asp Val Gly Lys Ser Ala Cys
1               5

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 407

Gly Leu Val Gly Val Gly Lys Ser Tyr
1               5
```

```
<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 408

Gly Met Val Gly Val Gly Lys Ser Tyr
1               5

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 409

Val Ser Gly Ala Arg Gly Val Gly Phe
1               5

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 410

Val Leu Gly Ala Cys Gly Val Gly Lys
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 411

Gly Thr Cys Gly Val Gly Lys Ser Met
1               5

<210> SEQ ID NO 412
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 412

Gly Thr Asp Gly Val Gly Lys Ser Tyr
1               5
```

```
<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 413

Gly Gly Val Gly Val Gly Lys Ser Phe
1               5

<210> SEQ ID NO 414
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 414

Gly Thr Gly Asp Val Gly Lys Ser Leu
1               5

<210> SEQ ID NO 415
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 415

Leu Ile Val Val Gly Ala Cys Gly Ile
1               5

<210> SEQ ID NO 416
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 416

Val Leu Gly Ala Arg Gly Val Gly Lys
1               5

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 417

Leu Met Val Val Gly Ala Arg Gly Ala
```

```
<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 418

Gly Pro Cys Gly Val Gly Lys Ser Thr
1               5

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 419

Val Ile Gly Ala Val Gly Val Gly Tyr
1               5

<210> SEQ ID NO 420
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 420

Gly Pro Arg Gly Val Gly Lys Ser Ser
1               5

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 421

Leu Ala Val Val Gly Ala Cys Gly Val
1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 422
```

```
Gly Ile Arg Gly Val Gly Lys Ser Leu
1               5

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 423

Ala Tyr Asp Val Gly Lys Ser Ala Cys
1               5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 424

Leu Met Val Val Gly Ala Asp Gly Ala
1               5

<210> SEQ ID NO 425
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 425

Asp Pro Gly Lys Ser Ala Leu Thr Ile
1               5

<210> SEQ ID NO 426
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 426

Val Thr Gly Ala Gly Asp Val Gly Lys
1               5

<210> SEQ ID NO 427
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 427
```

Val Ala Gly Ala Cys Gly Val Gly Lys
1               5

<210> SEQ ID NO 428
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 428

Gly Ala Asp Gly Val Gly Lys Ser Cys
1               5

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 429

Gly Ile Cys Gly Val Gly Lys Ser Phe
1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 430

Val Val Gly Ala Val Gly Val Gly Phe
1               5

<210> SEQ ID NO 431
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 431

Val Ala Gly Ala Asp Gly Val Gly Leu
1               5

<210> SEQ ID NO 432
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

```
<400> SEQUENCE: 432

Val Ser Gly Ala Arg Gly Val Gly Tyr
1               5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 433

Leu Val Val Val Gly Ala Cys Gly Leu
1               5

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 434

Ala His Asp Val Gly Lys Ser Ala Leu
1               5

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 435

Gly Arg Asp Gly Val Gly Lys Ser Met
1               5

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 436

Val Thr Gly Ala Gly Asp Val Gly Tyr
1               5

<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)
```

```
<400> SEQUENCE: 437

Leu Thr Val Val Gly Ala Cys Gly Ile
1               5

<210> SEQ ID NO 438
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 438

Val Thr Gly Ala Arg Gly Val Gly Met
1               5

<210> SEQ ID NO 439
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 439

Ala Pro Asp Val Gly Lys Ser Ala Leu
1               5

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 440

Gly Val Cys Gly Val Gly Lys Ser Leu
1               5

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 441

Val Ala Gly Ala Gly Asp Val Gly Phe
1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Seed: GAVGVGKSA (KRAS G12V)

<400> SEQUENCE: 442

Gly Ile Val Gly Val Gly Lys Ser Leu
1               5

<210> SEQ ID NO 443
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 443

Val Ala Gly Ala Gly Asp Val Gly Leu
1               5

<210> SEQ ID NO 444
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 444

Ala Ile Asp Val Gly Lys Ser Ala Tyr
1               5

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 445

Gly Pro Val Gly Val Gly Lys Ser Cys
1               5

<210> SEQ ID NO 446
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 446

Gly His Asp Gly Val Gly Lys Ser Leu
1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: GAVGVGKSA (KRAS G12V)

<400> SEQUENCE: 447

Gly Pro Val Gly Val Gly Lys Ser Ser
1               5

<210> SEQ ID NO 448
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 448

Val Thr Gly Ala Arg Gly Val Gly Leu
1               5

<210> SEQ ID NO 449
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 449

Gly Gln Asp Gly Val Gly Lys Ser Phe
1               5

<210> SEQ ID NO 450
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 450

Val Leu Gly Ala Cys Gly Val Gly Arg
1               5

<210> SEQ ID NO 451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 451

Ala His Asp Val Gly Lys Ser Ala Met
1               5

<210> SEQ ID NO 452
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: Seed: LVVVGACGV (KRAS G12C)

<400> SEQUENCE: 452

Leu Gln Val Val Gly Ala Cys Gly Ile
1               5

<210> SEQ ID NO 453
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 453

Val Thr Gly Ala Arg Gly Val Gly Phe
1               5

<210> SEQ ID NO 454
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 454

Gly Ala Gly Asp Val Gly Lys Ser Ile
1               5

<210> SEQ ID NO 455
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 455

Val Ala Gly Ala Asp Gly Val Gly Met
1               5

<210> SEQ ID NO 456
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 456

Gly Gln Gly Asp Val Gly Lys Ser Tyr
1               5

<210> SEQ ID NO 457
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 457

Val Ala Gly Ala Arg Gly Val Gly Lys
1               5

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 458

Gly Leu Gly Asp Val Gly Lys Ser Tyr
1               5

<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 459

Val Leu Gly Ala Arg Gly Val Gly Arg
1               5

<210> SEQ ID NO 460
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 460

Gly Gly Val Gly Val Gly Lys Ser Met
1               5

<210> SEQ ID NO 461
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 461

Gly Gln Asp Gly Val Gly Lys Ser Val
1               5

<210> SEQ ID NO 462
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 462

Leu Gln Val Val Gly Ala Val Gly Ile
1               5

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 463

Leu Val Val Val Gly Ala Val Gly Ile
1               5

<210> SEQ ID NO 464
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 464

Val Thr Gly Ala Val Gly Val Gly Phe
1               5

<210> SEQ ID NO 465
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 465

Gly Gly Arg Gly Val Gly Lys Ser Phe
1               5

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 466

Gly Leu Arg Gly Val Gly Lys Ser Phe
1               5

<210> SEQ ID NO 467
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 467

Gly Met Gly Asp Val Gly Lys Ser Tyr
1               5

<210> SEQ ID NO 468
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 468

Gly Gln Asp Gly Val Gly Lys Ser Ile
1               5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 469

Val Ser Gly Ala Val Gly Val Gly Met
1               5

<210> SEQ ID NO 470
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 470

Gly Pro Val Gly Val Gly Lys Ser Phe
1               5

<210> SEQ ID NO 471
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 471

Asp Gln Gly Lys Ser Ala Leu Thr Val
1               5

<210> SEQ ID NO 472
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 472

Val Ser Gly Ala Arg Gly Val Gly Lys
1               5

<210> SEQ ID NO 473
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 473

Gly Pro Asp Gly Val Gly Lys Ser Leu
1               5

<210> SEQ ID NO 474
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 474

Val Ala Gly Ala Arg Gly Val Gly Arg
1               5

<210> SEQ ID NO 475
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 475

Gly Pro Asp Gly Val Gly Lys Ser Val
1               5

<210> SEQ ID NO 476
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 476

Gly Trp Asp Gly Val Gly Lys Ser Phe
1               5

<210> SEQ ID NO 477
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 477

Gly Val Val Gly Val Gly Lys Ser His
1               5

<210> SEQ ID NO 478
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 478

Val Ile Gly Ala Arg Gly Val Gly Lys
1               5

<210> SEQ ID NO 479
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 479

Asp Ser Gly Lys Ser Ala Leu Thr Val
1               5

<210> SEQ ID NO 480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 480

Asp Ala Gly Lys Ser Ala Leu Thr Phe
1               5

<210> SEQ ID NO 481
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 481

Gly Asn Asp Gly Val Gly Lys Ser Phe
1               5
```

```
<210> SEQ ID NO 482
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 482

Gly His Asp Gly Val Gly Lys Ser Met
1               5

<210> SEQ ID NO 483
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 483

Gly Ile Cys Gly Val Gly Lys Ser Met
1               5

<210> SEQ ID NO 484
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 484

Ala Asp Asp Val Gly Lys Ser Ala Ile
1               5

<210> SEQ ID NO 485
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 485

Gly Met Arg Gly Val Gly Lys Ser Phe
1               5

<210> SEQ ID NO 486
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 486

Gly Pro Arg Gly Val Gly Lys Ser Gly
1               5
```

```
<210> SEQ ID NO 487
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 487

Leu Ala Val Val Gly Ala Val Gly Val
1               5

<210> SEQ ID NO 488
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 488

Ala Arg Asp Val Gly Lys Ser Ala Ile
1               5

<210> SEQ ID NO 489
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 489

Leu Ile Val Val Gly Ala Cys Gly Leu
1               5

<210> SEQ ID NO 490
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 490

Leu Leu Val Val Gly Ala Val Gly Met
1               5

<210> SEQ ID NO 491
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 491

Gly Asn Asp Gly Val Gly Lys Ser Ile
1               5
```

<210> SEQ ID NO 492
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 492

Val Ser Gly Ala Cys Gly Val Gly Tyr
1               5

<210> SEQ ID NO 493
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 493

Asp Ala Gly Lys Ser Ala Leu Thr Trp
1               5

<210> SEQ ID NO 494
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 494

Val Ser Gly Ala Asp Gly Val Gly Tyr
1               5

<210> SEQ ID NO 495
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 495

Gly Thr Val Gly Val Gly Lys Ser His
1               5

<210> SEQ ID NO 496
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 496

Gly Val Arg Gly Val Gly Lys Ser Ala

<210> SEQ ID NO 497
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAGDV (KRAS G13D)

<400> SEQUENCE: 497

Leu Met Val Val Gly Ala Gly Asp Val
1               5

<210> SEQ ID NO 498
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 498

Val Val Gly Ala Cys Gly Val Gly Tyr
1               5

<210> SEQ ID NO 499
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 499

Asp Ile Gly Lys Ser Ala Leu Thr Tyr
1               5

<210> SEQ ID NO 500
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 500

Gly Ser Val Gly Val Gly Lys Ser Val
1               5

<210> SEQ ID NO 501
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 501

Gly Asn Asp Gly Val Gly Lys Ser Val
1               5

<210> SEQ ID NO 502
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 502

Gly Arg Asp Gly Val Gly Lys Ser Phe
1               5

<210> SEQ ID NO 503
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 503

Val Thr Gly Ala Arg Gly Val Gly Tyr
1               5

<210> SEQ ID NO 504
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 504

Gly Ile Gly Asp Val Gly Lys Ser Leu
1               5

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 505

Leu Ile Val Val Gly Ala Val Gly Ile
1               5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 506

```
Gly Ile Asp Gly Val Gly Lys Ser Tyr
1               5
```

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 507

```
Gly Thr Asp Gly Val Gly Lys Ser Cys
1               5
```

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 508

```
Gly Gln Cys Gly Val Gly Lys Ser Tyr
1               5
```

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 509

```
Val Gly Gly Ala Val Gly Val Gly Tyr
1               5
```

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 510

```
Ala His Asp Val Gly Lys Ser Ala Phe
1               5
```

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

```
<400> SEQUENCE: 511

Gly Met Val Gly Val Gly Lys Ser Phe
1               5

<210> SEQ ID NO 512
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 512

Gly Met Cys Gly Val Gly Lys Ser Tyr
1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 513

Ala Phe Asp Val Gly Lys Ser Ala Trp
1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 514

Leu Thr Val Val Gly Ala Val Gly Ile
1               5

<210> SEQ ID NO 515
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 515

Gly Leu Cys Gly Val Gly Lys Ser Tyr
1               5

<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)
```

<400> SEQUENCE: 516

Asp Gly Gly Lys Ser Ala Leu Thr Val
1               5

<210> SEQ ID NO 517
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 517

Gly Asn Arg Gly Val Gly Lys Ser Tyr
1               5

<210> SEQ ID NO 518
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 518

Val Ala Gly Ala Gly Asp Val Gly Arg
1               5

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 519

Ala Pro Asp Val Gly Lys Ser Ala Met
1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 520

Ala His Asp Val Gly Lys Ser Ala Tyr
1               5

<210> SEQ ID NO 521
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: VVGAGDVGK (KRAS G13D)

<400> SEQUENCE: 521

Val Ala Gly Ala Gly Asp Val Gly Met
1               5

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 522

Val Ile Gly Ala Cys Gly Val Gly Arg
1               5

<210> SEQ ID NO 523
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 523

Gly Arg Asp Gly Val Gly Lys Ser Ile
1               5

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 524

Val Ser Gly Ala Val Gly Val Gly Leu
1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 525

Leu Val Val Val Gly Ala Val Gly Leu
1               5

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: VVGARGVGK (KRAS G12R)

<400> SEQUENCE: 526

Val Ile Gly Ala Arg Gly Val Gly Arg
1               5

<210> SEQ ID NO 527
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 527

Gly Pro Gly Asp Val Gly Lys Ser Leu
1               5

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 528

Gly Ser Arg Gly Val Gly Lys Ser His
1               5

<210> SEQ ID NO 529
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 529

Ala Arg Asp Val Gly Lys Ser Ala Val
1               5

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 530

Gly Pro Gly Asp Val Gly Lys Ser Ile
1               5

<210> SEQ ID NO 531
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: Seed: GAGDVGKSA (KRAS G13D)

<400> SEQUENCE: 531

Gly Pro Gly Asp Val Gly Lys Ser Pro
1               5

<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 532

Ala Thr Asp Val Gly Lys Ser Ala Cys
1               5

<210> SEQ ID NO 533
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 533

Val Ser Gly Ala Gly Asp Val Gly Tyr
1               5

<210> SEQ ID NO 534
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 534

Val Val Gly Ala Asp Gly Val Gly Tyr
1               5

<210> SEQ ID NO 535
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 535

Gly Gln Val Gly Val Gly Lys Ser Phe
1               5

<210> SEQ ID NO 536
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 536

Val Ala Gly Ala Asp Gly Val Gly Lys
1               5

<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 537

Asp Val Gly Lys Ser Ala Leu Thr Val
1               5

<210> SEQ ID NO 538
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 538

Gly Asn Val Gly Val Gly Lys Ser Tyr
1               5

<210> SEQ ID NO 539
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 539

Gly Cys Val Gly Val Gly Lys Ser Tyr
1               5

<210> SEQ ID NO 540
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 540

Gly Leu Val Gly Val Gly Lys Ser Phe
1               5

<210> SEQ ID NO 541
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 541

Gly Gln Arg Gly Val Gly Lys Ser Phe
1               5

<210> SEQ ID NO 542
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 542

Ala Asp Asp Val Gly Lys Ser Ala Val
1               5

<210> SEQ ID NO 543
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 543

Leu Gln Val Val Gly Ala Asp Gly Leu
1               5

<210> SEQ ID NO 544
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 544

Gly Gly Gly Asp Val Gly Lys Ser Phe
1               5

<210> SEQ ID NO 545
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 545

Val Ala Gly Ala Arg Gly Val Gly Val
1               5

<210> SEQ ID NO 546
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 546

Gly Ser Arg Gly Val Gly Lys Ser Val
1               5

<210> SEQ ID NO 547
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 547

Gly Cys Arg Gly Val Gly Lys Ser Tyr
1               5

<210> SEQ ID NO 548
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 548

Gly Gly Arg Gly Val Gly Lys Ser Met
1               5

<210> SEQ ID NO 549
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 549

Val Pro Gly Ala Val Gly Val Gly Arg
1               5

<210> SEQ ID NO 550
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 550

Ala Ala Asp Val Gly Lys Ser Ala Trp
1               5

<210> SEQ ID NO 551
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 551

Ala Ser Asp Val Gly Lys Ser Ala Cys
1               5

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 552

Leu Ser Val Val Gly Ala Cys Gly Val
1               5

<210> SEQ ID NO 553
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 553

Gly Asp Asp Gly Val Gly Lys Ser Leu
1               5

<210> SEQ ID NO 554
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 554

Gly Ser Asp Gly Val Gly Lys Ser Cys
1               5

<210> SEQ ID NO 555
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 555

Gly Arg Asp Gly Val Gly Lys Ser Val
1               5

<210> SEQ ID NO 556
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 556

Val Ala Gly Ala Asp Gly Val Gly Arg
1               5

<210> SEQ ID NO 557
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 557

Val Met Gly Ala Asp Gly Val Gly Lys
1               5

<210> SEQ ID NO 558
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 558

Gly Gln Gly Asp Val Gly Lys Ser Phe
1               5

<210> SEQ ID NO 559
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 559

Ala Tyr Asp Val Gly Lys Ser Ala Trp
1               5

<210> SEQ ID NO 560
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 560

Leu Gln Val Val Gly Ala Arg Gly Val
1               5
```

```
<210> SEQ ID NO 561
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 561

Ala Ser Asp Val Gly Lys Ser Ala Ala
1               5

<210> SEQ ID NO 562
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 562

Ala Gly Asp Val Gly Lys Ser Ala Tyr
1               5

<210> SEQ ID NO 563
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 563

Val Thr Gly Ala Val Gly Val Gly Met
1               5

<210> SEQ ID NO 564
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 564

Val Val Gly Ala Val Gly Val Gly Met
1               5

<210> SEQ ID NO 565
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 565

Leu Leu Val Val Gly Ala Asp Gly Ala
1               5
```

```
<210> SEQ ID NO 566
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 566

Gly Ala Val Gly Val Gly Lys Ser Lys
1               5

<210> SEQ ID NO 567
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 567

Gly Val Gly Asp Val Gly Lys Ser His
1               5

<210> SEQ ID NO 568
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 568

Ala Glu Asp Val Gly Lys Ser Ala Tyr
1               5

<210> SEQ ID NO 569
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 569

Gly Pro Gly Asp Val Gly Lys Ser Thr
1               5

<210> SEQ ID NO 570
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 570

Gly Pro Val Gly Val Gly Lys Ser Gly
1               5
```

```
<210> SEQ ID NO 571
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 571

Gly Pro Asp Gly Val Gly Lys Ser Met
1               5

<210> SEQ ID NO 572
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 572

Leu Ile Val Val Gly Ala Val Gly Leu
1               5

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 573

Val Met Gly Ala Gly Asp Val Gly Lys
1               5

<210> SEQ ID NO 574
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 574

Gly Pro Cys Gly Val Gly Lys Ser Phe
1               5

<210> SEQ ID NO 575
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 575

Asp Val Gly Lys Ser Ala Leu Thr Leu
```

<210> SEQ ID NO 576
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 576

Val Thr Gly Ala Val Gly Val Gly Leu
1               5

<210> SEQ ID NO 577
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 577

Ala Trp Asp Val Gly Lys Ser Ala Cys
1               5

<210> SEQ ID NO 578
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 578

Ala Glu Asp Val Gly Lys Ser Ala Trp
1               5

<210> SEQ ID NO 579
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 579

Asp Gln Gly Lys Ser Ala Leu Thr Ile
1               5

<210> SEQ ID NO 580
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 580

Val Tyr Gly Ala Val Gly Val Gly Arg
1               5

<210> SEQ ID NO 581
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 581

Gly Ser Asp Gly Val Gly Lys Ser Ala
1               5

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 582

Val Gly Gly Ala Val Gly Val Gly Lys
1               5

<210> SEQ ID NO 583
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 583

Gly Leu Gly Asp Val Gly Lys Ser Phe
1               5

<210> SEQ ID NO 584
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 584

Gly Ser Val Gly Val Gly Lys Ser Ile
1               5

<210> SEQ ID NO 585
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 585

```
Leu Met Val Val Gly Ala Cys Gly Met
1               5

<210> SEQ ID NO 586
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 586

Gly Ala Val Gly Val Gly Lys Ser Trp
1               5

<210> SEQ ID NO 587
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 587

Gly Met Gly Asp Val Gly Lys Ser Phe
1               5

<210> SEQ ID NO 588
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 588

Ala Trp Asp Val Gly Lys Ser Ala Tyr
1               5

<210> SEQ ID NO 589
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 589

Gly Ala Asp Gly Val Gly Lys Ser Trp
1               5

<210> SEQ ID NO 590
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)
```

```
<400> SEQUENCE: 590

Val Ala Gly Ala Gly Asp Val Gly Lys
1               5

<210> SEQ ID NO 591
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 591

Leu Ser Val Val Gly Ala Val Gly Val
1               5

<210> SEQ ID NO 592
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 592

Val Ile Gly Ala Val Gly Val Gly Phe
1               5

<210> SEQ ID NO 593
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 593

Val Ala Gly Ala Arg Gly Val Gly Ile
1               5

<210> SEQ ID NO 594
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 594

Gly Leu Arg Gly Val Gly Lys Ser Met
1               5

<210> SEQ ID NO 595
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)
```

```
<400> SEQUENCE: 595

Gly Ile Val Gly Val Gly Lys Ser His
1               5

<210> SEQ ID NO 596
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 596

Gly Met Val Gly Val Gly Lys Ser Met
1               5

<210> SEQ ID NO 597
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 597

Gly Ser Arg Gly Val Gly Lys Ser Ile
1               5

<210> SEQ ID NO 598
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 598

Ala Ala Asp Val Gly Lys Ser Ala Thr
1               5

<210> SEQ ID NO 599
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 599

Gly Gly Cys Gly Val Gly Lys Ser Phe
1               5

<210> SEQ ID NO 600
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Seed: GADGVGKSA (KRAS G12D)

<400> SEQUENCE: 600

Gly Gly Asp Gly Val Gly Lys Ser Tyr
1               5

<210> SEQ ID NO 601
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 601

Gly Ala Val Gly Val Gly Lys Ser Arg
1               5

<210> SEQ ID NO 602
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 602

Gly Trp Asp Gly Val Gly Lys Ser Ile
1               5

<210> SEQ ID NO 603
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 603

Asp Ser Gly Lys Ser Ala Leu Thr Ile
1               5

<210> SEQ ID NO 604
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 604

Ala Met Asp Val Gly Lys Ser Ala Tyr
1               5

<210> SEQ ID NO 605
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: GACGVGKSA (KRAS G12C)

<400> SEQUENCE: 605

Gly Ile Cys Gly Val Gly Lys Ser Leu
1               5

<210> SEQ ID NO 606
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 606

Gly Ser Gly Asp Val Gly Lys Ser His
1               5

<210> SEQ ID NO 607
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 607

Val Ser Gly Ala Arg Gly Val Gly Arg
1               5

<210> SEQ ID NO 608
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 608

Leu Val Val Val Gly Ala Asp Gly Leu
1               5

<210> SEQ ID NO 609
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 609

Gly His Asp Gly Val Gly Lys Ser Phe
1               5

<210> SEQ ID NO 610
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: Seed: DVGKSALTI (KRAS G13D)

<400> SEQUENCE: 610

Asp Ala Gly Lys Ser Ala Leu Thr Met
1               5

<210> SEQ ID NO 611
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 611

Ala Gln Asp Val Gly Lys Ser Ala Tyr
1               5

<210> SEQ ID NO 612
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 612

Val Ser Gly Ala Cys Gly Val Gly Phe
1               5

<210> SEQ ID NO 613
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 613

Gly Pro Gly Asp Val Gly Lys Ser Met
1               5

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAGDV (KRAS G13D)

<400> SEQUENCE: 614

Leu Leu Val Val Gly Ala Gly Asp Val
1               5

<210> SEQ ID NO 615
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 615

Ala Ala Asp Val Gly Lys Ser Ala His
1               5

<210> SEQ ID NO 616
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 616

Val Gly Gly Ala Val Gly Val Gly Arg
1               5

<210> SEQ ID NO 617
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 617

Gly Trp Asp Gly Val Gly Lys Ser Val
1               5

<210> SEQ ID NO 618
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 618

Gly Met Arg Gly Val Gly Lys Ser Met
1               5

<210> SEQ ID NO 619
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 619

Val Ser Gly Ala Gly Asp Val Gly Arg
1               5

<210> SEQ ID NO 620
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 620

Gly Gln Val Gly Val Gly Lys Ser Met
1               5

<210> SEQ ID NO 621
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 621

Val Met Gly Ala Asp Gly Val Gly Arg
1               5

<210> SEQ ID NO 622
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 622

Gly Val Val Gly Val Gly Lys Ser Lys
1               5

<210> SEQ ID NO 623
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 623

Val Ile Gly Ala Asp Gly Val Gly Lys
1               5

<210> SEQ ID NO 624
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 624

Gly Gly Val Gly Val Gly Lys Ser Leu
1               5

<210> SEQ ID NO 625
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 625

Gly Asn Gly Asp Val Gly Lys Ser Tyr
1               5

<210> SEQ ID NO 626
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 626

Gly Ala Asp Gly Val Gly Lys Ser Thr
1               5

<210> SEQ ID NO 627
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 627

Ala Phe Asp Val Gly Lys Ser Ala Ala
1               5

<210> SEQ ID NO 628
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 628

Asp Ala Gly Lys Ser Ala Leu Thr Tyr
1               5

<210> SEQ ID NO 629
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 629

Gly Asn Cys Gly Val Gly Lys Ser Tyr
1               5

<210> SEQ ID NO 630
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 630

Val Ser Gly Ala Asp Gly Val Gly Lys
1               5

<210> SEQ ID NO 631
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 631

Val Met Gly Ala Gly Asp Val Gly Arg
1               5

<210> SEQ ID NO 632
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 632

Ala Lys Asp Val Gly Lys Ser Ala Leu
1               5

<210> SEQ ID NO 633
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 633

Ala Ile Asp Val Gly Lys Ser Ala Cys
1               5

<210> SEQ ID NO 634
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 634

Gly Ser Cys Gly Val Gly Lys Ser His
1               5

<210> SEQ ID NO 635
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 635

Gly Ala Gly Asp Val Gly Lys Ser Lys
1               5

<210> SEQ ID NO 636
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 636

Ala Tyr Asp Val Gly Lys Ser Ala Ala
1               5

<210> SEQ ID NO 637
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 637

Gly Pro Cys Gly Val Gly Lys Ser Cys
1               5

<210> SEQ ID NO 638
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 638

Val Gln Gly Ala Val Gly Val Gly Arg
1               5

<210> SEQ ID NO 639
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 639

Leu Leu Val Val Gly Ala Arg Gly Ala
1               5
```

```
<210> SEQ ID NO 640
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 640

Gly Gln Asp Gly Val Gly Lys Ser Tyr
1               5

<210> SEQ ID NO 641
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 641

Val Val Gly Ala Gly Asp Val Gly Tyr
1               5

<210> SEQ ID NO 642
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 642

Val Ile Gly Ala Asp Gly Val Gly Arg
1               5

<210> SEQ ID NO 643
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 643

Gly Thr Asp Gly Val Gly Lys Ser Ala
1               5

<210> SEQ ID NO 644
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 644

Val Gln Gly Ala Val Gly Val Gly Lys
1               5
```

<210> SEQ ID NO 645
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 645

Gly Val Gly Asp Val Gly Lys Ser Lys
1               5

<210> SEQ ID NO 646
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 646

Gly Val Asp Gly Val Gly Lys Ser Cys
1               5

<210> SEQ ID NO 647
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 647

Leu Leu Val Val Gly Ala Cys Gly Met
1               5

<210> SEQ ID NO 648
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 648

Asp Ser Gly Lys Ser Ala Leu Thr Phe
1               5

<210> SEQ ID NO 649
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 649

Asp Pro Gly Lys Ser Ala Leu Thr Leu
1               5

```
<210> SEQ ID NO 650
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 650

Gly Ile Asp Gly Val Gly Lys Ser Cys
1               5

<210> SEQ ID NO 651
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 651

Gly Ile Val Gly Val Gly Lys Ser Lys
1               5

<210> SEQ ID NO 652
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 652

Gly Val Arg Gly Val Gly Lys Ser His
1               5

<210> SEQ ID NO 653
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 653

Gly Met Asp Gly Val Gly Lys Ser Tyr
1               5

<210> SEQ ID NO 654
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 654

Gly Ala Gly Asp Val Gly Lys Ser Arg
```

```
1               5

<210> SEQ ID NO 655
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 655

Val Ile Gly Ala Gly Asp Val Gly Lys
1               5

<210> SEQ ID NO 656
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 656

Gly Glu Arg Gly Val Gly Lys Ser Tyr
1               5

<210> SEQ ID NO 657
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 657

Gly Val Gly Asp Val Gly Lys Ser Arg
1               5

<210> SEQ ID NO 658
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 658

Gly Ser Val Gly Val Gly Lys Ser Lys
1               5

<210> SEQ ID NO 659
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 659
```

-continued

Leu Val Val Val Gly Ala Asp Gly Ile
1               5

<210> SEQ ID NO 660
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 660

Leu Ile Val Val Gly Ala Arg Gly Val
1               5

<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 661

Gly Thr Val Gly Val Gly Lys Ser Val
1               5

<210> SEQ ID NO 662
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 662

Gly Pro Cys Gly Val Gly Lys Ser Ser
1               5

<210> SEQ ID NO 663
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 663

Gly Val Val Gly Val Gly Lys Ser Arg
1               5

<210> SEQ ID NO 664
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 664

```
Ala Pro Asp Val Gly Lys Ser Ala Val
1               5

<210> SEQ ID NO 665
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 665

Gly Val Asp Gly Val Gly Lys Ser Arg
1               5

<210> SEQ ID NO 666
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 666

Gly Asp Asp Gly Val Gly Lys Ser Met
1               5

<210> SEQ ID NO 667
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 667

Gly Gly Gly Asp Val Gly Lys Ser Met
1               5

<210> SEQ ID NO 668
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 668

Ala Leu Asp Val Gly Lys Ser Ala Tyr
1               5

<210> SEQ ID NO 669
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)
```

```
-continued

<400> SEQUENCE: 669

Val Ser Gly Ala Asp Gly Val Gly Arg
1               5

<210> SEQ ID NO 670
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 670

Val Arg Gly Ala Val Gly Val Gly Leu
1               5

<210> SEQ ID NO 671
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 671

Gly Ala Asp Gly Val Gly Lys Ser His
1               5

<210> SEQ ID NO 672
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 672

Gly Thr Val Gly Val Gly Lys Ser Ile
1               5

<210> SEQ ID NO 673
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 673

Val Ile Gly Ala Cys Gly Val Gly Tyr
1               5

<210> SEQ ID NO 674
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)
```

<400> SEQUENCE: 674

Val Ala Gly Ala Val Gly Val Gly Ile
1               5

<210> SEQ ID NO 675
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 675

Gly Val Arg Gly Val Gly Lys Ser Val
1               5

<210> SEQ ID NO 676
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 676

Ala Val Asp Val Gly Lys Ser Ala Cys
1               5

<210> SEQ ID NO 677
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 677

Gly Met Cys Gly Val Gly Lys Ser Phe
1               5

<210> SEQ ID NO 678
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 678

Gly Ala Asp Gly Val Gly Lys Ser Lys
1               5

<210> SEQ ID NO 679
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: AGDVGKSAL (KRAS G13D)

<400> SEQUENCE: 679

Ala Pro Asp Val Gly Lys Ser Ala Ile
1               5

<210> SEQ ID NO 680
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 680

Gly Gln Arg Gly Val Gly Lys Ser Met
1               5

<210> SEQ ID NO 681
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 681

Gly Val Asp Gly Val Gly Lys Ser Lys
1               5

<210> SEQ ID NO 682
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 682

Gly Lys Asp Gly Val Gly Lys Ser Leu
1               5

<210> SEQ ID NO 683
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 683

Gly Leu Val Gly Val Gly Lys Ser Met
1               5

<210> SEQ ID NO 684
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: Seed: GADGVGKSA (KRAS G12D)

<400> SEQUENCE: 684

Gly Ala Asp Gly Val Gly Lys Ser Arg
1               5

<210> SEQ ID NO 685
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 685

Val Ile Gly Ala Gly Asp Val Gly Arg
1               5

<210> SEQ ID NO 686
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 686

Val Val Gly Ala Cys Gly Val Gly Phe
1               5

<210> SEQ ID NO 687
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 687

Gly Val Arg Gly Val Gly Lys Ser Ile
1               5

<210> SEQ ID NO 688
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 688

Gly Ile Val Gly Val Gly Lys Ser Arg
1               5

<210> SEQ ID NO 689
<211> LENGTH: 9
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<223> OTHER INFORMATION: Seed: GAGDVGKSA (KRAS G13D)

<400> SEQUENCE: 689

Gly Ile Gly Asp Val Gly Lys Ser Arg
1               5

<210> SEQ ID NO 690
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 690

Val Ala Gly Ala Val Gly Val Gly Val
1               5

<210> SEQ ID NO 691
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 691

Gly Thr Val Gly Val Gly Lys Ser Lys
1               5

<210> SEQ ID NO 692
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 692

Val Met Gly Ala Val Gly Val Gly Tyr
1               5

<210> SEQ ID NO 693
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 693

Gly Ile Gly Asp Val Gly Lys Ser Lys
1               5

<210> SEQ ID NO 694
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 694

Leu Ile Val Val Gly Ala Asp Gly Leu
1               5

<210> SEQ ID NO 695
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 695

Gly Ala Arg Gly Val Gly Lys Ser Trp
1               5

<210> SEQ ID NO 696
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 696

Leu Thr Val Val Gly Ala Cys Gly Leu
1               5

<210> SEQ ID NO 697
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 697

Gly Gln Gly Asp Val Gly Lys Ser Met
1               5

<210> SEQ ID NO 698
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 698

Ala Thr Asp Val Gly Lys Ser Ala Ala
1               5

<210> SEQ ID NO 699
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 699

Gly Gln Cys Gly Val Gly Lys Ser Phe
1               5

<210> SEQ ID NO 700
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 700

Val Ser Gly Ala Asp Gly Val Gly Phe
1               5

<210> SEQ ID NO 701
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 701

Gly Pro Asp Gly Val Gly Lys Ser Ile
1               5

<210> SEQ ID NO 702
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 702

Gly Ser Val Gly Val Gly Lys Ser Arg
1               5

<210> SEQ ID NO 703
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 703

Val Leu Gly Ala Gly Asp Val Gly Arg
1               5

<210> SEQ ID NO 704
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 704

Gly Ile Asp Gly Val Gly Lys Ser Arg
1               5

<210> SEQ ID NO 705
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 705

Asp Gly Gly Lys Ser Ala Leu Thr Ile
1               5

<210> SEQ ID NO 706
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 706

Gly Thr Arg Gly Val Gly Lys Ser His
1               5

<210> SEQ ID NO 707
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 707

Gly Ala Gly Asp Val Gly Lys Ser Trp
1               5

<210> SEQ ID NO 708
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 708

Asp Ser Gly Lys Ser Ala Leu Thr Trp
1               5

<210> SEQ ID NO 709
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 709

Val Ser Gly Ala Gly Asp Val Gly Lys
1               5

<210> SEQ ID NO 710
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 710

Gly Gly Cys Gly Val Gly Lys Ser Met
1               5

<210> SEQ ID NO 711
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 711

Gly Met Arg Gly Val Gly Lys Ser Leu
1               5

<210> SEQ ID NO 712
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 712

Gly Thr Val Gly Val Gly Lys Ser Arg
1               5

<210> SEQ ID NO 713
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 713

Gly Met Gly Asp Val Gly Lys Ser Met
1               5

<210> SEQ ID NO 714
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 714

Val Leu Gly Ala Asp Gly Val Gly Lys
1               5

<210> SEQ ID NO 715
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 715

Gly Glu Val Gly Val Gly Lys Ser Tyr
1               5

<210> SEQ ID NO 716
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 716

Val Ala Gly Ala Cys Gly Val Gly His
1               5

<210> SEQ ID NO 717
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 717

Leu Gln Val Val Gly Ala Asp Gly Ile
1               5

<210> SEQ ID NO 718
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 718

Val Phe Gly Ala Val Gly Val Gly Arg
1               5
```

```
<210> SEQ ID NO 719
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 719

Asp Gln Gly Lys Ser Ala Leu Thr Leu
1               5

<210> SEQ ID NO 720
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 720

Gly Gly Val Gly Val Gly Lys Ser Lys
1               5

<210> SEQ ID NO 721
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 721

Gly Leu Cys Gly Val Gly Lys Ser Phe
1               5

<210> SEQ ID NO 722
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 722

Val Leu Gly Ala Asp Gly Val Gly Arg
1               5

<210> SEQ ID NO 723
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 723

Gly Leu Gly Asp Val Gly Lys Ser Met
1               5
```

```
<210> SEQ ID NO 724
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 724

Val Gly Gly Ala Asp Gly Val Gly Lys
1               5

<210> SEQ ID NO 725
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 725

Leu Thr Val Val Gly Ala Arg Gly Val
1               5

<210> SEQ ID NO 726
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 726

Ala Leu Asp Val Gly Lys Ser Ala Cys
1               5

<210> SEQ ID NO 727
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 727

Gly Val Cys Gly Val Gly Lys Ser His
1               5

<210> SEQ ID NO 728
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 728

Val Leu Gly Ala Gly Asp Val Gly Lys
1               5
```

<210> SEQ ID NO 729
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 729

Leu Thr Val Val Gly Ala Val Gly Leu
1               5

<210> SEQ ID NO 730
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 730

Leu Ile Val Val Gly Ala Asp Gly Ile
1               5

<210> SEQ ID NO 731
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 731

Val Gly Gly Ala Asp Gly Val Gly Arg
1               5

<210> SEQ ID NO 732
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 732

Val Ala Gly Ala Asp Gly Val Gly His
1               5

<210> SEQ ID NO 733
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 733

Asp Leu Gly Lys Ser Ala Leu Thr Trp

```
1               5

<210> SEQ ID NO 734
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 734

Gly Glu Asp Gly Val Gly Lys Ser Leu
1               5

<210> SEQ ID NO 735
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 735

Gly Gly Val Gly Val Gly Lys Ser Arg
1               5

<210> SEQ ID NO 736
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 736

Gly Leu Asp Gly Val Gly Lys Ser Tyr
1               5

<210> SEQ ID NO 737
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 737

Gly Ile Asp Gly Val Gly Lys Ser Lys
1               5

<210> SEQ ID NO 738
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 738
```

```
Gly Thr Gly Asp Val Gly Lys Ser His
1               5

<210> SEQ ID NO 739
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 739

Val Val Gly Ala Asp Gly Val Gly Phe
1               5

<210> SEQ ID NO 740
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 740

Leu Thr Val Val Gly Ala Cys Gly Ala
1               5

<210> SEQ ID NO 741
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 741

Val Ile Gly Ala Asp Gly Val Gly Tyr
1               5

<210> SEQ ID NO 742
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 742

Gly Tyr Asp Gly Val Gly Lys Ser Cys
1               5

<210> SEQ ID NO 743
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 743
```

```
Asp Val Gly Lys Ser Ala Leu Thr Met
1               5

<210> SEQ ID NO 744
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 744

Ala His Asp Val Gly Lys Ser Ala Ile
1               5

<210> SEQ ID NO 745
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 745

Gly Ser Gly Asp Val Gly Lys Ser Lys
1               5

<210> SEQ ID NO 746
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 746

Gly Ile Gly Asp Val Gly Lys Ser His
1               5

<210> SEQ ID NO 747
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 747

Gly Thr Gly Asp Val Gly Lys Ser Lys
1               5

<210> SEQ ID NO 748
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)
```

<400> SEQUENCE: 748

Gly Thr Gly Asp Val Gly Lys Ser Arg
1               5

<210> SEQ ID NO 749
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 749

Gly Thr Asp Gly Val Gly Lys Ser Arg
1               5

<210> SEQ ID NO 750
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 750

Gly Ser Cys Gly Val Gly Lys Ser Val
1               5

<210> SEQ ID NO 751
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 751

Gly Gly Arg Gly Val Gly Lys Ser Leu
1               5

<210> SEQ ID NO 752
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 752

Val Gly Gly Ala Gly Asp Val Gly Lys
1               5

<210> SEQ ID NO 753
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

```
<400> SEQUENCE: 753

Gly Val Val Gly Val Gly Lys Ser Val
1               5

<210> SEQ ID NO 754
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 754

Gly Ser Gly Asp Val Gly Lys Ser Arg
1               5

<210> SEQ ID NO 755
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 755

Val Pro Gly Ala Val Gly Val Gly Lys
1               5

<210> SEQ ID NO 756
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 756

Leu Ile Val Val Gly Ala Cys Gly Ala
1               5

<210> SEQ ID NO 757
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 757

Gly Cys Gly Asp Val Gly Lys Ser Tyr
1               5

<210> SEQ ID NO 758
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Seed: AGDVGKSAL (KRAS G13D)

<400> SEQUENCE: 758

Ala Trp Asp Val Gly Lys Ser Ala Trp
1               5

<210> SEQ ID NO 759
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 759

Gly Thr Asp Gly Val Gly Lys Ser Lys
1               5

<210> SEQ ID NO 760
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 760

Val Pro Gly Ala Cys Gly Val Gly Arg
1               5

<210> SEQ ID NO 761
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 761

Gly Thr Arg Gly Val Gly Lys Ser Val
1               5

<210> SEQ ID NO 762
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 762

Ala Ile Asp Val Gly Lys Ser Ala Trp
1               5

<210> SEQ ID NO 763
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: GAVGVGKSA (KRAS G12V)

<400> SEQUENCE: 763

Gly Pro Val Gly Val Gly Lys Ser Tyr
1               5

<210> SEQ ID NO 764
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 764

Val Val Gly Ala Val Gly Val Gly Leu
1               5

<210> SEQ ID NO 765
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 765

Gly Val Cys Gly Val Gly Lys Ser Lys
1               5

<210> SEQ ID NO 766
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 766

Gly Glu Gly Asp Val Gly Lys Ser Tyr
1               5

<210> SEQ ID NO 767
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 767

Val Gln Gly Ala Val Gly Val Gly Tyr
1               5

<210> SEQ ID NO 768
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: Seed: VVGAVGVGK (KRAS G12V)

<400> SEQUENCE: 768

Val Asn Gly Ala Val Gly Val Gly Lys
1               5

<210> SEQ ID NO 769
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 769

Gly Ala Cys Gly Val Gly Lys Ser Trp
1               5

<210> SEQ ID NO 770
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 770

Gly Gly Asp Gly Val Gly Lys Ser Arg
1               5

<210> SEQ ID NO 771
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 771

Gly Pro Arg Gly Val Gly Lys Ser Tyr
1               5

<210> SEQ ID NO 772
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 772

Gly Ala Cys Gly Val Gly Lys Ser Lys
1               5

<210> SEQ ID NO 773
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 773

Val Ser Gly Ala Gly Asp Val Gly Phe
1               5

<210> SEQ ID NO 774
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 774

Gly His Asp Gly Val Gly Lys Ser Ile
1               5

<210> SEQ ID NO 775
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 775

Val Tyr Gly Ala Cys Gly Val Gly Arg
1               5

<210> SEQ ID NO 776
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 776

Ala Met Asp Val Gly Lys Ser Ala Cys
1               5

<210> SEQ ID NO 777
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 777

Gly Met Cys Gly Val Gly Lys Ser Met
1               5

<210> SEQ ID NO 778
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 778

Gly Ser Asp Gly Val Gly Lys Ser Arg
1               5

<210> SEQ ID NO 779
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 779

Gly Pro Arg Gly Val Gly Lys Ser Trp
1               5

<210> SEQ ID NO 780
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 780

Gly Gly Val Gly Val Gly Lys Ser His
1               5

<210> SEQ ID NO 781
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 781

Val Leu Gly Ala Val Gly Val Gly Tyr
1               5

<210> SEQ ID NO 782
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 782

Gly Gln Cys Gly Val Gly Lys Ser Met
1               5

<210> SEQ ID NO 783
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 783

Gly Val Val Gly Val Gly Lys Ser Ile
1               5

<210> SEQ ID NO 784
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 784

Gly Val Gly Asp Val Gly Lys Ser Val
1               5

<210> SEQ ID NO 785
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 785

Gly Pro Asp Gly Val Gly Lys Ser Thr
1               5

<210> SEQ ID NO 786
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 786

Ala Lys Asp Val Gly Lys Ser Ala Met
1               5

<210> SEQ ID NO 787
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 787

Ala Pro Asp Val Gly Lys Ser Ala Phe
1               5

<210> SEQ ID NO 788
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 788

Val Asn Gly Ala Val Gly Val Gly Arg
1               5

<210> SEQ ID NO 789
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 789

Val Gly Gly Ala Gly Asp Val Gly Arg
1               5

<210> SEQ ID NO 790
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 790

Leu Val Val Val Gly Ala Cys Gly Ala
1               5

<210> SEQ ID NO 791
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 791

Ala Glu Asp Val Gly Lys Ser Ala Cys
1               5

<210> SEQ ID NO 792
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 792

Gly Pro Gly Asp Val Gly Lys Ser Cys
1               5

<210> SEQ ID NO 793
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 793

Ala His Asp Val Gly Lys Ser Ala Val
1               5

<210> SEQ ID NO 794
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 794

Asp Met Gly Lys Ser Ala Leu Thr Trp
1               5

<210> SEQ ID NO 795
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 795

Gly Leu Arg Gly Val Gly Lys Ser Leu
1               5

<210> SEQ ID NO 796
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 796

Val Ser Gly Ala Val Gly Val Gly His
1               5

<210> SEQ ID NO 797
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 797

Gly Asp Asp Gly Val Gly Lys Ser Phe
1               5
```

```
<210> SEQ ID NO 798
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 798

Gly Gly Asp Gly Val Gly Lys Ser Lys
1               5

<210> SEQ ID NO 799
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 799

Gly Met Val Gly Val Gly Lys Ser Leu
1               5

<210> SEQ ID NO 800
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 800

Val Gly Gly Ala Cys Gly Val Gly Lys
1               5

<210> SEQ ID NO 801
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 801

Gly Ser Asp Gly Val Gly Lys Ser Trp
1               5

<210> SEQ ID NO 802
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 802

Gly Cys Val Gly Val Gly Lys Ser Phe
1               5
```

<210> SEQ ID NO 803
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 803

Gly Ser Gly Asp Val Gly Lys Ser Val
1               5

<210> SEQ ID NO 804
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 804

Gly Thr Cys Gly Val Gly Lys Ser His
1               5

<210> SEQ ID NO 805
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 805

Val Phe Gly Ala Cys Gly Val Gly Arg
1               5

<210> SEQ ID NO 806
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 806

Val Gln Gly Ala Cys Gly Val Gly Lys
1               5

<210> SEQ ID NO 807
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 807

Gly Ser Val Gly Val Gly Lys Ser Ala
1               5

```
<210> SEQ ID NO 808
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 808

Gly Leu Asp Gly Val Gly Lys Ser Arg
1               5

<210> SEQ ID NO 809
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 809

Leu Ala Val Val Gly Ala Asp Gly Val
1               5

<210> SEQ ID NO 810
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 810

Gly Glu Cys Gly Val Gly Lys Ser Tyr
1               5

<210> SEQ ID NO 811
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 811

Gly Ser Asp Gly Val Gly Lys Ser Lys
1               5

<210> SEQ ID NO 812
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 812

Gly Gly Gly Asp Val Gly Lys Ser Arg
```

```
<210> SEQ ID NO 813
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 813

Gly Pro Cys Gly Val Gly Lys Ser Gly
1               5

<210> SEQ ID NO 814
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 814

Ala Ile Asp Val Gly Lys Ser Ala Ala
1               5

<210> SEQ ID NO 815
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 815

Gly Ala Cys Gly Val Gly Lys Ser Arg
1               5

<210> SEQ ID NO 816
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 816

Val Asp Gly Ala Val Gly Val Gly Lys
1               5

<210> SEQ ID NO 817
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 817
```

```
Gly Leu Cys Gly Val Gly Lys Ser Met
1               5
```

<210> SEQ ID NO 818
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 818

```
Gly Ser Cys Gly Val Gly Lys Ser Ile
1               5
```

<210> SEQ ID NO 819
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 819

```
Gly Ile Arg Gly Val Gly Lys Ser His
1               5
```

<210> SEQ ID NO 820
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 820

```
Gly Leu Asp Gly Val Gly Lys Ser Cys
1               5
```

<210> SEQ ID NO 821
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 821

```
Gly Asn Val Gly Val Gly Lys Ser Phe
1               5
```

<210> SEQ ID NO 822
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 822

```
Gly His Asp Gly Val Gly Lys Ser Val
1               5

<210> SEQ ID NO 823
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 823

Gly Ile Cys Gly Val Gly Lys Ser Lys
1               5

<210> SEQ ID NO 824
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 824

Gly Thr Arg Gly Val Gly Lys Ser Ile
1               5

<210> SEQ ID NO 825
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 825

Gly Cys Cys Gly Val Gly Lys Ser Tyr
1               5

<210> SEQ ID NO 826
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 826

Gly Leu Val Gly Val Gly Lys Ser Lys
1               5

<210> SEQ ID NO 827
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)
```

<400> SEQUENCE: 827

Val Tyr Gly Ala Arg Gly Val Gly Arg
1               5

<210> SEQ ID NO 828
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 828

Asp Ser Gly Lys Ser Ala Leu Thr Tyr
1               5

<210> SEQ ID NO 829
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 829

Val Gly Gly Ala Cys Gly Val Gly Tyr
1               5

<210> SEQ ID NO 830
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 830

Gly Asn Arg Gly Val Gly Lys Ser Phe
1               5

<210> SEQ ID NO 831
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 831

Val Thr Gly Ala Asp Gly Val Gly Phe
1               5

<210> SEQ ID NO 832
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

```
<400> SEQUENCE: 832

Gly Val Cys Gly Val Gly Lys Ser Val
1               5

<210> SEQ ID NO 833
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 833

Gly Gly Gly Asp Val Gly Lys Ser Lys
1               5

<210> SEQ ID NO 834
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 834

Gly Ile Asp Gly Val Gly Lys Ser Trp
1               5

<210> SEQ ID NO 835
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 835

Gly Val Asp Gly Val Gly Lys Ser Ala
1               5

<210> SEQ ID NO 836
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 836

Ala Val Asp Val Gly Lys Ser Ala Ala
1               5

<210> SEQ ID NO 837
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Seed: AGDVGKSAL (KRAS G13D)

<400> SEQUENCE: 837

Ala Ser Asp Val Gly Lys Ser Ala Trp
1               5

<210> SEQ ID NO 838
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 838

Val Ser Gly Ala Cys Gly Val Gly Met
1               5

<210> SEQ ID NO 839
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 839

Gly Leu Asp Gly Val Gly Lys Ser Lys
1               5

<210> SEQ ID NO 840
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 840

Gly Val Cys Gly Val Gly Lys Ser Arg
1               5

<210> SEQ ID NO 841
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 841

Gly Glu Asp Gly Val Gly Lys Ser Met
1               5

<210> SEQ ID NO 842
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: Seed: GAGDVGKSA (KRAS G13D)

<400> SEQUENCE: 842

Gly Thr Gly Asp Val Gly Lys Ser Val
1               5

<210> SEQ ID NO 843
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 843

Val Thr Gly Ala Cys Gly Val Gly Phe
1               5

<210> SEQ ID NO 844
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 844

Gly Ile Arg Gly Val Gly Lys Ser Ala
1               5

<210> SEQ ID NO 845
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 845

Gly Leu Gly Asp Val Gly Lys Ser Arg
1               5

<210> SEQ ID NO 846
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 846

Val Val Gly Ala Gly Asp Val Gly Phe
1               5

<210> SEQ ID NO 847
<211> LENGTH: 9
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<223> OTHER INFORMATION: Seed: GAVGVGKSA (KRAS G12V)

<400> SEQUENCE: 847

Gly Asn Val Gly Val Gly Lys Ser Lys
1               5

<210> SEQ ID NO 848
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 848

Gly Pro Asp Gly Val Gly Lys Ser Pro
1               5

<210> SEQ ID NO 849
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 849

Leu Met Val Val Gly Ala Asp Gly Met
1               5

<210> SEQ ID NO 850
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 850

Val Gln Gly Ala Cys Gly Val Gly Arg
1               5

<210> SEQ ID NO 851
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 851

Val Glu Gly Ala Val Gly Val Gly Lys
1               5

<210> SEQ ID NO 852
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 852

Gly Ile Cys Gly Val Gly Lys Ser Arg
1               5

<210> SEQ ID NO 853
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 853

Ala Val Asp Val Gly Lys Ser Ala Trp
1               5

<210> SEQ ID NO 854
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 854

Gly Cys Arg Gly Val Gly Lys Ser Phe
1               5

<210> SEQ ID NO 855
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 855

Val Phe Gly Ala Arg Gly Val Gly Arg
1               5

<210> SEQ ID NO 856
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 856

Asp Ala Gly Lys Ser Ala Leu Thr Cys
1               5

<210> SEQ ID NO 857
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 857

Asp Thr Gly Lys Ser Ala Leu Thr Val
1               5

<210> SEQ ID NO 858
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 858

Ala Glu Asp Val Gly Lys Ser Ala Ala
1               5

<210> SEQ ID NO 859
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 859

Gly Tyr Asp Gly Val Gly Lys Ser Tyr
1               5

<210> SEQ ID NO 860
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 860

Val Gly Gly Ala Val Gly Val Gly Phe
1               5

<210> SEQ ID NO 861
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 861

Val Val Gly Ala Arg Gly Val Gly Tyr
1               5

<210> SEQ ID NO 862
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 862

Ala Leu Asp Val Gly Lys Ser Ala Trp
1               5

<210> SEQ ID NO 863
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 863

Ala Val Asp Val Gly Lys Ser Ala Lys
1               5

<210> SEQ ID NO 864
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 864

Gly Ile Asp Gly Val Gly Lys Ser Ala
1               5

<210> SEQ ID NO 865
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 865

Val Gly Gly Ala Cys Gly Val Gly Arg
1               5

<210> SEQ ID NO 866
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 866

Gly Leu Gly Asp Val Gly Lys Ser Lys
1               5

<210> SEQ ID NO 867
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 867

Gly Leu Val Gly Val Gly Lys Ser Arg
1               5

<210> SEQ ID NO 868
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 868

Val Ile Gly Ala Val Gly Val Gly Met
1               5

<210> SEQ ID NO 869
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 869

Gly Gln Val Gly Val Gly Lys Ser Leu
1               5

<210> SEQ ID NO 870
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 870

Ala Thr Asp Val Gly Lys Ser Ala Trp
1               5

<210> SEQ ID NO 871
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 871

Asp Ile Gly Lys Ser Ala Leu Thr Val
1               5

<210> SEQ ID NO 872
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 872

Val Val Gly Ala Arg Gly Val Gly Met
1               5

<210> SEQ ID NO 873
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 873

Gly Asp Arg Gly Val Gly Lys Ser Tyr
1               5

<210> SEQ ID NO 874
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 874

Gly Asp Val Gly Val Gly Lys Ser Lys
1               5

<210> SEQ ID NO 875
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 875

Gly Val Asp Gly Val Gly Lys Ser Trp
1               5

<210> SEQ ID NO 876
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 876

Val Gln Gly Ala Asp Gly Val Gly Lys
1               5
```

```
<210> SEQ ID NO 877
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 877

Gly Pro Asp Gly Val Gly Lys Ser Phe
1               5

<210> SEQ ID NO 878
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 878

Gly Ser Gly Asp Val Gly Lys Ser Ile
1               5

<210> SEQ ID NO 879
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 879

Gly Met Asp Gly Val Gly Lys Ser Arg
1               5

<210> SEQ ID NO 880
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 880

Val Val Gly Ala Arg Gly Val Gly Phe
1               5

<210> SEQ ID NO 881
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 881

Asp Met Gly Lys Ser Ala Leu Thr Val
1               5
```

```
<210> SEQ ID NO 882
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 882

Val Ala Gly Ala Gly Asp Val Gly His
1               5

<210> SEQ ID NO 883
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 883

Gly Ala Val Gly Val Gly Lys Ser Cys
1               5

<210> SEQ ID NO 884
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 884

Val Ser Gly Ala Asp Gly Val Gly Met
1               5

<210> SEQ ID NO 885
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 885

Ala Val Asp Val Gly Lys Ser Ala Arg
1               5

<210> SEQ ID NO 886
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 886

Val Gln Gly Ala Asp Gly Val Gly Arg
1               5
```

<210> SEQ ID NO 887
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: GARGVGKSA (KRAS G12R)

<400> SEQUENCE: 887

Gly Ser Arg Gly Val Gly Lys Ser Ala
1               5

<210> SEQ ID NO 888
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: AGDVGKSAL (KRAS G13D)

<400> SEQUENCE: 888

Ala Tyr Asp Val Gly Lys Ser Ala Thr
1               5

<210> SEQ ID NO 889
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: VVGAVGVGK (KRAS G12V)

<400> SEQUENCE: 889

Val Asp Gly Ala Val Gly Val Gly Arg
1               5

<210> SEQ ID NO 890
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: VVGAGDVGK (KRAS G13D)

<400> SEQUENCE: 890

Val Ile Gly Ala Gly Asp Val Gly Tyr
1               5

<210> SEQ ID NO 891
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Seed: GADGVGKSA (KRAS G12D)

<400> SEQUENCE: 891

Gly Lys Asp Gly Val Gly Lys Ser Met

```
1               5

<210> SEQ ID NO 892
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 892

Gly Ser Cys Gly Val Gly Lys Ser Lys
1               5

<210> SEQ ID NO 893
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 893

Gly Asn Gly Asp Val Gly Lys Ser Phe
1               5

<210> SEQ ID NO 894
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 894

Leu Gln Val Val Gly Ala Cys Gly Ala
1               5

<210> SEQ ID NO 895
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 895

Gly Val Gly Asp Val Gly Lys Ser Ile
1               5

<210> SEQ ID NO 896
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 896
```

```
Val Asn Gly Ala Asp Gly Val Gly Arg
1               5

<210> SEQ ID NO 897
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 897

Ala Lys Asp Val Gly Lys Ser Ala Phe
1               5

<210> SEQ ID NO 898
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 898

Gly Gln Val Gly Val Gly Lys Ser Lys
1               5

<210> SEQ ID NO 899
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 899

Val Arg Gly Ala Val Gly Val Gly Met
1               5

<210> SEQ ID NO 900
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 900

Ala Trp Asp Val Gly Lys Ser Ala Ala
1               5

<210> SEQ ID NO 901
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 901
```

Val Val Gly Ala Arg Gly Val Gly Leu
1               5

<210> SEQ ID NO 902
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 902

Gly Leu Val Gly Val Gly Lys Ser Leu
1               5

<210> SEQ ID NO 903
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 903

Gly Thr Cys Gly Val Gly Lys Ser Lys
1               5

<210> SEQ ID NO 904
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 904

Gly Ser Asp Gly Val Gly Lys Ser Thr
1               5

<210> SEQ ID NO 905
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 905

Gly Gln Arg Gly Val Gly Lys Ser Leu
1               5

<210> SEQ ID NO 906
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

```
<400> SEQUENCE: 906

Asp Thr Gly Lys Ser Ala Leu Thr Leu
1               5

<210> SEQ ID NO 907
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 907

Gly Met Asp Gly Val Gly Lys Ser Cys
1               5

<210> SEQ ID NO 908
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 908

Gly Ala Val Gly Val Gly Lys Ser Thr
1               5

<210> SEQ ID NO 909
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 909

Ala Ile Asp Val Gly Lys Ser Ala Lys
1               5

<210> SEQ ID NO 910
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 910

Gly Pro Cys Gly Val Gly Lys Ser Tyr
1               5

<210> SEQ ID NO 911
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)
```

-continued

```
<400> SEQUENCE: 911

Ala Ile Asp Val Gly Lys Ser Ala Arg
1               5

<210> SEQ ID NO 912
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 912

Gly Gln Gly Asp Val Gly Lys Ser Leu
1               5

<210> SEQ ID NO 913
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 913

Val Gln Gly Ala Arg Gly Val Gly Arg
1               5

<210> SEQ ID NO 914
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 914

Gly Ile Cys Gly Val Gly Lys Ser His
1               5

<210> SEQ ID NO 915
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 915

Gly Val Cys Gly Val Gly Lys Ser Ile
1               5

<210> SEQ ID NO 916
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Seed: GADGVGKSA (KRAS G12D)

<400> SEQUENCE: 916

Gly Met Asp Gly Val Gly Lys Ser Lys
1               5

<210> SEQ ID NO 917
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 917

Gly Phe Gly Asp Val Gly Lys Ser Tyr
1               5

<210> SEQ ID NO 918
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 918

Gly Thr Asp Gly Val Gly Lys Ser Trp
1               5

<210> SEQ ID NO 919
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 919

Leu Leu Val Val Gly Ala Asp Gly Met
1               5

<210> SEQ ID NO 920
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 920

Ala Ala Asp Val Gly Lys Ser Ala Lys
1               5

<210> SEQ ID NO 921
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: GAGDVGKSA (KRAS G13D)

<400> SEQUENCE: 921

Gly Thr Gly Asp Val Gly Lys Ser Ile
1               5

<210> SEQ ID NO 922
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 922

Val Phe Gly Ala Val Gly Val Gly Lys
1               5

<210> SEQ ID NO 923
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 923

Gly Ser Cys Gly Val Gly Lys Ser Arg
1               5

<210> SEQ ID NO 924
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 924

Gly Thr Cys Gly Val Gly Lys Ser Val
1               5

<210> SEQ ID NO 925
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 925

Asp Ala Gly Lys Ser Ala Leu Thr Ala
1               5

<210> SEQ ID NO 926
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: Seed: GACGVGKSA (KRAS G12C)

<400> SEQUENCE: 926

Gly Thr Cys Gly Val Gly Lys Ser Arg
1               5

<210> SEQ ID NO 927
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 927

Val Tyr Gly Ala Val Gly Val Gly Lys
1               5

<210> SEQ ID NO 928
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 928

Gly Ile Arg Gly Val Gly Lys Ser Val
1               5

<210> SEQ ID NO 929
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 929

Val Ser Gly Ala Arg Gly Val Gly Val
1               5

<210> SEQ ID NO 930
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 930

Val Asn Gly Ala Gly Asp Val Gly Lys
1               5

<210> SEQ ID NO 931
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 931

Val Gln Gly Ala Gly Asp Val Gly Lys
1               5

<210> SEQ ID NO 932
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 932

Gly Gln Asp Gly Val Gly Lys Ser Lys
1               5

<210> SEQ ID NO 933
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 933

Gly Asn Val Gly Val Gly Lys Ser Arg
1               5

<210> SEQ ID NO 934
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 934

Gly Asn Asp Gly Val Gly Lys Ser Arg
1               5

<210> SEQ ID NO 935
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 935

Val Ala Gly Ala Val Gly Val Gly Ala
1               5

<210> SEQ ID NO 936
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 936

Val Asn Gly Ala Asp Gly Val Gly Lys
1               5

<210> SEQ ID NO 937
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 937

Gly Pro Gly Asp Val Gly Lys Ser Tyr
1               5

<210> SEQ ID NO 938
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 938

Gly Gly Cys Gly Val Gly Lys Ser Leu
1               5

<210> SEQ ID NO 939
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 939

Val Gln Gly Ala Gly Asp Val Gly Arg
1               5

<210> SEQ ID NO 940
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 940

Gly Gly Cys Gly Val Gly Lys Ser Arg
1               5

<210> SEQ ID NO 941
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 941

Gly Gln Asp Gly Val Gly Lys Ser Arg
1               5

<210> SEQ ID NO 942
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 942

Gly Gly Gly Asp Val Gly Lys Ser Leu
1               5

<210> SEQ ID NO 943
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 943

Val Thr Gly Ala Gly Asp Val Gly Phe
1               5

<210> SEQ ID NO 944
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 944

Val Ser Gly Ala Arg Gly Val Gly Ile
1               5

<210> SEQ ID NO 945
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 945

Gly Ala Arg Gly Val Gly Lys Ser Cys
1               5

<210> SEQ ID NO 946
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 946

Ala Ser Asp Val Gly Lys Ser Ala Thr
1               5

<210> SEQ ID NO 947
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 947

Val Val Gly Ala Val Gly Val Gly His
1               5

<210> SEQ ID NO 948
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 948

Gly Asp Val Gly Val Gly Lys Ser Arg
1               5

<210> SEQ ID NO 949
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 949

Ala Phe Asp Val Gly Lys Ser Ala Thr
1               5

<210> SEQ ID NO 950
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 950

Val Val Gly Ala Cys Gly Val Gly Met
1               5

<210> SEQ ID NO 951
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 951

Gly Ile Arg Gly Val Gly Lys Ser Ile
1               5

<210> SEQ ID NO 952
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 952

Val Asn Gly Ala Gly Asp Val Gly Arg
1               5

<210> SEQ ID NO 953
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 953

Gly Val Cys Gly Val Gly Lys Ser Ala
1               5

<210> SEQ ID NO 954
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 954

Val Ile Gly Ala Cys Gly Val Gly Phe
1               5

<210> SEQ ID NO 955
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 955

Gly Gly Cys Gly Val Gly Lys Ser Lys
1               5
```

```
<210> SEQ ID NO 956
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 956

Gly Phe Arg Gly Val Gly Lys Ser Tyr
1               5

<210> SEQ ID NO 957
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 957

Val Met Gly Ala Val Gly Val Gly Phe
1               5

<210> SEQ ID NO 958
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 958

Val Pro Gly Ala Gly Asp Val Gly Arg
1               5

<210> SEQ ID NO 959
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 959

Gly Pro Arg Gly Val Gly Lys Ser Gln
1               5

<210> SEQ ID NO 960
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 960

Gly Thr Cys Gly Val Gly Lys Ser Ile
1               5
```

```
<210> SEQ ID NO 961
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 961

Gly Asn Asp Gly Val Gly Lys Ser Lys
1               5

<210> SEQ ID NO 962
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 962

Gly Met Gly Asp Val Gly Lys Ser Leu
1               5

<210> SEQ ID NO 963
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 963

Gly Leu Gly Asp Val Gly Lys Ser Leu
1               5

<210> SEQ ID NO 964
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 964

Gly Cys Val Gly Val Gly Lys Ser Met
1               5

<210> SEQ ID NO 965
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 965

Val Glu Gly Ala Val Gly Val Gly Arg
1               5
```

<210> SEQ ID NO 966
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 966

Gly Asp Val Gly Val Gly Lys Ser Tyr
1               5

<210> SEQ ID NO 967
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 967

Gly Asn Cys Gly Val Gly Lys Ser Phe
1               5

<210> SEQ ID NO 968
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 968

Ala Ala Asp Val Gly Lys Ser Ala Arg
1               5

<210> SEQ ID NO 969
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 969

Gly Asn Asp Gly Val Gly Lys Ser Tyr
1               5

<210> SEQ ID NO 970
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 970

Leu Val Val Val Gly Ala Val Gly Ala

```
1               5
```

<210> SEQ ID NO 971
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 971

```
Asp Ser Gly Lys Ser Ala Leu Thr Leu
1               5
```

<210> SEQ ID NO 972
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 972

```
Val Pro Gly Ala Arg Gly Val Gly Arg
1               5
```

<210> SEQ ID NO 973
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 973

```
Val Met Gly Ala Cys Gly Val Gly Tyr
1               5
```

<210> SEQ ID NO 974
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 974

```
Ala Asp Asp Val Gly Lys Ser Ala Tyr
1               5
```

<210> SEQ ID NO 975
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 975

```
Val Phe Gly Ala Gly Asp Val Gly Lys
1               5
```

<210> SEQ ID NO 976
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 976

```
Gly Met Val Gly Val Gly Lys Ser Lys
1               5
```

<210> SEQ ID NO 977
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 977

```
Gly Val Val Gly Val Gly Lys Ser Ala
1               5
```

<210> SEQ ID NO 978
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 978

```
Gly Phe Asp Gly Val Gly Lys Ser Cys
1               5
```

<210> SEQ ID NO 979
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 979

```
Gly Pro Gly Asp Val Gly Lys Ser Ser
1               5
```

<210> SEQ ID NO 980
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 980

Gly Ser Val Gly Val Gly Lys Ser Trp
1               5

<210> SEQ ID NO 981
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 981

Gly Asp Gly Asp Val Gly Lys Ser Lys
1               5

<210> SEQ ID NO 982
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 982

Leu Thr Val Val Gly Ala Asp Gly Leu
1               5

<210> SEQ ID NO 983
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 983

Asp Ile Gly Lys Ser Ala Leu Thr Ile
1               5

<210> SEQ ID NO 984
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 984

Gly Phe Asp Gly Val Gly Lys Ser Tyr
1               5

<210> SEQ ID NO 985
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

```
<400> SEQUENCE: 985

Ala Asp Asp Val Gly Lys Ser Ala Trp
1               5

<210> SEQ ID NO 986
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 986

Leu Ile Val Val Gly Ala Val Gly Ala
1               5

<210> SEQ ID NO 987
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 987

Leu Thr Val Val Gly Ala Val Gly Ala
1               5

<210> SEQ ID NO 988
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 988

Gly Glu Arg Gly Val Gly Lys Ser Phe
1               5

<210> SEQ ID NO 989
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 989

Asp Thr Gly Lys Ser Ala Leu Thr Ile
1               5

<210> SEQ ID NO 990
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)
```

```
<400> SEQUENCE: 990

Gly Gln Val Gly Val Gly Lys Ser Arg
1               5

<210> SEQ ID NO 991
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 991

Gly Asn Gly Asp Val Gly Lys Ser Lys
1               5

<210> SEQ ID NO 992
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 992

Gly Asn Gly Asp Val Gly Lys Ser Arg
1               5

<210> SEQ ID NO 993
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 993

Val Met Gly Ala Asp Gly Val Gly Tyr
1               5

<210> SEQ ID NO 994
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 994

Gly Met Gly Asp Val Gly Lys Ser Arg
1               5

<210> SEQ ID NO 995
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: Seed: VVGADGVGK (KRAS G12D)

<400> SEQUENCE: 995

Val Asp Gly Ala Asp Gly Val Gly Lys
1               5

<210> SEQ ID NO 996
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 996

Gly Met Cys Gly Val Gly Lys Ser Leu
1               5

<210> SEQ ID NO 997
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 997

Val Pro Gly Ala Asp Gly Val Gly Arg
1               5

<210> SEQ ID NO 998
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 998

Ala Asn Asp Val Gly Lys Ser Ala Tyr
1               5

<210> SEQ ID NO 999
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 999

Ala Gly Asp Val Gly Lys Ser Ala Lys
1               5

<210> SEQ ID NO 1000
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: Seed: VVGADGVGK (KRAS G12D)

<400> SEQUENCE: 1000

Val Pro Gly Ala Asp Gly Val Gly Lys
1               5

<210> SEQ ID NO 1001
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1001

Gly Met Val Gly Val Gly Lys Ser His
1               5

<210> SEQ ID NO 1002
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1002

Gly Pro Asp Gly Val Gly Lys Ser Cys
1               5

<210> SEQ ID NO 1003
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1003

Val Ser Gly Ala Cys Gly Val Gly Leu
1               5

<210> SEQ ID NO 1004
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1004

Gly Glu Gly Asp Val Gly Lys Ser Phe
1               5

<210> SEQ ID NO 1005
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: Seed: VVGACGVGK (KRAS G12C)

<400> SEQUENCE: 1005

Val Leu Gly Ala Cys Gly Val Gly Tyr
1               5

<210> SEQ ID NO 1006
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1006

Val Gly Gly Ala Asp Gly Val Gly Tyr
1               5

<210> SEQ ID NO 1007
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1007

Gly Met Val Gly Val Gly Lys Ser Arg
1               5

<210> SEQ ID NO 1008
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1008

Val Trp Gly Ala Val Gly Val Gly Arg
1               5

<210> SEQ ID NO 1009
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1009

Gly Thr Asp Gly Val Gly Lys Ser Thr
1               5

<210> SEQ ID NO 1010
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1010

Val Leu Gly Ala Asp Gly Val Gly Tyr
1               5

<210> SEQ ID NO 1011
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1011

Val Ser Gly Ala Gly Asp Val Gly Met
1               5

<210> SEQ ID NO 1012
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1012

Gly Met Gly Asp Val Gly Lys Ser Lys
1               5

<210> SEQ ID NO 1013
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1013

Gly Asp Gly Asp Val Gly Lys Ser Arg
1               5

<210> SEQ ID NO 1014
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1014

Val Pro Gly Ala Cys Gly Val Gly Lys
1               5

<210> SEQ ID NO 1015
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1015

Gly Tyr Asp Gly Val Gly Lys Ser Ala
1               5

<210> SEQ ID NO 1016
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1016

Val Phe Gly Ala Asp Gly Val Gly Lys
1               5

<210> SEQ ID NO 1017
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1017

Val Gln Gly Ala Val Gly Val Gly Phe
1               5

<210> SEQ ID NO 1018
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1018

Gly Cys Gly Asp Val Gly Lys Ser Phe
1               5

<210> SEQ ID NO 1019
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1019

Ala Arg Asp Val Gly Lys Ser Ala Trp
1               5

<210> SEQ ID NO 1020
<211> LENGTH: 9
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1020

Gly Gly Arg Gly Val Gly Lys Ser Ala
1               5

<210> SEQ ID NO 1021
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1021

Ala Lys Asp Val Gly Lys Ser Ala Tyr
1               5

<210> SEQ ID NO 1022
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1022

Val Arg Gly Ala Val Gly Val Gly Ile
1               5

<210> SEQ ID NO 1023
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1023

Val Glu Gly Ala Asp Gly Val Gly Lys
1               5

<210> SEQ ID NO 1024
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1024

Gly Leu Cys Gly Val Gly Lys Ser Arg
1               5

<210> SEQ ID NO 1025
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1025

Gly Asp Asp Gly Val Gly Lys Ser Ile
1               5

<210> SEQ ID NO 1026
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1026

Gly Phe Val Gly Val Gly Lys Ser Tyr
1               5

<210> SEQ ID NO 1027
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1027

Asp Thr Gly Lys Ser Ala Leu Thr Met
1               5

<210> SEQ ID NO 1028
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1028

Val Ile Gly Ala Arg Gly Val Gly Tyr
1               5

<210> SEQ ID NO 1029
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1029

Val Thr Gly Ala Val Gly Val Gly His
1               5

<210> SEQ ID NO 1030
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1030

Ala Gly Asp Val Gly Lys Ser Ala Arg
1               5

<210> SEQ ID NO 1031
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1031

Gly Gln Cys Gly Val Gly Lys Ser Leu
1               5

<210> SEQ ID NO 1032
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1032

Gly Asn Val Gly Val Gly Lys Ser Met
1               5

<210> SEQ ID NO 1033
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1033

Val Met Gly Ala Gly Asp Val Gly Tyr
1               5

<210> SEQ ID NO 1034
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1034

Gly Phe Asp Gly Val Gly Lys Ser Lys
1               5
```

```
<210> SEQ ID NO 1035
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1035

Val Asp Gly Ala Gly Asp Val Gly Lys
1               5

<210> SEQ ID NO 1036
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1036

Ala Gln Asp Val Gly Lys Ser Ala Trp
1               5

<210> SEQ ID NO 1037
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1037

Gly Asp Asp Gly Val Gly Lys Ser Lys
1               5

<210> SEQ ID NO 1038
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1038

Val Thr Gly Ala Arg Gly Val Gly Ile
1               5

<210> SEQ ID NO 1039
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 1039

Leu Ser Val Val Gly Ala Asp Gly Val
1               5
```

```
<210> SEQ ID NO 1040
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1040

Val Val Gly Ala Asp Gly Val Gly Met
1               5

<210> SEQ ID NO 1041
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1041

Gly Asn Arg Gly Val Gly Lys Ser Met
1               5

<210> SEQ ID NO 1042
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1042

Val Gly Gly Ala Val Gly Val Gly Met
1               5

<210> SEQ ID NO 1043
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1043

Gly Glu Val Gly Val Gly Lys Ser Lys
1               5

<210> SEQ ID NO 1044
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1044

Leu Gln Val Val Gly Ala Val Gly Ala
1               5
```

```
<210> SEQ ID NO 1045
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1045

Gly Pro Arg Gly Val Gly Lys Ser His
1               5

<210> SEQ ID NO 1046
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1046

Gly Leu Asp Gly Val Gly Lys Ser Trp
1               5

<210> SEQ ID NO 1047
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1047

Val Thr Gly Ala Arg Gly Val Gly Val
1               5

<210> SEQ ID NO 1048
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1048

Gly Gln Gly Asp Val Gly Lys Ser Arg
1               5

<210> SEQ ID NO 1049
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1049

Gly Glu Asp Gly Val Gly Lys Ser Phe
```

<210> SEQ ID NO 1050
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1050

Val Ile Gly Ala Asp Gly Val Gly Phe
1               5

<210> SEQ ID NO 1051
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1051

Gly Gln Gly Asp Val Gly Lys Ser Lys
1               5

<210> SEQ ID NO 1052
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1052

Val Gly Gly Ala Arg Gly Val Gly Tyr
1               5

<210> SEQ ID NO 1053
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1053

Val Gln Gly Ala Arg Gly Val Gly Lys
1               5

<210> SEQ ID NO 1054
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1054

```
Gly Lys Asp Gly Val Gly Lys Ser Phe
1               5

<210> SEQ ID NO 1055
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1055

Val Arg Gly Ala Val Gly Val Gly Val
1               5

<210> SEQ ID NO 1056
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1056

Val Asp Gly Ala Cys Gly Val Gly Lys
1               5

<210> SEQ ID NO 1057
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1057

Ala Ser Asp Val Gly Lys Ser Ala Lys
1               5

<210> SEQ ID NO 1058
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1058

Gly Gln Val Gly Val Gly Lys Ser His
1               5

<210> SEQ ID NO 1059
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1059
```

```
Ala Ser Asp Val Gly Lys Ser Ala Arg
1               5

<210> SEQ ID NO 1060
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1060

Ala Ser Asp Val Gly Lys Ser Ala His
1               5

<210> SEQ ID NO 1061
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1061

Gly Glu Val Gly Val Gly Lys Ser Phe
1               5

<210> SEQ ID NO 1062
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1062

Val Leu Gly Ala Gly Asp Val Gly Tyr
1               5

<210> SEQ ID NO 1063
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1063

Gly Ala Arg Gly Val Gly Lys Ser Thr
1               5

<210> SEQ ID NO 1064
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)
```

```
<400> SEQUENCE: 1064

Asp Met Gly Lys Ser Ala Leu Thr Ile
1               5

<210> SEQ ID NO 1065
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 1065

Leu Thr Val Val Gly Ala Asp Gly Ile
1               5

<210> SEQ ID NO 1066
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1066

Gly Leu Val Gly Val Gly Lys Ser His
1               5

<210> SEQ ID NO 1067
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1067

Gly Leu Cys Gly Val Gly Lys Ser Leu
1               5

<210> SEQ ID NO 1068
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1068

Val Ile Gly Ala Arg Gly Val Gly Phe
1               5

<210> SEQ ID NO 1069
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)
```

```
<400> SEQUENCE: 1069

Gly Asp Asp Gly Val Gly Lys Ser Arg
1               5

<210> SEQ ID NO 1070
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1070

Ala Gly Asp Val Gly Lys Ser Ala Ala
1               5

<210> SEQ ID NO 1071
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1071

Val Ala Gly Ala Arg Gly Val Gly Trp
1               5

<210> SEQ ID NO 1072
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1072

Val Thr Gly Ala Asp Gly Val Gly Met
1               5

<210> SEQ ID NO 1073
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 1073

Leu Met Val Val Gly Ala Cys Gly Thr
1               5

<210> SEQ ID NO 1074
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Seed: GADGVGKSA (KRAS G12D)

<400> SEQUENCE: 1074

Gly Pro Asp Gly Val Gly Lys Ser Lys
1               5

<210> SEQ ID NO 1075
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1075

Gly Glu Cys Gly Val Gly Lys Ser Phe
1               5

<210> SEQ ID NO 1076
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1076

Gly Val Asp Gly Val Gly Lys Ser His
1               5

<210> SEQ ID NO 1077
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1077

Ala Leu Asp Val Gly Lys Ser Ala Arg
1               5

<210> SEQ ID NO 1078
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1078

Ala Thr Asp Val Gly Lys Ser Ala Lys
1               5

<210> SEQ ID NO 1079
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: GAGDVGKSA (KRAS G13D)

<400> SEQUENCE: 1079

Gly Val Gly Asp Val Gly Lys Ser Ala
1               5

<210> SEQ ID NO 1080
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1080

Gly Arg Asp Gly Val Gly Lys Ser Ala
1               5

<210> SEQ ID NO 1081
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1081

Gly Leu Cys Gly Val Gly Lys Ser Lys
1               5

<210> SEQ ID NO 1082
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1082

Ala Lys Asp Val Gly Lys Ser Ala Ile
1               5

<210> SEQ ID NO 1083
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1083

Ala Arg Asp Val Gly Lys Ser Ala Ala
1               5

<210> SEQ ID NO 1084
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: Seed: GAVGVGKSA (KRAS G12V)

<400> SEQUENCE: 1084

Gly Ile Val Gly Val Gly Lys Ser Val
1               5

<210> SEQ ID NO 1085
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1085

Gly Asp Asp Gly Val Gly Lys Ser Val
1               5

<210> SEQ ID NO 1086
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1086

Gly Glu Asp Gly Val Gly Lys Ser Tyr
1               5

<210> SEQ ID NO 1087
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1087

Asp Gly Gly Lys Ser Ala Leu Thr Leu
1               5

<210> SEQ ID NO 1088
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1088

Val Tyr Gly Ala Cys Gly Val Gly Lys
1               5

<210> SEQ ID NO 1089
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1089

Gly Ile Val Gly Val Gly Lys Ser Ile
1               5

<210> SEQ ID NO 1090
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1090

Gly Phe Val Gly Val Gly Lys Ser Lys
1               5

<210> SEQ ID NO 1091
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1091

Val Asn Gly Ala Cys Gly Val Gly Lys
1               5

<210> SEQ ID NO 1092
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1092

Gly Phe Gly Asp Val Gly Lys Ser Lys
1               5

<210> SEQ ID NO 1093
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1093

Ala Thr Asp Val Gly Lys Ser Ala Arg
1               5

<210> SEQ ID NO 1094
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1094

Val Cys Gly Ala Val Gly Val Gly Lys
1               5

<210> SEQ ID NO 1095
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1095

Gly Arg Asp Gly Val Gly Lys Ser Cys
1               5

<210> SEQ ID NO 1096
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1096

Gly Ala Val Gly Val Gly Lys Ser Gln
1               5

<210> SEQ ID NO 1097
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1097

Val Tyr Gly Ala Val Gly Val Gly Phe
1               5

<210> SEQ ID NO 1098
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1098

Gly Cys Val Gly Val Gly Lys Ser Lys
1               5

<210> SEQ ID NO 1099
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1099

Val Gly Gly Ala Arg Gly Val Gly Lys
1               5

<210> SEQ ID NO 1100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1100

Val Asp Gly Ala Asp Gly Val Gly Arg
1               5

<210> SEQ ID NO 1101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1101

Val Asp Gly Ala Cys Gly Val Gly Arg
1               5

<210> SEQ ID NO 1102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1102

Gly Tyr Asp Gly Val Gly Lys Ser Lys
1               5

<210> SEQ ID NO 1103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1103

Ala Leu Asp Val Gly Lys Ser Ala Lys
1               5

<210> SEQ ID NO 1104
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1104

Val Phe Gly Ala Gly Asp Val Gly Arg
1               5

<210> SEQ ID NO 1105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1105

Val Glu Gly Ala Gly Asp Val Gly Lys
1               5

<210> SEQ ID NO 1106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1106

Val Phe Gly Ala Asp Gly Val Gly Arg
1               5

<210> SEQ ID NO 1107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1107

Ala Leu Asp Val Gly Lys Ser Ala Ala
1               5

<210> SEQ ID NO 1108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1108

Gly Ser Asp Gly Val Gly Lys Ser His
1               5

<210> SEQ ID NO 1109
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1109

Val Arg Gly Ala Val Gly Val Gly Phe
1               5

<210> SEQ ID NO 1110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1110

Val Asn Gly Ala Val Gly Val Gly Tyr
1               5

<210> SEQ ID NO 1111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1111

Gly Ile Gly Asp Val Gly Lys Ser Val
1               5

<210> SEQ ID NO 1112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1112

Ala Arg Asp Val Gly Lys Ser Ala Cys
1               5

<210> SEQ ID NO 1113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1113

Gly Cys Val Gly Val Gly Lys Ser Leu
1               5
```

```
<210> SEQ ID NO 1114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1114

Ala Glu Asp Val Gly Lys Ser Ala Thr
1               5

<210> SEQ ID NO 1115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1115

Gly Pro Val Gly Val Gly Lys Ser Lys
1               5

<210> SEQ ID NO 1116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1116

Gly Thr Val Gly Val Gly Lys Ser Trp
1               5

<210> SEQ ID NO 1117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1117

Val Glu Gly Ala Cys Gly Val Gly Lys
1               5

<210> SEQ ID NO 1118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1118

Gly Asp Cys Gly Val Gly Lys Ser Tyr
1               5
```

```
<210> SEQ ID NO 1119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1119

Asp Glu Gly Lys Ser Ala Leu Thr Val
1               5

<210> SEQ ID NO 1120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1120

Asp Gln Gly Lys Ser Ala Leu Thr Met
1               5

<210> SEQ ID NO 1121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1121

Gly Glu Asp Gly Val Gly Lys Ser Lys
1               5

<210> SEQ ID NO 1122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1122

Val Phe Gly Ala Cys Gly Val Gly Lys
1               5

<210> SEQ ID NO 1123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1123

Val Gly Gly Ala Gly Asp Val Gly Tyr
1               5
```

```
<210> SEQ ID NO 1124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1124

Gly Cys Val Gly Val Gly Lys Ser Arg
1               5

<210> SEQ ID NO 1125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1125

Gly Phe Asp Gly Val Gly Lys Ser Arg
1               5

<210> SEQ ID NO 1126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1126

Val Asp Gly Ala Gly Asp Val Gly Arg
1               5

<210> SEQ ID NO 1127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1127

Val Ala Gly Ala Val Gly Val Gly Trp
1               5

<210> SEQ ID NO 1128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1128

Gly Phe Asp Gly Val Gly Lys Ser Trp
```

```
<210> SEQ ID NO 1129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1129

Val Arg Gly Ala Val Gly Val Gly Tyr
1               5

<210> SEQ ID NO 1130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1130

Val Ile Gly Ala Val Gly Val Gly Leu
1               5

<210> SEQ ID NO 1131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1131

Gly Ile Cys Gly Val Gly Lys Ser Val
1               5

<210> SEQ ID NO 1132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1132

Val Thr Gly Ala Cys Gly Val Gly Met
1               5

<210> SEQ ID NO 1133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1133
```

Ala Cys Asp Val Gly Lys Ser Ala Tyr
1               5

<210> SEQ ID NO 1134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1134

Val Cys Gly Ala Val Gly Val Gly Arg
1               5

<210> SEQ ID NO 1135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1135

Val Glu Gly Ala Asp Gly Val Gly Arg
1               5

<210> SEQ ID NO 1136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1136

Ala Val Asp Val Gly Lys Ser Ala His
1               5

<210> SEQ ID NO 1137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1137

Gly Asp Gly Asp Val Gly Lys Ser Tyr
1               5

<210> SEQ ID NO 1138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1138

Asp Pro Gly Lys Ser Ala Leu Thr Met
1               5

<210> SEQ ID NO 1139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1139

Gly Ser Cys Gly Val Gly Lys Ser Ala
1               5

<210> SEQ ID NO 1140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1140

Gly Ser Gly Asp Val Gly Lys Ser Trp
1               5

<210> SEQ ID NO 1141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1141

Gly Asp Cys Gly Val Gly Lys Ser Lys
1               5

<210> SEQ ID NO 1142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1142

Val Tyr Gly Ala Val Gly Val Gly Met
1               5

<210> SEQ ID NO 1143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

```
<400> SEQUENCE: 1143

Val Trp Gly Ala Cys Gly Val Gly Arg
1               5

<210> SEQ ID NO 1144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1144

Gly Thr Val Gly Val Gly Lys Ser Ala
1               5

<210> SEQ ID NO 1145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1145

Gly Ser Gly Asp Val Gly Lys Ser Ala
1               5

<210> SEQ ID NO 1146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1146

Asp Leu Gly Lys Ser Ala Leu Thr Val
1               5

<210> SEQ ID NO 1147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1147

Ala Gln Asp Val Gly Lys Ser Ala Lys
1               5

<210> SEQ ID NO 1148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)
```

-continued

<400> SEQUENCE: 1148

Ala Thr Asp Val Gly Lys Ser Ala Thr
1               5

<210> SEQ ID NO 1149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1149

Val Asn Gly Ala Cys Gly Val Gly Arg
1               5

<210> SEQ ID NO 1150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1150

Gly Gln Cys Gly Val Gly Lys Ser Lys
1               5

<210> SEQ ID NO 1151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1151

Leu Met Val Val Gly Ala Val Gly Thr
1               5

<210> SEQ ID NO 1152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1152

Val Ile Gly Ala Arg Gly Val Gly Leu
1               5

<210> SEQ ID NO 1153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: VVGAVGVGK (KRAS G12V)

<400> SEQUENCE: 1153

Val Tyr Gly Ala Val Gly Val Gly Tyr
1               5

<210> SEQ ID NO 1154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1154

Gly Asn Cys Gly Val Gly Lys Ser Lys
1               5

<210> SEQ ID NO 1155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1155

Val Thr Gly Ala Cys Gly Val Gly Leu
1               5

<210> SEQ ID NO 1156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1156

Val His Gly Ala Val Gly Val Gly Lys
1               5

<210> SEQ ID NO 1157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1157

Val Gly Gly Ala Arg Gly Val Gly Met
1               5

<210> SEQ ID NO 1158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: VVGAGDVGK (KRAS G13D)

<400> SEQUENCE: 1158

Val Pro Gly Ala Gly Asp Val Gly Lys
1               5

<210> SEQ ID NO 1159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1159

Gly Pro Gly Asp Val Gly Lys Ser Phe
1               5

<210> SEQ ID NO 1160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1160

Val Ile Gly Ala Arg Gly Val Gly Met
1               5

<210> SEQ ID NO 1161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1161

Gly Pro Arg Gly Val Gly Lys Ser Arg
1               5

<210> SEQ ID NO 1162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1162

Val Phe Gly Ala Arg Gly Val Gly Tyr
1               5

<210> SEQ ID NO 1163
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: Seed: VVGACGVGK (KRAS G12C)

<400> SEQUENCE: 1163

Val Gln Gly Ala Cys Gly Val Gly Tyr
1               5

<210> SEQ ID NO 1164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1164

Ala Asp Asp Val Gly Lys Ser Ala Lys
1               5

<210> SEQ ID NO 1165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1165

Val Ser Gly Ala Asp Gly Val Gly Leu
1               5

<210> SEQ ID NO 1166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1166

Gly Leu Asp Gly Val Gly Lys Ser Ala
1               5

<210> SEQ ID NO 1167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1167

Val Tyr Gly Ala Gly Asp Val Gly Lys
1               5

<210> SEQ ID NO 1168
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1168

Val Gly Gly Ala Arg Gly Val Gly Phe
1               5

<210> SEQ ID NO 1169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1169

Gly Val Gly Asp Val Gly Lys Ser Trp
1               5

<210> SEQ ID NO 1170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1170

Val Cys Gly Ala Val Gly Val Gly Tyr
1               5

<210> SEQ ID NO 1171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1171

Val Val Gly Ala Gly Asp Val Gly Met
1               5

<210> SEQ ID NO 1172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1172

Val Gly Gly Ala Arg Gly Val Gly Arg
1               5

<210> SEQ ID NO 1173
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1173

Gly Asn Gly Asp Val Gly Lys Ser Met
1               5

<210> SEQ ID NO 1174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1174

Gly Lys Asp Gly Val Gly Lys Ser Ile
1               5

<210> SEQ ID NO 1175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1175

Val Met Gly Ala Arg Gly Val Gly Tyr
1               5

<210> SEQ ID NO 1176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1176

Val Pro Gly Ala Arg Gly Val Gly Lys
1               5

<210> SEQ ID NO 1177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1177

Gly Val Val Gly Val Gly Lys Ser Trp
1               5

<210> SEQ ID NO 1178
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1178

Val Ala Gly Ala Cys Gly Val Gly Ile
1               5

<210> SEQ ID NO 1179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1179

Gly Cys Arg Gly Val Gly Lys Ser Met
1               5

<210> SEQ ID NO 1180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1180

Ala Met Asp Val Gly Lys Ser Ala Trp
1               5

<210> SEQ ID NO 1181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1181

Ala Asn Asp Val Gly Lys Ser Ala Lys
1               5

<210> SEQ ID NO 1182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1182

Gly Ala Val Gly Val Gly Lys Ser Ser
1               5

<210> SEQ ID NO 1183
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1183

Gly Glu Asp Gly Val Gly Lys Ser Ile
1               5

<210> SEQ ID NO 1184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1184

Ala Asn Asp Val Gly Lys Ser Ala Arg
1               5

<210> SEQ ID NO 1185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1185

Gly Cys Asp Gly Val Gly Lys Ser Tyr
1               5

<210> SEQ ID NO 1186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1186

Gly Glu Gly Asp Val Gly Lys Ser Lys
1               5

<210> SEQ ID NO 1187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1187

Ala Gln Asp Val Gly Lys Ser Ala Arg
1               5

<210> SEQ ID NO 1188
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1188

Ala Gly Asp Val Gly Lys Ser Ala Trp
1               5

<210> SEQ ID NO 1189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1189

Ala Gly Asp Val Gly Lys Ser Ala Cys
1               5

<210> SEQ ID NO 1190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1190

Gly Pro Gly Asp Val Gly Lys Ser Gly
1               5

<210> SEQ ID NO 1191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1191

Gly Ala Gly Asp Val Gly Lys Ser Cys
1               5

<210> SEQ ID NO 1192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1192

Gly Gly Arg Gly Val Gly Lys Ser His
1               5
```

```
<210> SEQ ID NO 1193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1193

Gly Ser Arg Gly Val Gly Lys Ser Trp
1               5

<210> SEQ ID NO 1194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1194

Gly Asp Arg Gly Val Gly Lys Ser Phe
1               5

<210> SEQ ID NO 1195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1195

Gly Asn Cys Gly Val Gly Lys Ser Arg
1               5

<210> SEQ ID NO 1196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1196

Val Glu Gly Ala Gly Asp Val Gly Arg
1               5

<210> SEQ ID NO 1197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1197

Val Gly Gly Ala Arg Gly Val Gly Leu
1               5
```

```
<210> SEQ ID NO 1198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1198

Gly Phe Gly Asp Val Gly Lys Ser Arg
1               5

<210> SEQ ID NO 1199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1199

Gly Pro Gly Asp Val Gly Lys Ser Lys
1               5

<210> SEQ ID NO 1200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1200

Gly Phe Cys Gly Val Gly Lys Ser Tyr
1               5

<210> SEQ ID NO 1201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1201

Val Tyr Gly Ala Asp Gly Val Gly Lys
1               5

<210> SEQ ID NO 1202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1202

Gly Ile Asp Gly Val Gly Lys Ser Thr
1               5
```

```
<210> SEQ ID NO 1203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1203

Val Ser Gly Ala Gly Asp Val Gly Leu
1               5

<210> SEQ ID NO 1204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1204

Val Trp Gly Ala Arg Gly Val Gly Arg
1               5

<210> SEQ ID NO 1205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1205

Gly Val Asp Gly Val Gly Lys Ser Thr
1               5

<210> SEQ ID NO 1206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1206

Gly Pro Asp Gly Val Gly Lys Ser Ser
1               5

<210> SEQ ID NO 1207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1207

Gly Asn Cys Gly Val Gly Lys Ser Met
```

```
<210> SEQ ID NO 1208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1208

Gly Glu Asp Gly Val Gly Lys Ser Arg
1               5

<210> SEQ ID NO 1209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1209

Gly Gln Cys Gly Val Gly Lys Ser Arg
1               5

<210> SEQ ID NO 1210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1210

Gly Pro Asp Gly Val Gly Lys Ser Tyr
1               5

<210> SEQ ID NO 1211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1211

Val Glu Gly Ala Cys Gly Val Gly Arg
1               5

<210> SEQ ID NO 1212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1212
```

-continued

```
Val Leu Gly Ala Val Gly Val Gly Phe
1               5

<210> SEQ ID NO 1213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1213

Gly Pro Val Gly Val Gly Lys Ser Trp
1               5

<210> SEQ ID NO 1214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1214

Gly Tyr Asp Gly Val Gly Lys Ser Trp
1               5

<210> SEQ ID NO 1215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1215

Gly Ile Cys Gly Val Gly Lys Ser Ile
1               5

<210> SEQ ID NO 1216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1216

Gly Thr Arg Gly Val Gly Lys Ser Ala
1               5

<210> SEQ ID NO 1217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1217
```

Val Trp Gly Ala Val Gly Val Gly Lys
1               5

<210> SEQ ID NO 1218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1218

Val Phe Gly Ala Arg Gly Val Gly Phe
1               5

<210> SEQ ID NO 1219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1219

Gly Pro Val Gly Val Gly Lys Ser Arg
1               5

<210> SEQ ID NO 1220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1220

Val Asp Gly Ala Val Gly Val Gly Tyr
1               5

<210> SEQ ID NO 1221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1221

Gly Gly Gly Asp Val Gly Lys Ser His
1               5

<210> SEQ ID NO 1222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

```
<400> SEQUENCE: 1222

Gly Gly Cys Gly Val Gly Lys Ser His
1               5

<210> SEQ ID NO 1223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1223

Val Phe Gly Ala Val Gly Val Gly Phe
1               5

<210> SEQ ID NO 1224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1224

Val Ile Gly Ala Gly Asp Val Gly Phe
1               5

<210> SEQ ID NO 1225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1225

Ala Lys Asp Val Gly Lys Ser Ala Val
1               5

<210> SEQ ID NO 1226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1226

Gly Asp Cys Gly Val Gly Lys Ser Arg
1               5

<210> SEQ ID NO 1227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)
```

<400> SEQUENCE: 1227

Val Asp Gly Ala Arg Gly Val Gly Lys
1               5

<210> SEQ ID NO 1228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1228

Gly Pro Arg Gly Val Gly Lys Ser Glu
1               5

<210> SEQ ID NO 1229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1229

Ala Pro Asp Val Gly Lys Ser Ala Tyr
1               5

<210> SEQ ID NO 1230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1230

Val Tyr Gly Ala Val Gly Val Gly Leu
1               5

<210> SEQ ID NO 1231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1231

Gly Met Gly Asp Val Gly Lys Ser His
1               5

<210> SEQ ID NO 1232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: VVGADGVGK (KRAS G12D)

<400> SEQUENCE: 1232

Val Thr Gly Ala Asp Gly Val Gly Leu
1               5

<210> SEQ ID NO 1233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1233

Gly Ala Gly Asp Val Gly Lys Ser Thr
1               5

<210> SEQ ID NO 1234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1234

Gly Pro Arg Gly Val Gly Lys Ser Lys
1               5

<210> SEQ ID NO 1235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1235

Gly Cys Asp Gly Val Gly Lys Ser Lys
1               5

<210> SEQ ID NO 1236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1236

Gly Gly Asp Gly Val Gly Lys Ser Cys
1               5

<210> SEQ ID NO 1237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: AGDVGKSAL (KRAS G13D)

<400> SEQUENCE: 1237

Ala Thr Asp Val Gly Lys Ser Ala His
1               5

<210> SEQ ID NO 1238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1238

Val Gln Gly Ala Asp Gly Val Gly Tyr
1               5

<210> SEQ ID NO 1239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1239

Val Thr Gly Ala Gly Asp Val Gly Met
1               5

<210> SEQ ID NO 1240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1240

Gly Ile Gly Asp Val Gly Lys Ser Ile
1               5

<210> SEQ ID NO 1241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1241

Gly Met Cys Gly Val Gly Lys Ser Arg
1               5

<210> SEQ ID NO 1242
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: Seed: AGDVGKSAL (KRAS G13D)

<400> SEQUENCE: 1242

Ala Met Asp Val Gly Lys Ser Ala Arg
1               5

<210> SEQ ID NO 1243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1243

Gly Cys Cys Gly Val Gly Lys Ser Phe
1               5

<210> SEQ ID NO 1244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1244

Ala Glu Asp Val Gly Lys Ser Ala Lys
1               5

<210> SEQ ID NO 1245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1245

Gly Glu Val Gly Val Gly Lys Ser Arg
1               5

<210> SEQ ID NO 1246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1246

Gly Trp Asp Gly Val Gly Lys Ser Lys
1               5

<210> SEQ ID NO 1247
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1247

Gly Ser Cys Gly Val Gly Lys Ser Trp
1               5

<210> SEQ ID NO 1248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1248

Val Val Gly Ala Cys Gly Val Gly Leu
1               5

<210> SEQ ID NO 1249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1249

Val Ser Gly Ala Val Gly Val Gly Ile
1               5

<210> SEQ ID NO 1250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1250

Ala Ile Asp Val Gly Lys Ser Ala Thr
1               5

<210> SEQ ID NO 1251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1251

Gly Thr Asp Gly Val Gly Lys Ser His
1               5

<210> SEQ ID NO 1252
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1252

Gly Ala Arg Gly Val Gly Lys Ser Arg
1               5

<210> SEQ ID NO 1253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1253

Val Ser Gly Ala Val Gly Val Gly Val
1               5

<210> SEQ ID NO 1254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1254

Val Tyr Gly Ala Arg Gly Val Gly Lys
1               5

<210> SEQ ID NO 1255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1255

Ala Met Asp Val Gly Lys Ser Ala Ala
1               5

<210> SEQ ID NO 1256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1256

Val Leu Gly Ala Arg Gly Val Gly Tyr
1               5

<210> SEQ ID NO 1257
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1257

Gly Val Arg Gly Val Gly Lys Ser Trp
1               5

<210> SEQ ID NO 1258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1258

Gly Ala Cys Gly Val Gly Lys Ser Thr
1               5

<210> SEQ ID NO 1259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1259

Gly Tyr Asp Gly Val Gly Lys Ser Arg
1               5

<210> SEQ ID NO 1260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1260

Gly Cys Asp Gly Val Gly Lys Ser Arg
1               5

<210> SEQ ID NO 1261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1261

Gly Gly Val Gly Val Gly Lys Ser Val
1               5

<210> SEQ ID NO 1262
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1262

Val Phe Gly Ala Val Gly Val Gly Tyr
1               5

<210> SEQ ID NO 1263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1263

Val Ile Gly Ala Val Gly Val Gly His
1               5

<210> SEQ ID NO 1264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1264

Val Ala Gly Ala Cys Gly Val Gly Val
1               5

<210> SEQ ID NO 1265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1265

Ala Asp Asp Val Gly Lys Ser Ala Arg
1               5

<210> SEQ ID NO 1266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1266

Asp Leu Gly Lys Ser Ala Leu Thr Ile
1               5

<210> SEQ ID NO 1267
```

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1267

Ala Gln Asp Val Gly Lys Ser Ala Cys
1               5

<210> SEQ ID NO 1268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1268

Gly Lys Asp Gly Val Gly Lys Ser Val
1               5

<210> SEQ ID NO 1269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1269

Gly Cys Gly Asp Val Gly Lys Ser Arg
1               5

<210> SEQ ID NO 1270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1270

Gly Pro Asp Gly Val Gly Lys Ser Arg
1               5

<210> SEQ ID NO 1271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1271

Leu Ala Val Val Gly Ala Val Gly Leu
1               5
```

```
<210> SEQ ID NO 1272
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1272

Gly Cys Gly Asp Val Gly Lys Ser Lys
1               5

<210> SEQ ID NO 1273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1273

Gly Leu Gly Asp Val Gly Lys Ser His
1               5

<210> SEQ ID NO 1274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 1274

Leu Met Val Val Gly Ala Arg Gly Met
1               5

<210> SEQ ID NO 1275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 1275

Leu Leu Val Val Gly Ala Arg Gly Met
1               5

<210> SEQ ID NO 1276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1276

Ala Met Asp Val Gly Lys Ser Ala Lys
1               5
```

```
<210> SEQ ID NO 1277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 1277

Leu Leu Val Val Gly Ala Cys Gly Thr
1               5

<210> SEQ ID NO 1278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1278

Gly Ala Arg Gly Val Gly Lys Ser Lys
1               5

<210> SEQ ID NO 1279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1279

Val Thr Gly Ala Gly Asp Val Gly Leu
1               5

<210> SEQ ID NO 1280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1280

Gly Met Asp Gly Val Gly Lys Ser Trp
1               5

<210> SEQ ID NO 1281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1281

Val Asp Gly Ala Arg Gly Val Gly Arg
1               5
```

```
<210> SEQ ID NO 1282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1282

Gly Phe Val Gly Val Gly Lys Ser Arg
1               5

<210> SEQ ID NO 1283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1283

Gly Arg Asp Gly Val Gly Lys Ser Tyr
1               5

<210> SEQ ID NO 1284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1284

Asp Ile Gly Lys Ser Ala Leu Thr Leu
1               5

<210> SEQ ID NO 1285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1285

Gly Phe Val Gly Val Gly Lys Ser Phe
1               5

<210> SEQ ID NO 1286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1286

Gly Ala Asp Gly Val Gly Lys Ser Ser
```

```
<210> SEQ ID NO 1287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1287

Gly Cys Gly Asp Val Gly Lys Ser Met
1               5

<210> SEQ ID NO 1288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1288

Val Ser Gly Ala Asp Gly Val Gly His
1               5

<210> SEQ ID NO 1289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1289

Gly Tyr Gly Asp Val Gly Lys Ser Tyr
1               5

<210> SEQ ID NO 1290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1290

Gly Tyr Val Gly Val Gly Lys Ser Lys
1               5

<210> SEQ ID NO 1291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1291
```

Gly Phe Cys Gly Val Gly Lys Ser Lys
1               5

<210> SEQ ID NO 1292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1292

Gly Ala Cys Gly Val Gly Lys Ser Cys
1               5

<210> SEQ ID NO 1293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1293

Val Gly Gly Ala Cys Gly Val Gly Phe
1               5

<210> SEQ ID NO 1294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1294

Gly Phe Gly Asp Val Gly Lys Ser Phe
1               5

<210> SEQ ID NO 1295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1295

Gly Gly Asp Gly Val Gly Lys Ser Ala
1               5

<210> SEQ ID NO 1296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1296

```
Gly Trp Asp Gly Val Gly Lys Ser Arg
1               5
```

<210> SEQ ID NO 1297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1297

```
Gly Met Cys Gly Val Gly Lys Ser Lys
1               5
```

<210> SEQ ID NO 1298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1298

```
Gly Tyr Gly Asp Val Gly Lys Ser Lys
1               5
```

<210> SEQ ID NO 1299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1299

```
Gly Glu Cys Gly Val Gly Lys Ser Lys
1               5
```

<210> SEQ ID NO 1300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1300

```
Val Gly Gly Ala Val Gly Val Gly Leu
1               5
```

<210> SEQ ID NO 1301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1301

Ala Phe Asp Val Gly Lys Ser Ala Lys
1               5

<210> SEQ ID NO 1302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1302

Val Val Gly Ala Asp Gly Val Gly Leu
1               5

<210> SEQ ID NO 1303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1303

Gly Glu Arg Gly Val Gly Lys Ser Met
1               5

<210> SEQ ID NO 1304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1304

Val Tyr Gly Ala Gly Asp Val Gly Arg
1               5

<210> SEQ ID NO 1305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 1305

Leu Ala Val Val Gly Ala Cys Gly Leu
1               5

<210> SEQ ID NO 1306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1306

Asp Met Gly Lys Ser Ala Leu Thr Leu
1               5

<210> SEQ ID NO 1307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1307

Val Tyr Gly Ala Asp Gly Val Gly Arg
1               5

<210> SEQ ID NO 1308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1308

Gly Ala Arg Gly Val Gly Lys Ser Pro
1               5

<210> SEQ ID NO 1309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1309

Gly His Asp Gly Val Gly Lys Ser Tyr
1               5

<210> SEQ ID NO 1310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1310

Val Cys Gly Ala Asp Gly Val Gly Lys
1               5

<210> SEQ ID NO 1311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: GADGVGKSA (KRAS G12D)

<400> SEQUENCE: 1311

Gly Glu Asp Gly Val Gly Lys Ser Val
1               5

<210> SEQ ID NO 1312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1312

Gly Glu Gly Asp Val Gly Lys Ser Arg
1               5

<210> SEQ ID NO 1313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1313

Val Pro Gly Ala Val Gly Val Gly Tyr
1               5

<210> SEQ ID NO 1314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1314

Val Cys Gly Ala Asp Gly Val Gly Arg
1               5

<210> SEQ ID NO 1315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1315

Gly Gln Gly Asp Val Gly Lys Ser His
1               5

<210> SEQ ID NO 1316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: Seed: VVGAGDVGK (KRAS G13D)

<400> SEQUENCE: 1316

Val Cys Gly Ala Gly Asp Val Gly Lys
1               5

<210> SEQ ID NO 1317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1317

Gly Leu Arg Gly Val Gly Lys Ser His
1               5

<210> SEQ ID NO 1318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1318

Gly Met Arg Gly Val Gly Lys Ser His
1               5

<210> SEQ ID NO 1319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1319

Gly Met Asp Gly Val Gly Lys Ser Ala
1               5

<210> SEQ ID NO 1320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1320

Val Ala Gly Ala Asp Gly Val Gly Ile
1               5

<210> SEQ ID NO 1321
<211> LENGTH: 9
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<223> OTHER INFORMATION: Seed: DVGKSALTI (KRAS G13D)

<400> SEQUENCE: 1321

Asp Glu Gly Lys Ser Ala Leu Thr Ile
1               5

<210> SEQ ID NO 1322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1322

Ala Val Asp Val Gly Lys Ser Ala Thr
1               5

<210> SEQ ID NO 1323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1323

Ala Ala Asp Val Gly Lys Ser Ala Ser
1               5

<210> SEQ ID NO 1324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1324

Gly Ala Arg Gly Val Gly Lys Ser Gln
1               5

<210> SEQ ID NO 1325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 1325

Leu Ala Val Val Gly Ala Cys Gly Ile
1               5

<210> SEQ ID NO 1326
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1326

Val Ile Gly Ala Cys Gly Val Gly Met
1               5

<210> SEQ ID NO 1327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1327

Gly Trp Asp Gly Val Gly Lys Ser Tyr
1               5

<210> SEQ ID NO 1328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1328

Val His Gly Ala Asp Gly Val Gly Lys
1               5

<210> SEQ ID NO 1329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1329

Gly Gln Arg Gly Val Gly Lys Ser His
1               5

<210> SEQ ID NO 1330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1330

Gly Ala Val Gly Val Gly Lys Ser Pro
1               5

<210> SEQ ID NO 1331
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1331

Val Ala Gly Ala Asp Gly Val Gly Val
1               5

<210> SEQ ID NO 1332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1332

Val Gln Gly Ala Gly Asp Val Gly Tyr
1               5

<210> SEQ ID NO 1333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1333

Val Glu Gly Ala Val Gly Val Gly Tyr
1               5

<210> SEQ ID NO 1334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1334

Val Asp Gly Ala Cys Gly Val Gly Tyr
1               5

<210> SEQ ID NO 1335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1335

Val Phe Gly Ala Val Gly Val Gly Met
1               5

<210> SEQ ID NO 1336
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1336

Leu Ala Val Val Gly Ala Val Gly Ile
1               5

<210> SEQ ID NO 1337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1337

Gly Phe Asp Gly Val Gly Lys Ser Ala
1               5

<210> SEQ ID NO 1338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1338

Gly Thr Gly Asp Val Gly Lys Ser Trp
1               5

<210> SEQ ID NO 1339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1339

Val Trp Gly Ala Asp Gly Val Gly Lys
1               5

<210> SEQ ID NO 1340
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1340

Gly Gly Asp Gly Val Gly Lys Ser Trp
1               5

<210> SEQ ID NO 1341
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1341

Val Glu Gly Ala Arg Gly Val Gly Lys
1               5

<210> SEQ ID NO 1342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1342

Val Thr Gly Ala Val Gly Val Gly Val
1               5

<210> SEQ ID NO 1343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1343

Gly Glu Gly Asp Val Gly Lys Ser Met
1               5

<210> SEQ ID NO 1344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1344

Asp Leu Gly Lys Ser Ala Leu Thr Phe
1               5

<210> SEQ ID NO 1345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1345

Gly Pro Asp Gly Val Gly Lys Ser Gly
1               5

<210> SEQ ID NO 1346
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1346

Gly Trp Val Gly Val Gly Lys Ser Lys
1               5

<210> SEQ ID NO 1347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1347

Gly Trp Gly Asp Val Gly Lys Ser Lys
1               5

<210> SEQ ID NO 1348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1348

Val His Gly Ala Gly Asp Val Gly Lys
1               5

<210> SEQ ID NO 1349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1349

Val Trp Gly Ala Gly Asp Val Gly Lys
1               5

<210> SEQ ID NO 1350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1350

Val Thr Gly Ala Val Gly Val Gly Ile
1               5
```

```
<210> SEQ ID NO 1351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1351

Val Phe Gly Ala Arg Gly Val Gly Lys
1               5

<210> SEQ ID NO 1352
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1352

Asp Met Gly Lys Ser Ala Leu Thr Phe
1               5

<210> SEQ ID NO 1353
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1353

Gly Met Cys Gly Val Gly Lys Ser His
1               5

<210> SEQ ID NO 1354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1354

Val Val Gly Ala Asp Gly Val Gly His
1               5

<210> SEQ ID NO 1355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1355

Gly Tyr Val Gly Val Gly Lys Ser Tyr
1               5
```

```
<210> SEQ ID NO 1356
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGARGV (KRAS G12R)

<400> SEQUENCE: 1356

Leu Ile Val Val Gly Ala Arg Gly Leu
1               5

<210> SEQ ID NO 1357
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1357

Gly Tyr Arg Gly Val Gly Lys Ser Tyr
1               5

<210> SEQ ID NO 1358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1358

Gly Asp Val Gly Val Gly Lys Ser Phe
1               5

<210> SEQ ID NO 1359
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1359

Gly Val Cys Gly Val Gly Lys Ser Trp
1               5

<210> SEQ ID NO 1360
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1360

Ala Glu Asp Val Gly Lys Ser Ala Arg
1               5
```

```
<210> SEQ ID NO 1361
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1361

Gly Ile Asp Gly Val Gly Lys Ser His
1               5

<210> SEQ ID NO 1362
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1362

Val Ser Gly Ala Cys Gly Val Gly His
1               5

<210> SEQ ID NO 1363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1363

Gly Glu Val Gly Val Gly Lys Ser Met
1               5

<210> SEQ ID NO 1364
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1364

Val Cys Gly Ala Gly Asp Val Gly Arg
1               5

<210> SEQ ID NO 1365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1365

Gly Gln Cys Gly Val Gly Lys Ser His
```

```
<210> SEQ ID NO 1366
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1366

Ala Phe Asp Val Gly Lys Ser Ala Arg
1               5

<210> SEQ ID NO 1367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1367

Val Asp Gly Ala Arg Gly Val Gly Tyr
1               5

<210> SEQ ID NO 1368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1368

Gly Met Arg Gly Val Gly Lys Ser Ala
1               5

<210> SEQ ID NO 1369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1369

Ala Asp Asp Val Gly Lys Ser Ala Cys
1               5

<210> SEQ ID NO 1370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1370
```

-continued

Val Gln Gly Ala Val Gly Val Gly Met
1               5

<210> SEQ ID NO 1371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1371

Leu Ile Val Val Gly Ala Val Gly Met
1               5

<210> SEQ ID NO 1372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1372

Gly Pro Gly Asp Val Gly Lys Ser Arg
1               5

<210> SEQ ID NO 1373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1373

Val Thr Gly Ala Cys Gly Val Gly His
1               5

<210> SEQ ID NO 1374
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1374

Val Met Gly Ala Arg Gly Val Gly Phe
1               5

<210> SEQ ID NO 1375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1375

```
Asp Ile Gly Lys Ser Ala Leu Thr Met
1               5

<210> SEQ ID NO 1376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1376

Val Asn Gly Ala Arg Gly Val Gly Lys
1               5

<210> SEQ ID NO 1377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1377

Gly Trp Asp Gly Val Gly Lys Ser Cys
1               5

<210> SEQ ID NO 1378
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1378

Gly Gln Asp Gly Val Gly Lys Ser Trp
1               5

<210> SEQ ID NO 1379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1379

Val Met Gly Ala Cys Gly Val Gly Phe
1               5

<210> SEQ ID NO 1380
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)
```

```
-continued

<400> SEQUENCE: 1380

Gly Leu Arg Gly Val Gly Lys Ser Ala
1               5

<210> SEQ ID NO 1381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1381

Gly Ala Gly Asp Val Gly Lys Ser Gln
1               5

<210> SEQ ID NO 1382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1382

Val His Gly Ala Val Gly Val Gly Arg
1               5

<210> SEQ ID NO 1383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1383

Ala Tyr Asp Val Gly Lys Ser Ala Lys
1               5

<210> SEQ ID NO 1384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1384

Gly Pro Arg Gly Val Gly Lys Ser Asn
1               5

<210> SEQ ID NO 1385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)
```

```
<400> SEQUENCE: 1385

Gly Ile Val Gly Val Gly Lys Ser Trp
1               5

<210> SEQ ID NO 1386
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1386

Gly Phe Arg Gly Val Gly Lys Ser Phe
1               5

<210> SEQ ID NO 1387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1387

Gly Cys Asp Gly Val Gly Lys Ser Ala
1               5

<210> SEQ ID NO 1388
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1388

Ala Asp Asp Val Gly Lys Ser Ala Ala
1               5

<210> SEQ ID NO 1389
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1389

Gly Gln Val Gly Val Gly Lys Ser Trp
1               5

<210> SEQ ID NO 1390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Seed: GAVGVGKSA (KRAS G12V)

<400> SEQUENCE: 1390

Gly Gly Val Gly Val Gly Lys Ser Ile
1               5

<210> SEQ ID NO 1391
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1391

Gly Ile Gly Asp Val Gly Lys Ser Trp
1               5

<210> SEQ ID NO 1392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAGDV (KRAS G13D)

<400> SEQUENCE: 1392

Leu Met Val Val Gly Ala Gly Asp Leu
1               5

<210> SEQ ID NO 1393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1393

Val Gly Gly Ala Asp Gly Val Gly Phe
1               5

<210> SEQ ID NO 1394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1394

Gly Leu Cys Gly Val Gly Lys Ser His
1               5

<210> SEQ ID NO 1395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: LVVVGARGV (KRAS G12R)

<400> SEQUENCE: 1395

Leu Gln Val Val Gly Ala Arg Gly Leu
1               5

<210> SEQ ID NO 1396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1396

Val Ala Gly Ala Gly Asp Val Gly Ile
1               5

<210> SEQ ID NO 1397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1397

Gly Thr Cys Gly Val Gly Lys Ser Trp
1               5

<210> SEQ ID NO 1398
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 1398

Leu Val Val Val Gly Ala Asp Gly Ala
1               5

<210> SEQ ID NO 1399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1399

Gly Thr Cys Gly Val Gly Lys Ser Ala
1               5

<210> SEQ ID NO 1400
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: Seed: GADGVGKSA (KRAS G12D)

<400> SEQUENCE: 1400

Gly His Asp Gly Val Gly Lys Ser Lys
1               5

<210> SEQ ID NO 1401
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1401

Gly Asn Val Gly Val Gly Lys Ser Leu
1               5

<210> SEQ ID NO 1402
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1402

Val Phe Gly Ala Arg Gly Val Gly Met
1               5

<210> SEQ ID NO 1403
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1403

Gly Asn Arg Gly Val Gly Lys Ser Leu
1               5

<210> SEQ ID NO 1404
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1404

Gly Pro Cys Gly Val Gly Lys Ser Trp
1               5

<210> SEQ ID NO 1405
<211> LENGTH: 9
<212> TYPE: PRT
<213> ORGANISM: Artificial Sequence
<220> FEATURE:
```

```
-continued

<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1405

Gly Thr Gly Asp Val Gly Lys Ser Ala
1               5

<210> SEQ ID NO 1406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1406

Leu Ser Val Val Gly Ala Val Gly Leu
1               5

<210> SEQ ID NO 1407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1407

Asp Met Gly Lys Ser Ala Leu Thr Tyr
1               5

<210> SEQ ID NO 1408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1408

Gly Glu Cys Gly Val Gly Lys Ser Met
1               5

<210> SEQ ID NO 1409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1409

Gly Ala Asp Gly Val Gly Lys Ser Pro
1               5

<210> SEQ ID NO 1410
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1410

Val Gly Gly Ala Val Gly Val Gly His
1               5

<210> SEQ ID NO 1411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1411

Gly Ala Arg Gly Val Gly Lys Ser Ser
1               5

<210> SEQ ID NO 1412
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1412

Gly Pro Cys Gly Val Gly Lys Ser Lys
1               5

<210> SEQ ID NO 1413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1413

Gly Pro Cys Gly Val Gly Lys Ser Arg
1               5

<210> SEQ ID NO 1414
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1414

Val Asp Gly Ala Asp Gly Val Gly Tyr
1               5

<210> SEQ ID NO 1415
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1415

Val Met Gly Ala Arg Gly Val Gly Met
1               5

<210> SEQ ID NO 1416
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1416

Gly Pro Val Gly Val Gly Lys Ser Gln
1               5

<210> SEQ ID NO 1417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1417

Val Met Gly Ala Arg Gly Val Gly Leu
1               5

<210> SEQ ID NO 1418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1418

Val Phe Gly Ala Val Gly Val Gly Leu
1               5

<210> SEQ ID NO 1419
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1419

Val Trp Gly Ala Asp Gly Val Gly Arg
1               5

<210> SEQ ID NO 1420
<211> LENGTH: 9
```

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1420

Asp Asn Gly Lys Ser Ala Leu Thr Val
1               5

<210> SEQ ID NO 1421
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1421

Val Asn Gly Ala Cys Gly Val Gly Tyr
1               5

<210> SEQ ID NO 1422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1422

Val Val Gly Ala Gly Asp Val Gly Leu
1               5

<210> SEQ ID NO 1423
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1423

Gly Cys Arg Gly Val Gly Lys Ser Leu
1               5

<210> SEQ ID NO 1424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1424

Val Leu Gly Ala Arg Gly Val Gly Phe
1               5

<210> SEQ ID NO 1425
```

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1425

Gly Ile Arg Gly Val Gly Lys Ser Trp
1               5

<210> SEQ ID NO 1426
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1426

Val Cys Gly Ala Cys Gly Val Gly Lys
1               5

<210> SEQ ID NO 1427
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1427

Val Met Gly Ala Val Gly Val Gly Leu
1               5

<210> SEQ ID NO 1428
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1428

Gly Gly Arg Gly Val Gly Lys Ser Val
1               5

<210> SEQ ID NO 1429
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1429

Ala Ala Asp Val Gly Lys Ser Ala Pro
1               5
```

```
<210> SEQ ID NO 1430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1430

Val Trp Gly Ala Gly Asp Val Gly Arg
1               5

<210> SEQ ID NO 1431
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1431

Val Leu Gly Ala Val Gly Val Gly Leu
1               5

<210> SEQ ID NO 1432
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1432

Val Thr Gly Ala Arg Gly Val Gly His
1               5

<210> SEQ ID NO 1433
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1433

Val Met Gly Ala Val Gly Val Gly Met
1               5

<210> SEQ ID NO 1434
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1434

Gly His Val Gly Val Gly Lys Ser Lys
1               5
```

```
<210> SEQ ID NO 1435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1435

Val Ala Gly Ala Val Gly Val Gly Gln
1               5

<210> SEQ ID NO 1436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1436

Gly Arg Asp Gly Val Gly Lys Ser Trp
1               5

<210> SEQ ID NO 1437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1437

Gly Ile Gly Asp Val Gly Lys Ser Ala
1               5

<210> SEQ ID NO 1438
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1438

Asp Cys Gly Lys Ser Ala Leu Thr Val
1               5

<210> SEQ ID NO 1439
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1439

Val Val Gly Ala Cys Gly Val Gly His
1               5
```

```
<210> SEQ ID NO 1440
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1440

Asp Leu Gly Lys Ser Ala Leu Thr Tyr
1               5

<210> SEQ ID NO 1441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1441

Gly Tyr Cys Gly Val Gly Lys Ser Lys
1               5

<210> SEQ ID NO 1442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1442

Ala Cys Asp Val Gly Lys Ser Ala Cys
1               5

<210> SEQ ID NO 1443
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1443

Gly Asp Asp Gly Val Gly Lys Ser Tyr
1               5

<210> SEQ ID NO 1444
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1444

Gly Pro Val Gly Val Gly Lys Ser Glu
```

```
<210> SEQ ID NO 1445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1445

Val Ile Gly Ala Asp Gly Val Gly Met
1               5

<210> SEQ ID NO 1446
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1446

Ala Cys Asp Val Gly Lys Ser Ala Ala
1               5

<210> SEQ ID NO 1447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1447

Val Asn Gly Ala Asp Gly Val Gly Tyr
1               5

<210> SEQ ID NO 1448
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1448

Gly Phe Val Gly Val Gly Lys Ser Met
1               5

<210> SEQ ID NO 1449
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1449
```

```
Val Asn Gly Ala Arg Gly Val Gly Arg
1               5

<210> SEQ ID NO 1450
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1450

Val Leu Gly Ala Arg Gly Val Gly Met
1               5

<210> SEQ ID NO 1451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1451

Gly Gln Gly Asp Val Gly Lys Ser Trp
1               5

<210> SEQ ID NO 1452
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 1452

Leu Ile Val Val Gly Ala Asp Gly Ala
1               5

<210> SEQ ID NO 1453
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1453

Gly Ile Val Gly Val Gly Lys Ser Ala
1               5

<210> SEQ ID NO 1454
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1454
```

```
Val His Gly Ala Cys Gly Val Gly Lys
1               5

<210> SEQ ID NO 1455
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAGDV (KRAS G13D)

<400> SEQUENCE: 1455

Leu Ile Val Val Gly Ala Gly Asp Val
1               5

<210> SEQ ID NO 1456
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1456

Val Ala Gly Ala Gly Asp Val Gly Val
1               5

<210> SEQ ID NO 1457
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1457

Gly Asp Cys Gly Val Gly Lys Ser Phe
1               5

<210> SEQ ID NO 1458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1458

Gly Phe Cys Gly Val Gly Lys Ser Arg
1               5

<210> SEQ ID NO 1459
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)
```

```
<400> SEQUENCE: 1459

Gly Glu Cys Gly Val Gly Lys Ser Arg
1               5

<210> SEQ ID NO 1460
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1460

Gly Thr Arg Gly Val Gly Lys Ser Trp
1               5

<210> SEQ ID NO 1461
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1461

Gly Asp Gly Asp Val Gly Lys Ser Phe
1               5

<210> SEQ ID NO 1462
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAVGVGKSA (KRAS G12V)

<400> SEQUENCE: 1462

Gly Asn Val Gly Val Gly Lys Ser His
1               5

<210> SEQ ID NO 1463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1463

Gly Ile Cys Gly Val Gly Lys Ser Ala
1               5

<210> SEQ ID NO 1464
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)
```

<400> SEQUENCE: 1464

Val Trp Gly Ala Cys Gly Val Gly Lys
1               5

<210> SEQ ID NO 1465
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1465

Gly Cys Cys Gly Val Gly Lys Ser Met
1               5

<210> SEQ ID NO 1466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAGDV (KRAS G13D)

<400> SEQUENCE: 1466

Leu Met Val Val Gly Ala Gly Asp Ile
1               5

<210> SEQ ID NO 1467
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1467

Val Ala Gly Ala Cys Gly Val Gly Trp
1               5

<210> SEQ ID NO 1468
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1468

Gly Tyr Gly Asp Val Gly Lys Ser Arg
1               5

<210> SEQ ID NO 1469
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Seed: LVVVGARGV (KRAS G12R)

<400> SEQUENCE: 1469

Leu Gln Val Val Gly Ala Arg Gly Ile
1               5

<210> SEQ ID NO 1470
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1470

Leu Leu Val Val Gly Ala Val Gly Thr
1               5

<210> SEQ ID NO 1471
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1471

Val Ser Gly Ala Gly Asp Val Gly His
1               5

<210> SEQ ID NO 1472
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1472

Ala Ile Asp Val Gly Lys Ser Ala His
1               5

<210> SEQ ID NO 1473
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1473

Val Ser Gly Ala Arg Gly Val Gly Trp
1               5

<210> SEQ ID NO 1474
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Seed: GACGVGKSA (KRAS G12C)

<400> SEQUENCE: 1474

Gly Ala Cys Gly Val Gly Lys Ser Gln
1               5

<210> SEQ ID NO 1475
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1475

Val Gln Gly Ala Cys Gly Val Gly Phe
1               5

<210> SEQ ID NO 1476
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1476

Val Cys Gly Ala Cys Gly Val Gly Tyr
1               5

<210> SEQ ID NO 1477
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1477

Val Cys Gly Ala Asp Gly Val Gly Tyr
1               5

<210> SEQ ID NO 1478
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAGDV (KRAS G13D)

<400> SEQUENCE: 1478

Leu Leu Val Val Gly Ala Gly Asp Leu
1               5

<210> SEQ ID NO 1479
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<223> OTHER INFORMATION: Seed: AGDVGKSAL (KRAS G13D)

<400> SEQUENCE: 1479

Ala Cys Asp Val Gly Lys Ser Ala Trp
1               5

<210> SEQ ID NO 1480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGADGV (KRAS G12D)

<400> SEQUENCE: 1480

Leu Ala Val Val Gly Ala Asp Gly Leu
1               5

<210> SEQ ID NO 1481
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1481

Val Cys Gly Ala Val Gly Val Gly Phe
1               5

<210> SEQ ID NO 1482
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1482

Val His Gly Ala Asp Gly Val Gly Arg
1               5

<210> SEQ ID NO 1483
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1483

Gly Cys Cys Gly Val Gly Lys Ser Lys
1               5

<210> SEQ ID NO 1484
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1484

Ala Trp Asp Val Gly Lys Ser Ala Thr
1               5

<210> SEQ ID NO 1485
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 1485

Leu Ser Val Val Gly Ala Cys Gly Ile
1               5

<210> SEQ ID NO 1486
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1486

Gly Cys Cys Gly Val Gly Lys Ser Arg
1               5

<210> SEQ ID NO 1487
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1487

Leu Ser Val Val Gly Ala Val Gly Ile
1               5

<210> SEQ ID NO 1488
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1488

Ala Tyr Asp Val Gly Lys Ser Ala Arg
1               5

<210> SEQ ID NO 1489
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1489

Val Leu Gly Ala Arg Gly Val Gly Leu
1               5

<210> SEQ ID NO 1490
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1490

Leu Gln Val Val Gly Ala Val Gly Met
1               5

<210> SEQ ID NO 1491
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGAVGV (KRAS G12V)

<400> SEQUENCE: 1491

Leu Thr Val Val Gly Ala Val Gly Met
1               5

<210> SEQ ID NO 1492
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1492

Val Thr Gly Ala Asp Gly Val Gly His
1               5

<210> SEQ ID NO 1493
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1493

Val Gln Gly Ala Asp Gly Val Gly Phe
1               5

<210> SEQ ID NO 1494
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1494

Gly Tyr Asp Gly Val Gly Lys Ser Thr
1               5

<210> SEQ ID NO 1495
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1495

Val Ile Gly Ala Cys Gly Val Gly Leu
1               5

<210> SEQ ID NO 1496
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1496

Val Leu Gly Ala Val Gly Val Gly Met
1               5

<210> SEQ ID NO 1497
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 1497

Leu Ser Val Val Gly Ala Cys Gly Leu
1               5

<210> SEQ ID NO 1498
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAGDVGK (KRAS G13D)

<400> SEQUENCE: 1498

Val Asn Gly Ala Gly Asp Val Gly Tyr
1               5

<210> SEQ ID NO 1499
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1499

Val Met Gly Ala Asp Gly Val Gly Phe
1               5

<210> SEQ ID NO 1500
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1500

Gly Trp Gly Asp Val Gly Lys Ser Arg
1               5

<210> SEQ ID NO 1501
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1501

Ala Trp Asp Val Gly Lys Ser Ala Lys
1               5

<210> SEQ ID NO 1502
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1502

Gly Asn Gly Asp Val Gly Lys Ser Leu
1               5

<210> SEQ ID NO 1503
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGAVGVGK (KRAS G12V)

<400> SEQUENCE: 1503

Val Ser Gly Ala Val Gly Val Gly Trp
1               5

<210> SEQ ID NO 1504
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1504

Gly Gln Arg Gly Val Gly Lys Ser Val
1               5

<210> SEQ ID NO 1505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1505

Val Phe Gly Ala Arg Gly Val Gly Leu
1               5

<210> SEQ ID NO 1506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1506

Val Gly Gly Ala Cys Gly Val Gly Met
1               5

<210> SEQ ID NO 1507
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1507

Asp Leu Gly Lys Ser Ala Leu Thr Leu
1               5

<210> SEQ ID NO 1508
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1508

Gly Val Arg Gly Val Gly Lys Ser Cys
1               5
```

```
<210> SEQ ID NO 1509
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: LVVVGACGV (KRAS G12C)

<400> SEQUENCE: 1509

Leu Gln Val Val Gly Ala Cys Gly Met
1               5

<210> SEQ ID NO 1510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1510

Val Tyr Gly Ala Arg Gly Val Gly Tyr
1               5

<210> SEQ ID NO 1511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGADGVGK (KRAS G12D)

<400> SEQUENCE: 1511

Val Tyr Gly Ala Asp Gly Val Gly Tyr
1               5

<210> SEQ ID NO 1512
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1512

Gly Gly Cys Gly Val Gly Lys Ser Val
1               5

<210> SEQ ID NO 1513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGARGVGK (KRAS G12R)

<400> SEQUENCE: 1513

Val Glu Gly Ala Arg Gly Val Gly Arg
1               5
```

```
<210> SEQ ID NO 1514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: VVGACGVGK (KRAS G12C)

<400> SEQUENCE: 1514

Val Cys Gly Ala Cys Gly Val Gly Arg
1               5

<210> SEQ ID NO 1515
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1515

Gly Gly Arg Gly Val Gly Lys Ser Ile
1               5

<210> SEQ ID NO 1516
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GACGVGKSA (KRAS G12C)

<400> SEQUENCE: 1516

Gly Tyr Cys Gly Val Gly Lys Ser Tyr
1               5

<210> SEQ ID NO 1517
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1517

Ala Pro Asp Val Gly Lys Ser Ala Lys
1               5

<210> SEQ ID NO 1518
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: DVGKSALTI (KRAS G13D)

<400> SEQUENCE: 1518

Asp Glu Gly Lys Ser Ala Leu Thr Leu
1               5
```

<210> SEQ ID NO 1519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GARGVGKSA (KRAS G12R)

<400> SEQUENCE: 1519

Gly Glu Arg Gly Val Gly Lys Ser Leu
1               5

<210> SEQ ID NO 1520
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GADGVGKSA (KRAS G12D)

<400> SEQUENCE: 1520

Gly Cys Asp Gly Val Gly Lys Ser Trp
1               5

<210> SEQ ID NO 1521
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: GAGDVGKSA (KRAS G13D)

<400> SEQUENCE: 1521

Gly Trp Gly Asp Val Gly Lys Ser Tyr
1               5

<210> SEQ ID NO 1522
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Seed: AGDVGKSAL (KRAS G13D)

<400> SEQUENCE: 1522

Ala Cys Asp Val Gly Lys Ser Ala Lys
1               5

<210> SEQ ID NO 1523
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1523

Met Arg Val Thr Ala Pro Arg Thr Leu Ile Leu Leu Leu Ser Gly Ala
1               5                   10                  15

-continued

```
Leu Ala Leu Thr Glu Thr Trp Ala Gly Ser Gly Ser Gly Gly
            20              25              30

Gly Ser Gly Gly Gly Ala Asp Gly Val Gly Lys Ser Met Gly Gly Ser
        35              40              45

Gly Gly Gly Gly Ser Gly Gly Leu Met Val Val Gly Ala Asp Gly Val
        50              55              60

Gly Gly Ser Gly Gly Gly Gly Ser Gly Gly Gly Ala Val Gly Val Gly
65              70              75              80

Lys Ser Leu Gly Gly Ser Gly Gly Gly Ser Gly Gly Leu Met Val
                85              90              95

Val Gly Ala Val Gly Val Gly Gly Ser Gly Gly Gly Ser Gly Gly
            100             105             110

Val Thr Gly Ala Arg Gly Val Gly Lys Gly Gly Ser Gly Gly Gly Gly
            115             120             125

Ser Gly Gly Glu Tyr Lys Phe Val Val Leu Gly Thr Val Gly His Gly
        130             135             140

Lys Ser Gly Gly Ser Gly Gly Gly Gly Ser Gly Gly Glu Tyr Lys Ile
145             150             155             160

Val Val Ala Gly Asn Val Gly Ile Gly Lys Ser Gly Gly Ser Gly Gly
                165             170             175

Gly Gly Ser Gly Gly Glu Tyr Lys Phe Val Val Phe Gly Ser Asp Gly
            180             185             190

Ala Gly Lys Ser Gly Gly Ser Gly Gly Gly Gly Ser Gly Gly Met Thr
            195             200             205

Glu Tyr Lys Phe Val Val Ser Gly Ala Asp Gly Ile Gly Lys Ser Ala
    210             215             220

Leu Thr Gly Gly Ser Gly Gly Gly Gly Ser Gly Gly Met Thr Glu Tyr
225             230             235             240

Lys Phe Val Val Ile Gly Asn Arg Gly Val Gly Lys Ser Ala Leu Thr
                245             250             255

Gly Gly Ser Leu Gly Gly Gly Ser Gly Ile Val Gly Ile Val Ala
            260             265             270

Gly Leu Ala Val Leu Ala Val Val Val Ile Gly Ala Val Val Ala Thr
            275             280             285

Val Met Cys Arg Arg Lys Ser Ser Gly Gly Lys Gly Gly Ser Tyr Ser
    290             295             300

Gln Ala Ala Ser Ser Asp Ser Ala Gln Gly Ser Asp Val Ser Leu Thr
305             310             315             320

Ala
```